United States Patent
Li et al.

(10) Patent No.: US 11,111,230 B2
(45) Date of Patent: Sep. 7, 2021

(54) INDOLEAMINE 2,3-DIOXYGENASE INHIBITORS AND USE OF SAME IN MEDICINE

(71) Applicant: ADLAI NORTYE BIOPHARMA CO., LTD., Zhejiang (CN)

(72) Inventors: Pan Li, Hangzhou (CN); Qiaodong Wen, Hangzhou (CN); Ji Wang, Hangzhou (CN); Quan Gan, Hangzhou (CN); Yang Lu, Hangzhou (CN); Donghui Yang, Hangzhou (CN)

(73) Assignee: ADLAI NORTYE BIOPHARMA CO., LTD., Hangzhou (CN)

( * ) Notice: Subject to any disclaimer, the term of this patent is extended or adjusted under 35 U.S.C. 154(b) by 0 days.

(21) Appl. No.: 16/914,142

(22) Filed: Jun. 26, 2020

(65) Prior Publication Data

US 2020/0331887 A1    Oct. 22, 2020

Related U.S. Application Data

(63) Continuation of application No. PCT/CN2018/124110, filed on Dec. 27, 2018.

(30) Foreign Application Priority Data

Dec. 29, 2017    (CN) .......................... 201711478307.2
Jun. 29, 2018    (CN) .......................... 201810754253.6

(51) Int. Cl.
*C07D 215/14*    (2006.01)
*C07D 401/12*    (2006.01)
*C07D 401/08*    (2006.01)
*C07D 405/08*    (2006.01)
*C07D 409/12*    (2006.01)

(52) U.S. Cl.
CPC ......... *C07D 401/12* (2013.01); *C07D 215/14* (2013.01); *C07D 401/08* (2013.01); *C07D 405/08* (2013.01); *C07D 409/12* (2013.01)

(58) Field of Classification Search
CPC .................................................. C07D 215/14
See application file for complete search history.

(56) References Cited

U.S. PATENT DOCUMENTS

| | | |
|---|---|---|
| 2004/0072818 A1 | 4/2004 | Dunning et al. |
| 2008/0021027 A1 | 1/2008 | Benson et al. |
| 2016/0137652 A1 | 5/2016 | Beck et al. |
| 2020/0239420 A1* | 7/2020 | Kazmierski ............ A61P 31/12 |
| 2020/0239464 A1* | 7/2020 | Wu ..................... C07D 401/12 |

FOREIGN PATENT DOCUMENTS

| | | |
|---|---|---|
| CN | 1678586 | 10/2005 |
| CN | 101479249 | 7/2009 |
| CN | 107427499 | 12/2017 |
| CN | 107663159 | 2/2018 |
| WO | WO 2013134518 A1 | 9/2013 |
| WO | WO 2017192813 A1 | 11/2017 |

OTHER PUBLICATIONS

Yao et al., "What is the, etc.," Journal of Experimental & Clinical Cancer Research, 40:60, 1-14. (Year: 2020).*
Li et al., "The emerging roles, etc.," Biomedicine & Pharmacotherapy 137, 111295, 1-6. (Year: 2021).*
Yu et a.,, "The Clincopathological, etc.," Cell Physiol Biochem 49: 134-143. (Year: 2018).*
Simone, Oncology: Introduction, Cecil Textbook of Medicine, ed. Bennett et al. W.B. Saunders CO. 20th ed. vol. 1, pp. 1004-1010. (Year: 1996).*
Gura, Systems for Identifiying New Drugs Are Often Faulty, Cancer Models, Science, vol. 278 No. 5340. pp 1041-1042. (Year: 1997).*
Johnson et al., Relationships between drug activity in NCI preclinical in vitro and in vivo and early clinical trials, British J of Cancer, 64(10): 1424-1431. (Year: 2001).*
Pearce et al., Failure modes in anticancer drug discovery and development, Cancer Drug Design and Discovery ed by Stephen Neidle, chap. 18, pp. 424-435. (Year: 2008).*
Dagenais-Lussier et al., "Latest developments, etc.," Cytokine and Growth Factor Reviews 02.003, 1-7. (Year: 2021).*
Ala, "The footprint, etc.," European Journal of Pharmacology 896 173921, 1-15. (Year: 2021).*
Ogbechi et al., "IDO activation, etc.," Experimental Gerontology 131 110820, 1-8 (Year: 2020).*
Platten et al., "Tryptophan metabolism, etc.," Nature Reviews, 18, 379-401. (Year: 2019).*
Acovic et al., "Role of indoleamine, etc.," Ther Adv Gastroenterol, 11: 1-16. (Year: 2018).*
Coletti et al., "Advances in, etc.," Med. Chem. Common., 8, 1378-1392. (Year: 2017).*
English Language Abstract of CN107663159, Applicant: Shanghai De Novo Pharmatech Co., Ltd., 1 page, obtained via Espacenet, date obtained: Jun. 26, 2020, URL: <https://worldwide.espacenet.com/publicationDetails/biblio?CC=CN&NR=107663159A&KC=A&FT=D&ND=3&date=20180206&DB=&locale=en_EP>.
International Search Report and English Language Translation of International Application No. PCT/CN2018/124110, prepared by the International Searching Authority, dated Mar. 22, 2019, 21 pages.

* cited by examiner

*Primary Examiner* — Patricia L Morris
(74) *Attorney, Agent, or Firm* — Hoxie & Associates LLC

(57) ABSTRACT

The present invention relates to a compound represented by formula I, a pharmaceutical composition containing the compound of formula I, a method for inhibiting indoleamine 2,3-dioxygenase, and its use in medicine.

(I)

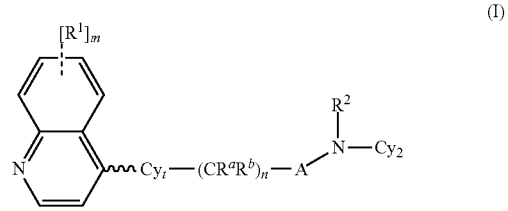

3 Claims, No Drawings

INDOLEAMINE 2,3-DIOXYGENASE INHIBITORS AND USE OF SAME IN MEDICINE

CROSS-REFERENCE TO RELATED APPLICATIONS

This application is a U.S. continuation of International Application No. PCT/CN2018/124110, filed on Dec. 27, 2018, which claims benefit from Chinese application No. 201711478307.2, filed on Dec. 29, 2017, the title of which is "indoleamine 2,3-dioxygenase inhibitors and their application in medicine" and Chinese application No. 201810754253.6, filed on Jun. 29, 2018, the title of which is "indoleamine 2,3-dioxygenase inhibitors and their application in medicine" and the disclosures of each of which are hereby incorporated by reference in their entireties.

This application claims benefit from Chinese application No. 201711478307.2, filed on Dec. 29, 2017, the title of which is "indoleamine 2,3-dioxygenase inhibitors and their application in medicine" and Chinese application No. 201810754253.6, filed on Jun. 29, 2018, the title of which is "indoleamine 2,3-dioxygenase inhibitors and their application in medicine" and the disclosures of which are both incorporated herein by reference.

FIELD

The invention relates to a novel indoleamine 2,3-dioxygenase inhibitor with inhibitory activity on tryptophan metabolism, and a pharmaceutical composition containing it as an active ingredient.

BACKGROUND

Tryptophan (TRP) is an α-amino acid used for protein biosynthesis. It contains α-amino group, α-carboxylic acid group and side chain indole. It is indispensable in human beings. The human body is not able to synthesize it, but need to obtain it from the diet. Tryptophan is also a precursor to the synthetic neurotransmitter serotonin and the hormone N-acetyl-5-methoxytryptamine (melatonin). The heme-dependent enzyme indoleamine 2,3-dioxygenase (also called IDO or IDO1) is a metabolic enzyme responsible for converting tryptophan to N-formyl-kynurenine outside the liver; this is the first step in the process of tryptophan metabolism, and also the rate-limiting step of the entire process. N-formyl-kynurenine is a precursor of various biologically active molecules kynurenine (or Kyn), and kynurenine has immunomodulatory functions (Schwarcz et al, Nat Rev Neurosci. 2012; 13 (7): 465).

Indoleamine 2,3-dioxygenase (IDO) is widely expressed in solid tumors (Uyttenhove et al, Nat Med. 2003; 10: 1269), and is also expressed in primary cancer and metastatic cancer cells. IDO is induced by proinflammatory factors in tumors, including type I and type II interferons produced by infiltrating lymphocytes (Tnani and Bayard, Biochim Biophys Acta. 1999; 1451 (1): 59; Mellor and Munn, Nat Rev Immunol 2004; 4 (10): 762; Munn, Front Biosci. 2012; 4: 734) and transforming growth factor-β (TGF-β) (Pallotta et al, Nat Immunol. 201 1; 12 (9): 870). In recent years, more and more evidence shows that IDO, as an inducible enzyme, plays a major role in the regulation of immune cells. Decreased tryptophan levels and increased kynurenine could suppress immune effector cells and promote adaptive immune suppression by inducing and maintaining regulatory T cells (Tregs; Munn, Front Biosci. 2012; 4: 734); the concentration of tryptophan in T cells is also positively correlated in the immune system. In the tumor immune microenvironment, activated or overexpressed IDO leads to the exhaustion of tryptophan, which in turn leads to T cell death, inactivation of the immune system, and ultimately to tumor immune tolerance and immune escape. Existing studies have shown that the immune imbalance caused by IDO is deeply involved in the formation and progression of tumors. Therefore, IDO receptor has become an important target for tumor and other immunotherapy. In addition to tumors, IDO is also associated with viral infections, depression, organ transplant rejection, or autoimmune diseases (Johnson and Munn, Immunol Invest 2012; 41 (6-7): 765). Therefore, drugs targeting IDO are also of great value for the treatment of the above diseases. In short, developing an active and selective IDO inhibitor that can effectively treat diseases caused by harmful substances in the kynurenine pathway via regulating kynurenine channels and maintaining the level of tryptophan in the body is necessary as a monotherapy or combination therapies.

A large number of published preclinical data further confirmed the role of IDO in the anti-tumor immunity. IDO inhibitors can be used to activate T cells, thereby increasing the activation of T cells when they are suppressed by viruses such as pregnancy, malignancy, or HIV. Forced IDO induction in cancer cells proved to have a survival advantage (Uyttenhove et al, Nat Med. 2003; 10: 1269). Another in vivo study shows that IDO inhibitors reduce the dependence on lymphocytes by reducing kynurenine levels during tumor growth (Liu et al, Blood. 2010; 115 (17): 3520). Preclinical studies have also shown that IDO inhibitors have a synergistic effect if used in combination with other tumor drugs, such as radiotherapy, chemotherapy or vaccines. (Koblish et al, Mol Cancer Ther. 2010; 9 (2): 489, Hou et al, Cancer Res. 2007; 67 (2): 792; Sharma et al, Blood. 2009; 1 13 (24): 6102).

The research on IDO inhibitors and anti-tumor drugs has made important progress globally, such as INCB024360, NLG919 and BMS-986205 have all entered the clinic. However, due to the limitation of the adversed effects, INCB024360 makes the current clinical research dose (50 mg bid, or 100 mg bid) about 30% of the optimal dose (300 mg bid, 600 mg bid), and therefore the clinical activity is greatly limited; meanwhile, the pharacophore of INCB024360 is also a toxicophore, which might explain that its derivatives still suffer from the similar toxicity issue. The safety profiling of NLG919 is better in the expense of worse biological activity. BMS-986205 has just entered the clinic at present with limited clinical data revealed. We view the discovery of novel molecules based on the structure of BMS-986520 a better chance to yield candidates with excellent biological avicity and safety profiling, with the goal of curing tumors rather than inhibiting them.

SUMMARY

In one aspect, the present invention provides a compound represented by formula I,

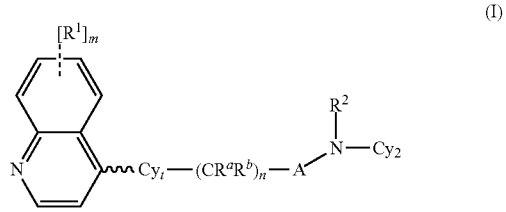

in which ∿∿ represents; ———, ||||||||| or ▬;

A represent —C(O)—, —S(O)$_2$— or —S(O)—;

in which, every $R^1$ is respectively selected from hydrogen, halogen, hydroxyl, nitro, cyano, sulfonate, $C_{1-6}$alkyl, $C_{3-6}$cycloalkyl, $C_{2-6}$alkenyl, $C_{2-6}$alkynyl, $C_{1-6}$alkoxy, $C_1$-$C_6$ haloalkyl, $C_1$-$C_6$haloalkoxy, $C_1$-$C_6$halocycloalkyl, $C_{1-6}$alkylthio, $C_{1-6}$alkylcarbonyl, $C_{1-6}$alkoxycarbonyl, di($C_{1-6}$Alkyl) amino$C_{2-6}$ alkoxycarbonyl, amino, $C_{1-6}$alkylamino, di($C_{1-6}$alkyl) amino, carbamoyl, $C_{1-6}$alkylcarbamoyl, di ($C_{1-6}$alkyl Group) carbamoyl, bis ($C_{1-6}$alkyl)amino$C_{2-6}$ alkyl carbamoyl, sulfamoyl, $C_{1-6}$alkyl sulfamoyl, di ($C_{1-6}$alkyl) sulfamoyl, di($C_{1-6}$alkyl) amino $C_{2-6}$alkylsulfamoyl, $C_{1-6}$alkylsulfonyl, $C_{1-6}$alkylsulfinyl, di ($C_{1-6}$ alkyl) phosphono, hydroxy $C_{1-6}$alkyl Group, hydroxycarbonyl $C_{1-6}$ alkyl, $C_{1-6}$ alkoxy $C_{1-6}$alkyl, $C_{1-6}$alkylsulfonyl$C_{1-6}$alkyl, $C_{1-6}$alkylsulfinyl $C_{1-6}$alkyl, di($C_{1-6}$alkyl) phosphono $C_{1-6}$alkyl, hydroxy $C_{2-6}$alkoxy, $C_{1-6}$alkoxy$C_{2-6}$alkoxy, amino $C_{1-6}$alkyl, $C_{1-6}$alkylamino$C_{1-6}$alkyl, di($C_{1-6}$alkyl) amino$C_{1-6}$ alkyl, di($C_{1-6}$alkyl) aminoacetyl, amino $C_{2-6}$alkoxy, $C_{1-6}$alkylamino$C_{2-6}$alkoxy, di($C_{1-6}$alkyl) amino $C_{2-6}$ alkoxy, hydroxy $C_{2-6}$ alkylamino, $C_{1-6}$alkoxy$C_{2-6}$alkylamino, amino$C_{2-6}$ alkylamino, $C_{1-6}$alkylamino$C_{2-6}$alkylamino, di($C_{1-6}$ alkyl)amino$C_{2-6}$alkylamino; or adjacent $R^1$ Ring together to form a 3-8 membered ring, selectively, the ring contains 0, 1, 2, 3 heteroatoms.

$Cy_1$ is selected from the group consisting of a 5-15 membered bridged ring group, a 5-15 membered spirocyclic group, a 5-15 membered bridged heterocyclic group, or a 5-15 membered spiro heterocyclic group substituted with an arbitrary substituent. The substituent is selected from halogen, hydroxyl, $C_{1-6}$alkyl, amino, halogenated $C_{1-6}$alkyl, mercapto, $C_{1-6}$alkylmercapto, $C_{1-6}$alkylamino, di($C_{1-6}$alkyl) amino, cyano;

$R^a$, $R^b$, $R^2$ are each independently selected from hydrogen, $C_1$-$C_6$ alkyl or $C_{3-6}$cycloalkyl;

$Cy_2$ is $C_5$-$C_{10}$ aryl, $C_5$-$C_{10}$ heteroaryl, $C_5$-$C_{10}$ cycloalkyl, $C_5$-$C_{10}$ heterocycloalkyl containing one or more substituents, the substituent is selected from halogen, hydroxy, nitro, cyano, sulfonate, $C_{1-6}$alkyl, $C_{2-6}$alkenyl, $C_{2-6}$alkynyl, $C_{3-6}$cycloalkyl, $C_{1-6}$alkoxy, $C_1$-$C_6$ haloalkyl, $C_1$-$C_6$haloalkoxy, $C_{1-6}$ alkylthio, $C_{1-6}$alkylcarbonyl, $C_{1-6}$alkylthio, $C_{1-6}$alkylcarbonyl, $C_{1-6}$alkylcarbonyloxy, $C_{1-6}$alkoxycarbonyl, di($C_{1-6}$alkyl)amino$C_{2-6}$alkoxycarbonyl, amino, $C_{1-6}$alkylamino, di($C_{1-6}$alkyl)amino, carbamoyl, $C_{1-6}$alkylcarbamoyl, di($C_{1-6}$alkyl) carbamoyl, di($C_{1-6}$alkyl) $C_{2-6}$alkylcarbamoyl, sulfamoyl, $C_{1-6}$alkylsulfamoyl, di($C_{1-6}$alkyl)sulfamoyl, di($C_{1-6}$alkyl)amino$C_{2-6}$alkylsulfamoyl, $C_{1-6}$alkylsulfonyl, $C_{1-6}$alkylsulfinyl, di($C_{1-6}$alkyl) phosphono, hydroxy$C_{1-6}$alkyl, hydroxycarbonyl $C_{1-6}$alkyl, $C_{1-6}$alkoxy$C_{1-6}$alkyl, $C_{1-6}$alkylsulfonyl$C_{1-6}$alkyl, $C_{1-6}$alkylsulfinyl $C_{1-6}$alkyl, di($C_{1-6}$alkyl)phosphono$C_{1-6}$alkyl, hydroxy$C_{2-6}$alkoxy, $C_{1-6}$alkoxy$C_{2-6}$alkoxy, amino$C_{1-6}$alkyl, $C_{1-6}$alkylamino$C_{1-6}$alkyl, di($C_{1-6}$alkyl)amino$C_{1-6}$alkyl, di ($C_{1-6}$alkyl) aminoacetyl, amino$C_{2-6}$alkoxy, $C_{1-6}$alkylamino$C_{2-6}$alkoxy, di($C_{1-6}$ alkyl)amino$C_{2-6}$alkoxy, hydroxy $C_{2-6}$alkylamino, $C_{1-6}$alkoxy$C_{2-6}$alkylamino, amino$C_{2-6}$alkylamino, $C_{1-6}$alkylamino$C_{2-6}$alkylamino, di($C_{1-6}$alkyl)amino$C_{2-6}$alkylamino, —S(O)$C_{1-6}$alkyl; or when two substituents are adjacent, Can form a 3-8 member ring, the 3-8 member ring can contain 0, 1, 2, 3 O, S, N atoms; m, n is 0, 1, 2, 3, 4.

In another technical solution of the present invention, $Cy_1$ is selected from an 8-12 membered spirocyclic group or 8-12 membered spirocyclic group substituted with a substituent, an 8-12 membered bridged heterocyclic group, or an 8-12 membered spirohetero Cyclic group, the substituents are: halogen, hydroxyl, $C_{1-6}$alkyl, amino, $C_{1-6}$ haloalkyl, mercapto, $C_{1-6}$ alkylmercapto, $C_{1-6}$ alkylamino, di($C_{1-6}$alkyl) amino, cyano.

In another technical solution of the present invention, $Cy_1$ is selected from the following groups:

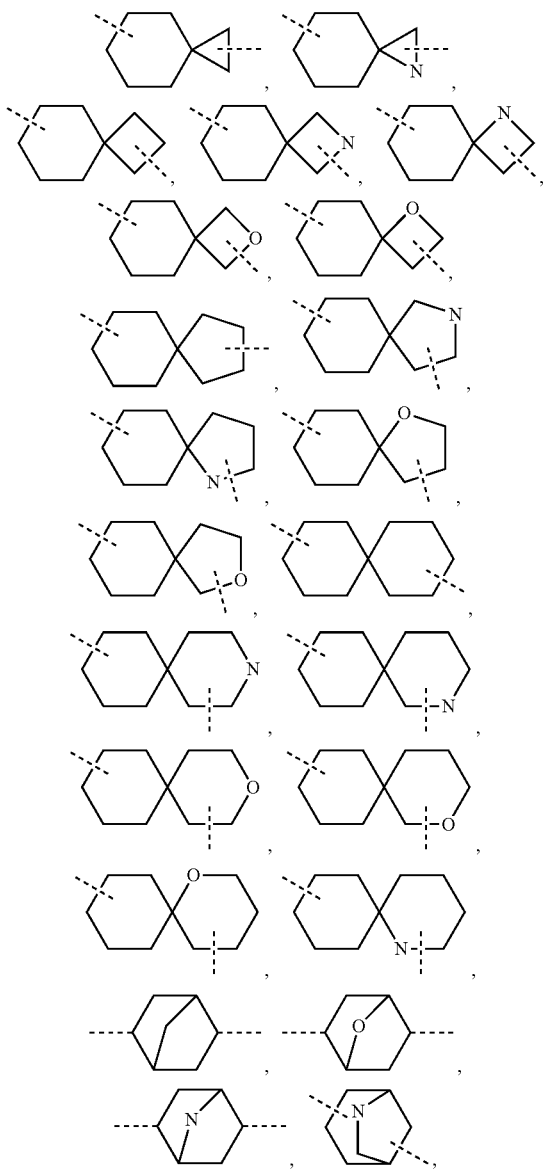

The above groups may be selected from halogen, hydroxyl, $C_{1-6}$ alkyl, amino, $C_{1-6}$haloalkyl, mercapto, $C_{1-6}$alkylmercapto, $C_{1-6}$alkylamino, di($C_{1-6}$alkyl) Substitution of amino and cyano substituents.

In another technical solution of the present invention, $Cy_1$ is selected from the following groups:

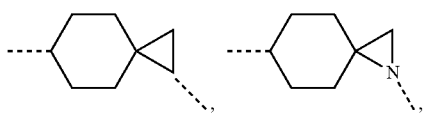

-continued

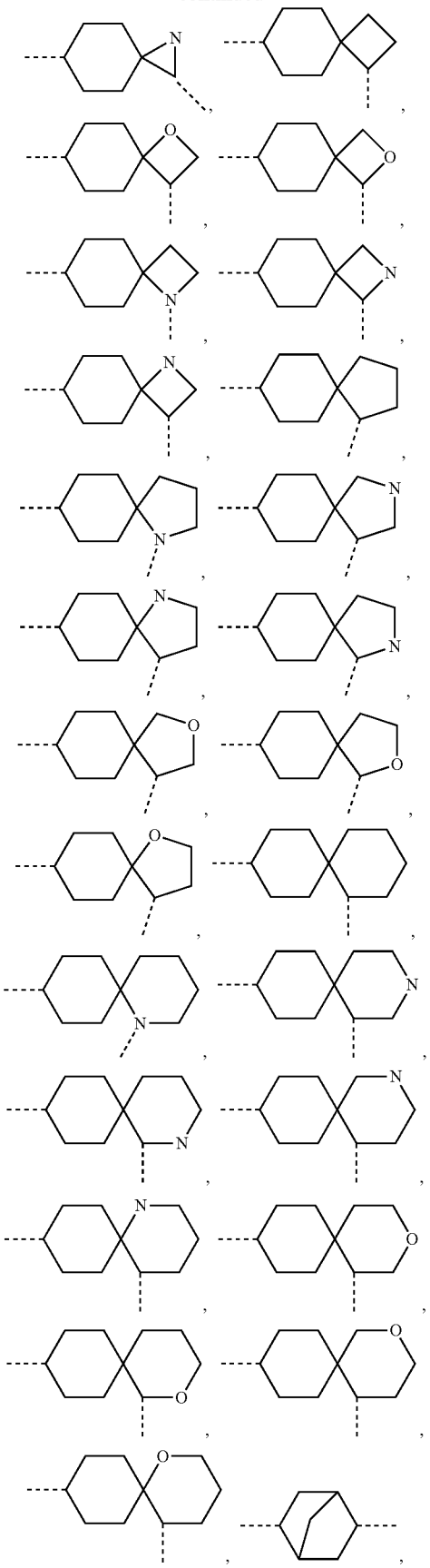

-continued

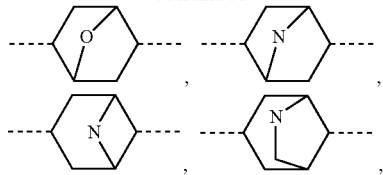

The above groups may be selected from halogen, hydroxyl, $C_{1-6}$ alkyl, amino, $C_{1-6}$haloalkyl, mercapto, $C_{1-6}$alkylmercapto, $C_{1-6}$alkylamino, di($C_{1-6}$alkyl) Substitution of amino and cyano substituents.

In one aspect, the present invention provides a compound represented by formula (II),

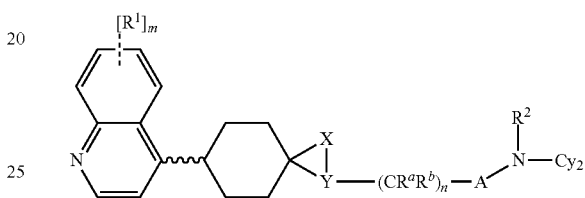

(II)

Wherein, $R^1$, $R^2$, $R^a$, $R^b$, $Cy_2$, m, n, A are as defined in formula I; X is selected from ($CR^cR^d$) o, where optionally $CR^cR^d$ can be replaced by O or $NR^e$; Y is selected from $CR^f$ or N; Wherein $R^c$, $R^d$, $R^e$, and $R^f$ are each independently selected from hydrogen or $C_{1-6}$alkyl; o is selected from 0, 1, 2, 3, 4, and 5.

In one aspect, the present invention provides a compound represented by formula (III),

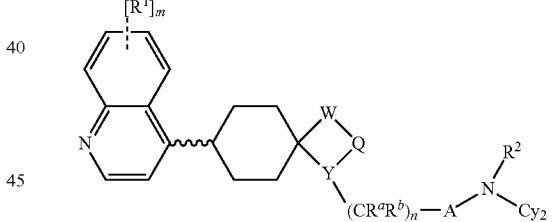

(III)

Wherein, W, Q is selected from $CR^cR^d$ or $NR^e$; A, $R^1$, $R^2$, $R^a$, $R^b$, $R^c$, $R^d$, $R^e$. $Cy_2$, m, n, Y are as defined in formula II.

In one aspect, the present invention provides a compound represented by formula (III),

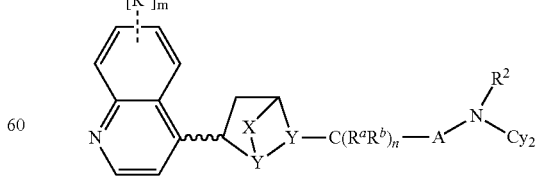

(IV)

Wherein, $R^1$, $R^2$, $R^a$, $R^b$, $Cy_2$, m, n, X, Y are as defined in formula II Z is selected from $(CR^g)_p$, each $CR^g$ can be replaced by N; each $R^g$ is independently selected from hydrogen or $C_{1-6}$alkyl.

In a preferred technical solution of the present invention, it has the structure of formula (V):

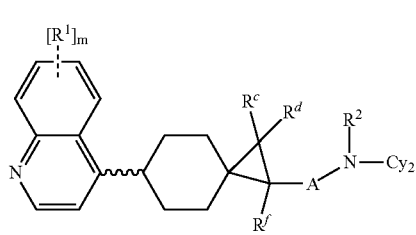

(V)

Wherein, $R^1$, $R^2$, $R^c$, $R^d$, $R^f$, $Cy_2$, m, A are as defined in formula II.

In a preferred technical solution of the present invention, it has the structure of formula (VI):

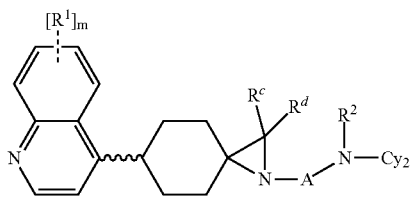

(VI)

Wherein, $R^1$, $R^2$, $R^c$, $R^d$, $Cy_2$, m, A are as defined in formula II.

In a preferred technical solution of the present invention, it has the structure of formula (VII):

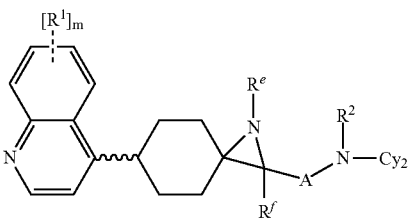

(VII)

Wherein, $R^1$, $R^2$, $R^f$, $Cy_2$, m, A are as defined in formula II.

In a preferred technical solution of the present invention, it has the structure of formula (VIII):

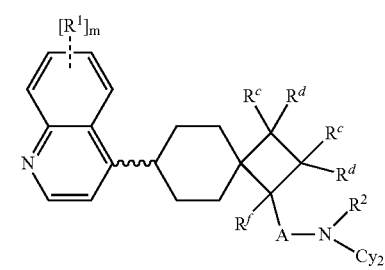

(VIII)

Wherein, $R^1$, $R^2$, $R^c$, $R^d$, $Cy_2$, m, A are as defined in formula II.

In a preferred technical solution of the present invention, it has the structure of formula (IX):

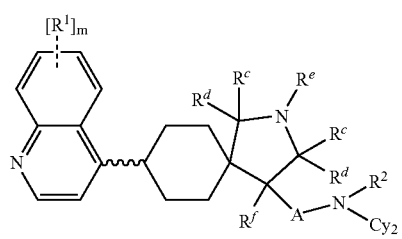

(IX)

Wherein, $R^1$, $R^2$, $R^c$, $R^d$, $R^e$, $R^f$, $Cy_2$, m, A are as defined in formula II.

In the present invention, ∿∿ represent ———, ׀׀׀׀׀׀׀׀ or ▶;

In a preferred technical solution of the present invention, ∿∿ is preferred to be ׀׀׀׀׀׀׀׀.

In the present invention, A is selected from —C(O)— or $S(O)_2$—.

The invention also provides a method for preparing a compound having the structure of formula (X):

Pathway I

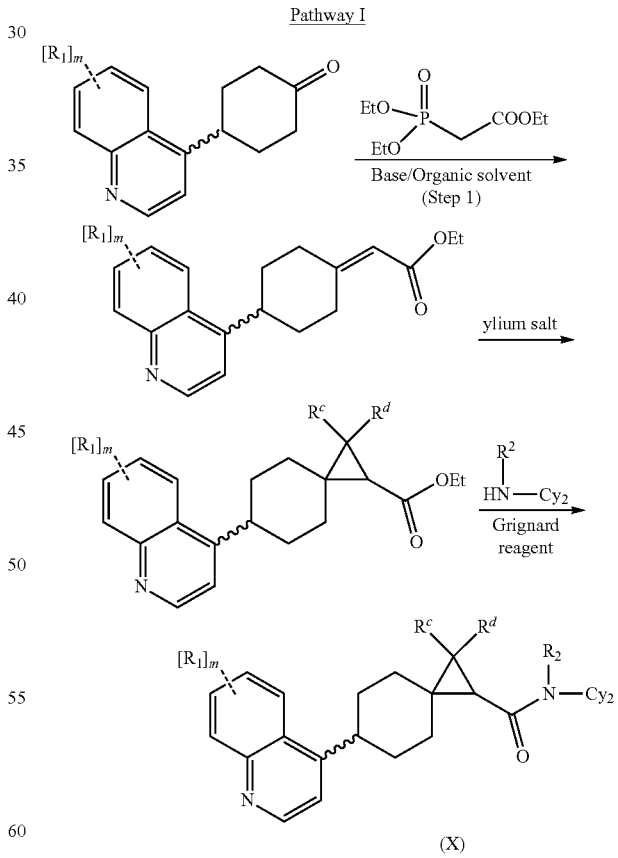

(X)

In pathway I:

The base used in step (1) is selected from inorganic bases or organic bases, including but not limited to: sodium hydride, calcium hydride, sodium amide, sodium methoxide, sodium ethoxide, potassium hydroxide, sodium hydroxide, lithium hydroxide, hydrogenation Lithium aluminum, tert-butyl lithium, tert-butyl potassium, potassium tert-butoxide, lithium diisopropylamide, barium hydroxide, or any combination thereof;

The organic solvents used in step (1) include but are not limited to: 1,4-dioxane, N, N-dimethylformamide, dichloromethane, chloroform, DMSO, DMF, THF, acetone, methanol, Ethanol or any combination thereof;

Wherein the ylium salt used in step (2) is selected from sulfur ylide or phosphorus ylide The Grignard reagent used in step (3) is selected from CH₃MgCl, CH₃MgBr, C₂H₅MgCl, C₂H₅MgBr, i-PrMgCl, i-PrMgBr, PhCH₂MgCl, PhCH₂MgBr or any combination thereof.

The invention also provides a method for preparing a compound having the structure of formula (XI):

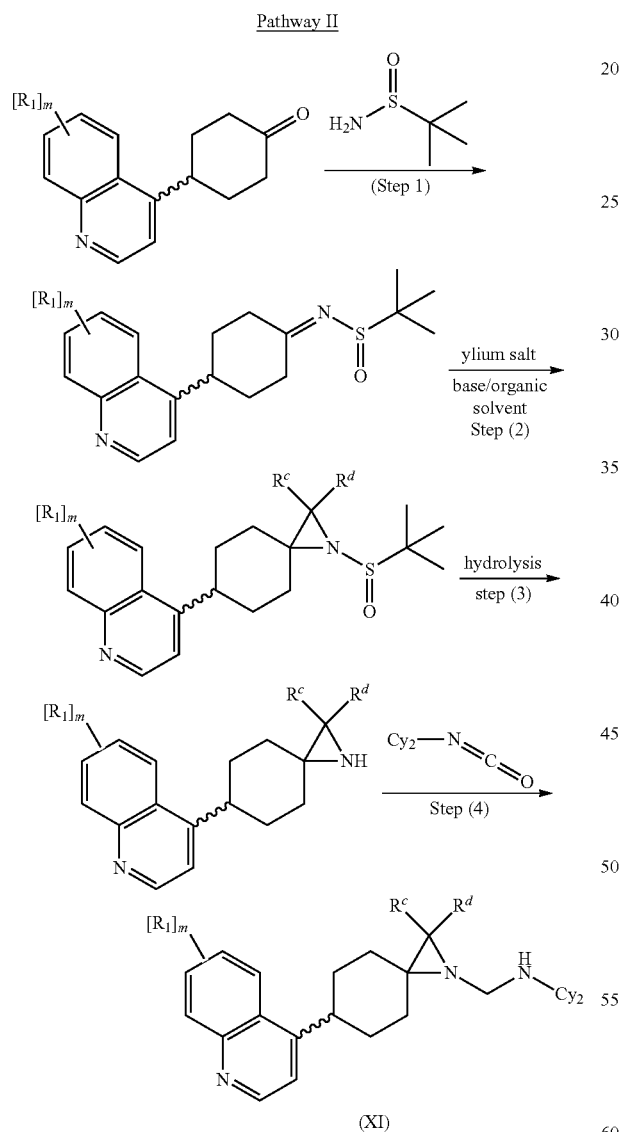

In pathway II:
Wherein the catalyst used in step (1) is selected from methyl titanate, ethyl titanate, n-propyl titanate, isopropyl titanate, butyl titanate or any combination thereof;

The base used in step (2) is selected from inorganic bases or organic bases, including but not limited to: sodium hydride, calcium hydride, sodium amide, sodium methoxide, sodium ethoxide, potassium hydroxide, sodium hydroxide, lithium hydroxide, hydrogenation Lithium aluminum, tert-butyl lithium, tert-butyl potassium, potassium tert-butoxide, lithium diisopropylamide, barium hydroxide, or any combination thereof;

The organic solvents used in step (2) include but are not limited to: 1,4-dioxane, N, N-dimethylformamide, dichloromethane, chloroform, DMSO, DMF, THF, acetone, methanol, Ethanol or any combination thereof;

Wherein the ylium salt used in step (2) is selected from sulfur ylide or phosphorus ylide The hydrolysis in step (3) is performed under acidic conditions, and the acid is selected from but not limited to hydrochloric acid, sulfuric acid, hydrobromic acid, oxalic acid, citric acid, formic acid, acetic acid or any combination thereof;

The organic solvents used in step (4) include but are not limited to: 1,4-dioxane, N, N-dimethylformamide, dichloromethane, chloroform, DMSO, DMF, THF, acetone, methanol, Ethanol or any combination thereof.

The invention also provides a method for preparing a compound having the structure of formula (XII):

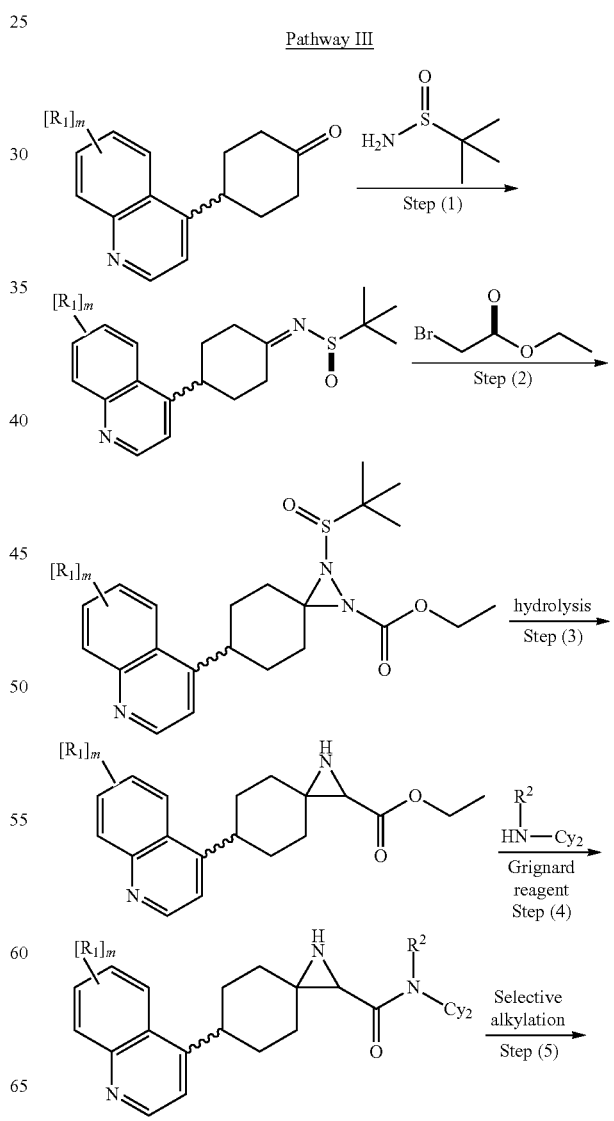

-continued

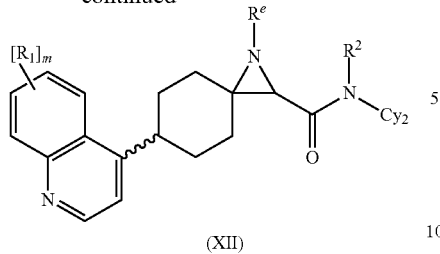

(XII)

In pathway III:
Wherein the catalyst used in step (1) is selected from methyl titanate, ethyl titanate, n-propyl titanate, isopropyl titanate, butyl titanate or any combination thereof;

Wherein the step (2) is performed under the action of a strong non-nucleophilic base selected from but not limited to lithium diisopropylamide, lithium diethylamide, isopropyl-cyclohexylamino Lithium, lithium dicyclohexylamide, lithium 2,2,6,6-tetramethylpiperidino, lithium hexamethyl-disilazide;

The hydrolysis in step (3) is performed under acidic conditions, and the acid is selected from but not limited to hydrochloric acid, sulfuric acid, hydrobromic acid, oxalic acid, citric acid, formic acid, acetic acid or any combination thereof;

The Grignard reagent used in step (4) is selected from $CH_3MgCl$, $CH_3MgBr$, $C_2H_5MgCl$, $C_2H_5MgBr$, i-PrMgCl, i-PrMgBr, $PhCH_2MgCl$, $PhCH_2MgBr$ or any combination thereof Wherein when performing the alkylation reaction described in step (4), the alkylation reaction reagent is selected from haloalkyl, the reaction is performed under a Lewis acid as a catalyst, and the Lewis acid is preferably $AlCl_3$, $FeCl_2$, $CuCl_2$.

The invention also provides a method for preparing a compound having the structure of formula (XIII):

Pathway IV

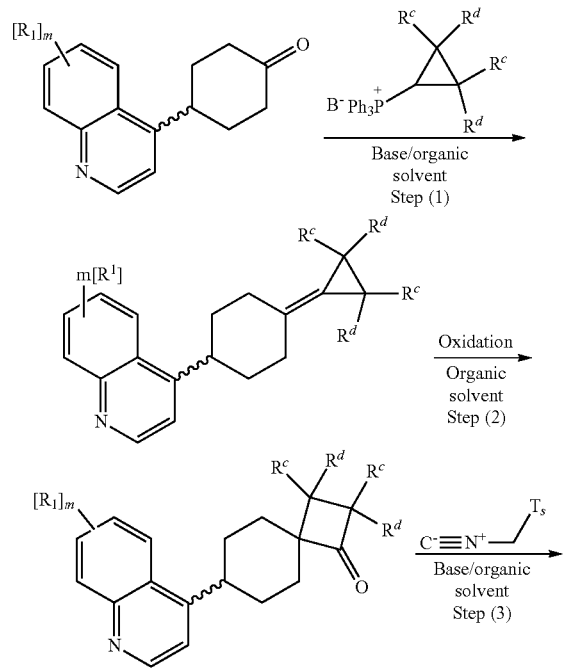

-continued

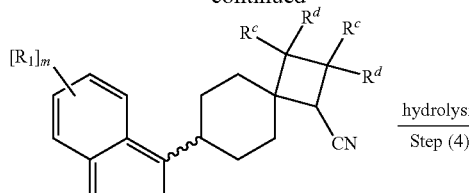

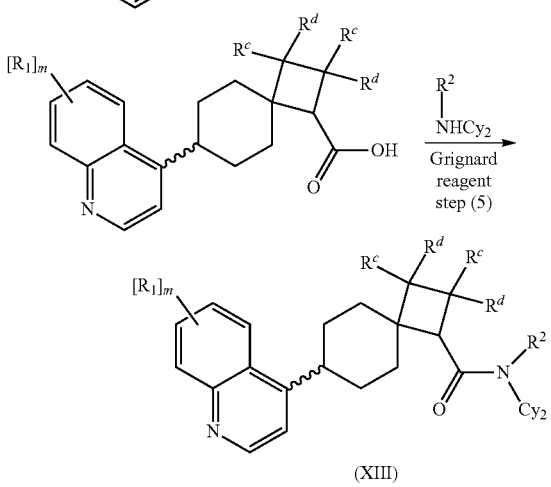

(XIII)

In pathway IV,
The base used in step (1) and step (3) is selected from inorganic bases or organic bases, including but not limited to: sodium hydride, calcium hydride, sodium amide, sodium methoxide, sodium ethoxide, potassium hydroxide, sodium hydroxide, Lithium hydroxide, lithium aluminum hydride, tert-butyl lithium, tert-butyl potassium, potassium tert-butoxide, lithium diisopropylamide, barium hydroxide, or any combination thereof;

The organic solvents used in step (1) to step (3) include but are not limited to: 1,4-dioxane, N, N-dimethylformamide, dichloromethane, chloroform, DMSO, DMF, THF, acetone, methanol, ethanol or any combination thereof;

The oxidant used in step (2) is selected from but not limited to m-chloroperoxybenzoic acid, $CrO_3$, $KMnO_4$, $MnO_2$, $NaCr_2O_7$, $HIO_4$, $PbAc_4$, $OsO_4$, hydrogen peroxide or any combination thereof;

Wherein the hydrolysis reaction in step (4) is performed under acidic conditions, and the acid is selected from but not limited to hydrochloric acid, sulfuric acid, hydrobromic acid, oxalic acid, citric acid, formic acid, acetic acid or any combination thereof;

The Grignard reagent used in step (5) is selected from $CH_3MgCl$, $CH_3MgBr$, $C_2H_5MgCl$, $C_2H_5MgBr$, i-PrMgCl, i-PrMgBr, $PhCH_2MgCl$, $PhCH_2MgBr$ or any combination thereof;

The invention also provides a method for preparing a compound having the formula (XIV):

Pathway V

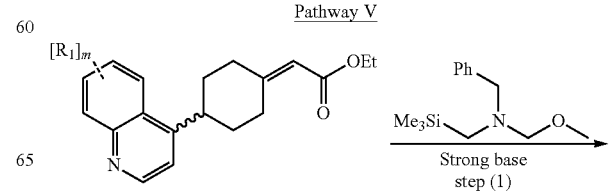

Strong base
step (1)

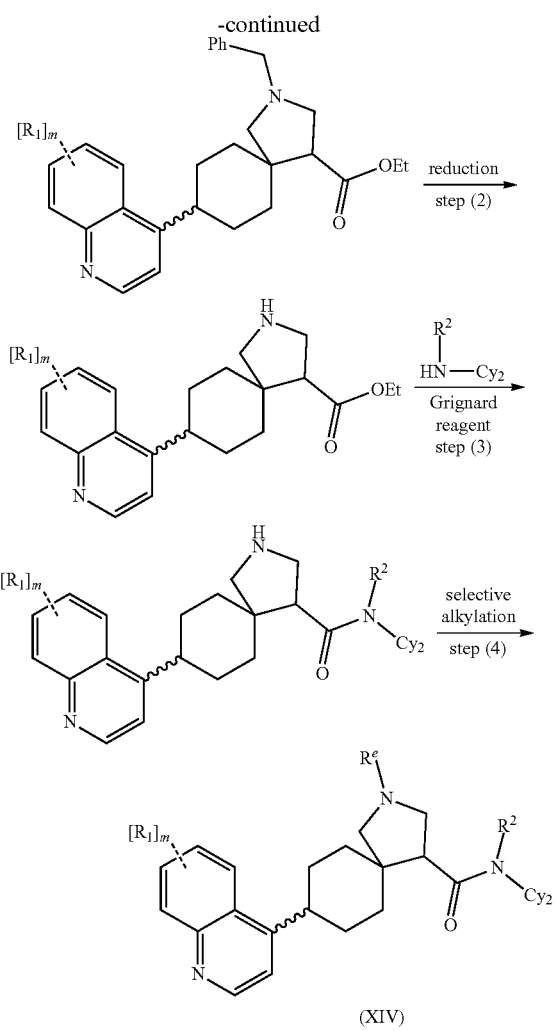

(XIV)

In pathway V:

Wherein step (1) is carried out in the presence of alkali metal fluoride or alkaline earth metal fluoride, said alkali metal fluoride is selected from but not limited to LiF, NaF, KF, $MgF_2$, $CaF_2$;

The reduction reaction in step (2) can be palladium-carbon catalytic hydrogenation reduction or Na/liquid ammonia reduction;

The Grignard reagent used in step (3) is selected from $CH_3MgCl$, $CH_3MgBr$, $C_2H_5MgCl$, $C_2H_5MgBr$, i-PrMgCl, i-PrMgBr, $PhCH_2MgCl$, $PhCH_2MgBr$ or any combination thereof;

Wherein when performing the alkylation reaction described in step (4), the alkylation reaction reagent is selected from haloalkyl, the reaction is performed under a Lewis acid as a catalyst, and the Lewis acid is preferably $AlCl_3$, $FeCl_2$, $CuCl_2$.

DETAILED DESCRIPTION OF THE INVENTION

Here, when referring to a "compound" having a specific structural formula, its stereoisomers, diastereomers, enantiomers, racemic mixtures, and isotopic derivatives are also generally covered. It is well known to the technical persons skilled in the art that salts, solvates, and hydrates of a compound are alternative existing forms of the compound, and they can all be converted into the compound under certain conditions, so when referring to a compound In general, it also includes its pharmaceutically acceptable salts, and further includes its solvates and hydrates. Similarly, when referring to a compound herein, it generally includes its prodrugs, metabolites and nitrogen oxides.

The compound of the present invention may also be prepared in the form of a pharmaceutically, acceptable salt formed with an inorganic or organic acid such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The pharmaceutically acceptable salt of the present invention may be prepared by conventional methods, for example, by dissolving the compound in a water-miscible organic solvent such as acetone, methanol, ethanol and acetonitrile, adding thereto an excess amount of an organic acid or an aqueous solution of inorganic acid, to induce precipitation of salts from the resulting mixture, removing the solvent and remaining free acid therefrom, and isolating the precipitated salts.

Accordingly, the present invention provides a use of the inventive compound for the manufacture of a medicament for preventing or treating cancers, tumors, inflammatory diseases, autoimmune diseases, or immunologically mediated diseases.

In addition, the present invention provides a pharmaceutical composition for preventing or treating cancers, tumors, inflammatory diseases, autoimmune diseases, or immunologically mediated diseases which comprises the inventive compound as an active ingredient.

Further, the present invention provides a method for preventing or treating cancers, tumors, inflammatory diseases, autoimmune diseases, or immunologically mediated diseases, which comprises administering the inventive compound to a mammal in need thereof.

Accordingly, such tumor and cancer selected but not limited from skin cancer, bladder cancer, Ovarian cancer, breast cancer; gastric carcinoma, pancreatic cancer; prostatic cancer, colorectal carcinoma, lung cancer, bone cancer, brain cancer, neurocytoma, rectal cancer, colon cancer, familial adenomatous polyposis, hereditary nonpolyposis colorectal cancer, esophageal carcinoma, lip cancer, laryngocar, hypopharyngeal carcinoma, tongue cancer, salivary gland carcinoma, gastric carcinoma, adenocarcinoma, medullary thyroid carcinoma, papillary thyroid cancer, kidney cancer, carcinoma of renal pelvis, ovarian carcinoma, cervical carcinoma, carcinoma of the corpus uteri, endometrial carcinoma, choriocarcinoma, prostatic cancer, pancreatic cancer, testicular cancer, urinary cancer, melanoma, brain tumors such as glioblastoma and astrocytoma, meningeoma, Neuroblastoma and peripheral neuroectodermal tumor, Hodgkin's lymphoma, Non Hodgkin's lymphoma, Burkitt's lymphoma, acute lymphoid leukemia, acute lymphoblastic leukemia (ALL), chronic lymphocytic leukemia (CLL), acute myeloid leukemia (AML), chronic myelogenous leukemia (CML), adult T-cell leukemia lymphoma, diffuse large B cell lymphoma (DLBCL), hepatic cellular cancer, gallbladder cancer, bronchogenic carcinoma, small-cell lung carcinoma, non-small-cell lung cancer, multiple myeloma, basaloma, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, plasmacytoma.

When the compound of the present invention or a pharmaceutically acceptable salt thereof is administered in combination with another anticancer agent for treating cancer or tumor, the compound of the present invention or a pharmaceutically acceptable salt thereof can provide enhanced anticancer effects.

Representative examples of anticancer agents used to treat cancer or tumors may include, but are not limited to cell signal transduction inhibitors (for example chlorambucil, melphalan, cyclophosphamide, ifosfamide, busulfan, carmustine, lomustine, streptozotocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, Topotecan, irinotecan, etoposide, trabectedin, probiotic, doxorubicin, epirubicin, daunorubicin, mitoxantrone, bleomycin, mitomycin C, ixabepilone, tamoxifen, flutamide, gonadorelin analogs, megestrol, prednisone, dexamethasone, methylprednisolone, thalidomide, interferonα, alcium Folinate, sirolimus, sirolimus lipid, everolimus, afatinib, alisertib, amuvatinib, apatinib, axitinib, bortezomib, bosutinib, brivanib, carbotinib, cediranib, crenolanib, crizotinib, dabriafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, lenatinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tilatinib, tivantinib, Livozanib, tofacitinib, trametinib, vandetanib, veliparib, vemurafenib, visinodegib, volasertib, alemtuzumab, bevacizumab, brentuximab vedotin, victorin, catumaxomab, cetuximab, denosumab, getuzumab, ipilimumab, nimotuzumab, ofatumumab, panitumumab, rituximab, Tositumomab, trastuzumab or any combination of the abovementioned agents).

The invention also relates to a method for inhibiting indoleamine 2,3-dioxygenase, which comprises exposing the compound or pharmaceutical composition of the invention to indoleamine 2,3-dioxygenase.

The compound of the present invention or a pharmaceutically acceptable salt thereof can be administered orally or parenterally as an active ingredient, and its effective amount ranges from 0.1 to 2,000 mg/kg body weight/day in the case of mammals including humans (body weight about 70 kg), It is preferably 1 to 1,000 mg/kg body weight/day, and is administered in single or 4 divided doses per day, or with/without following a predetermined time. The dosage of the active ingredient can be adjusted according to a number of relevant factors (such as the condition of the subject to be treated, the type and severity of the disease, the rate of administration and doctor's opinion). In some cases, an amount less than the above dose may be appropriate. If it does not cause harmful side effects, an amount greater than the above dose can be used and the amount can be administered in divided doses per day.

The pharmaceutical composition of the present invention can be formulated into tablets, granules, powders, capsules, syrups, emulsions for oral administration or parenteral administration (including intramuscular, intravenous and subcutaneous routes) according to any of the conventional methods In the form of microemulsion.

The pharmaceutical composition of the present invention for oral administration can be prepared by mixing the active ingredient with carriers such as cellulose, calcium silicate, corn starch, lactose, sucrose, dextrose, calcium phosphate, stearic acid, Magnesium stearate, calcium stearate, gelatin, talc, surfactants, suspending agents, emulsifiers and diluents. Examples of the carrier used in the injection composition of the present invention are water, saline solution, glucose solution, glucose-like solution, alcohol, glycol, ether (eg, polyethylene glycol 400), oil, Fatty acids, fatty acid esters, glycerides, surfactants, suspending agents and emulsifiers.

EXAMPLES

| NO. | Compound structure |
| --- | --- |
| 1 | 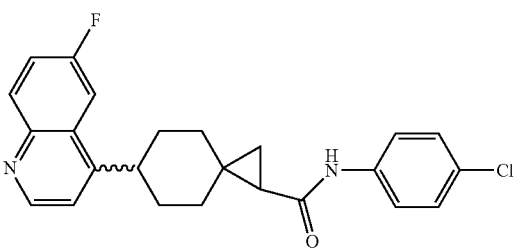 |
| 2 | 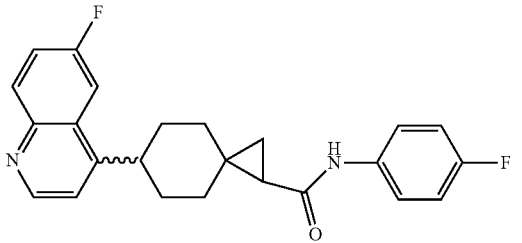 |

-continued
| NO. | Compound structure |
|---|---|
| 3 | 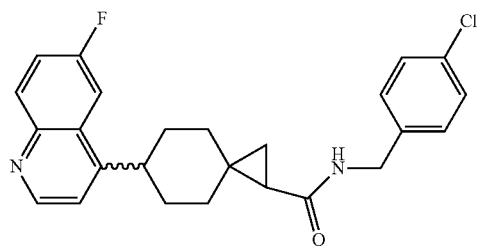 [SMILES: O=C(NCc1ccc(Cl)cc1)C1CC12CCC(c1ccnc3ccc(F)cc13)CC2] |
| 4 | 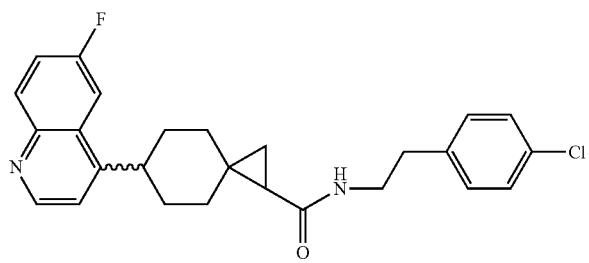 [SMILES: O=C(NCCc1ccc(Cl)cc1)C1CC12CCC(c1ccnc3ccc(F)cc13)CC2] |
| 5 | 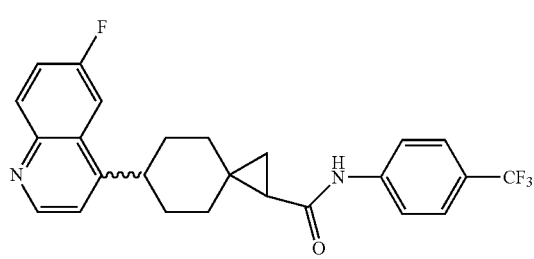 |
| 6 | 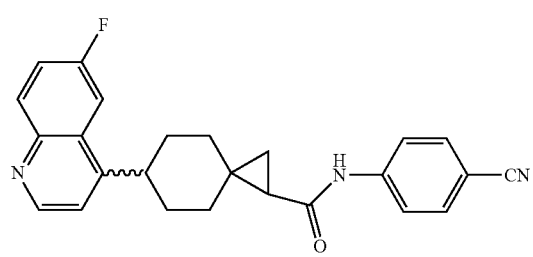 [SMILES: N#Cc1ccc(NC(=O)C2CC23CCC(c2ccnc4ccc(F)cc24)CC3)cc1] |
| 7 | 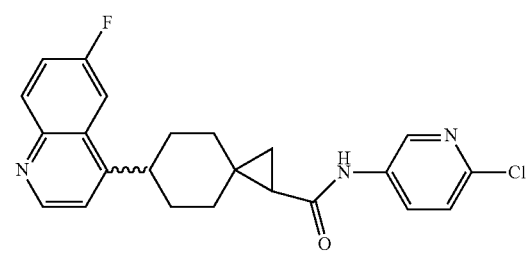 [SMILES: O=C(Nc1ccc(Cl)nc1)C1CC12CCC(c1ccnc3ccc(F)cc13)CC2] |
| 8 | 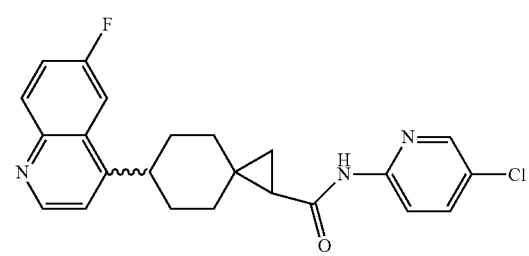 [SMILES: O=C(Nc1ccc(Cl)cn1)C1CC12CCC(c1ccnc3ccc(F)cc13)CC2] |

-continued

| NO. | Compound structure |
|---|---|
| 9 | 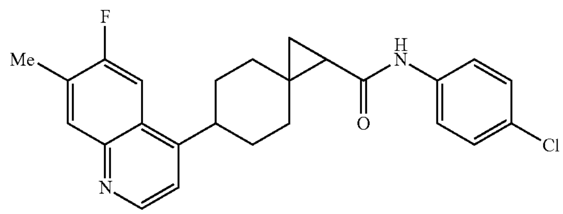 |
| 10a | 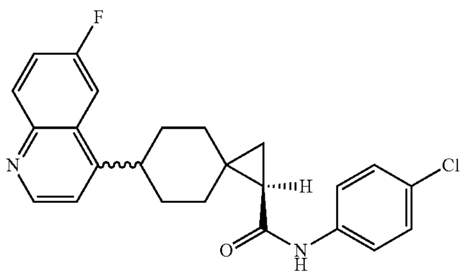 [SMILES: O=C(Nc1ccc(Cl)cc1)[C@@H]1CC12CCC(c1ccnc3ccc(F)cc13)CC2] |
| 10b | 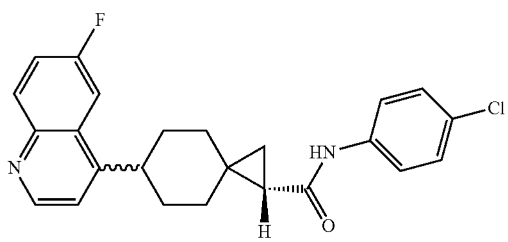 [SMILES: O=C(Nc1ccc(Cl)cc1)[C@H]1CC12CCC(c1ccnc3ccc(F)cc13)CC2] |
| 11 | 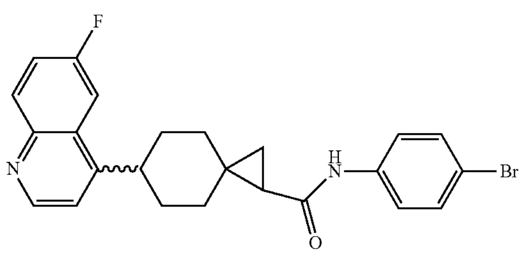 [SMILES: O=C(Nc1ccc(Br)cc1)C1CC12CCC(c1ccnc3ccc(F)cc13)CC2] |
| 12 | 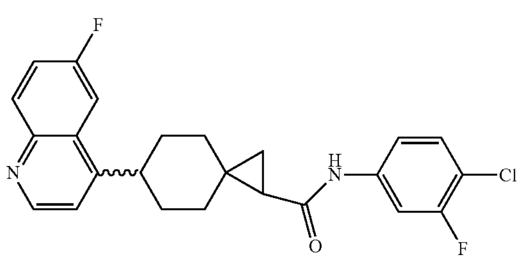 [SMILES: O=C(Nc1ccc(Cl)c(F)c1)C1CC12CCC(c1ccnc3ccc(F)cc13)CC2] |
| 13 | 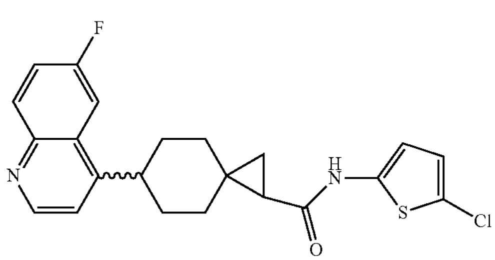 [SMILES: O=C(Nc1ccc(Cl)s1)C1CC12CCC(c1ccnc3ccc(F)cc13)CC2] |

-continued
| NO. | Compound structure |
|---|---|
| 14 | 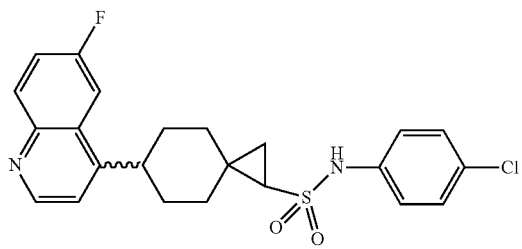 [SMILES: O=S(=O)(Nc1ccc(Cl)cc1)C1CC12CCC(c1ccnc3ccc(F)cc13)CC2] |
| 15 | 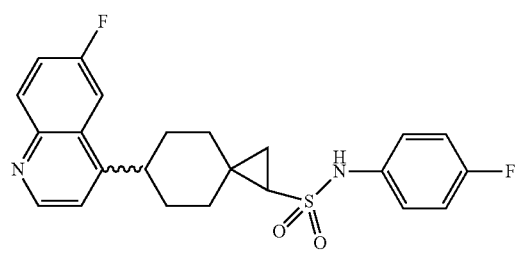 [SMILES: O=S(=O)(Nc1ccc(F)cc1)C1CC12CCC(c1ccnc3ccc(F)cc13)CC2] |
| 16 | 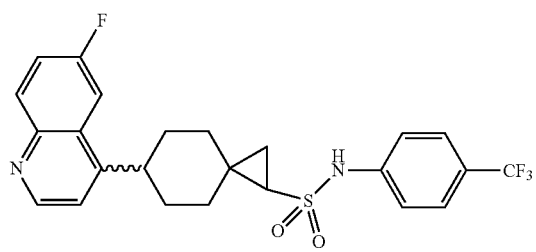 [SMILES: O=S(=O)(Nc1ccc(C(F)(F)F)cc1)C1CC12CCC(c1ccnc3ccc(F)cc13)CC2] |
| 17 | 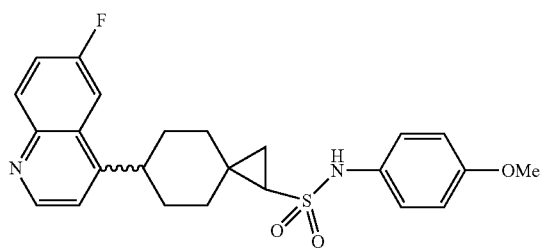 [SMILES: COc1ccc(NS(=O)(=O)C2CC23CCC(c2ccnc4ccc(F)cc24)CC3)cc1] |
| 18 | 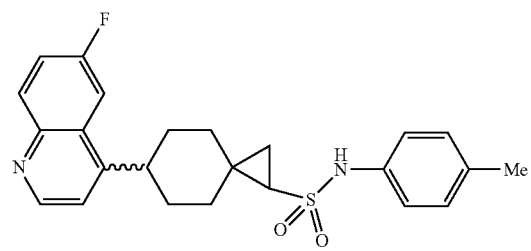 [SMILES: Cc1ccc(NS(=O)(=O)C2CC23CCC(c2ccnc4ccc(F)cc24)CC3)cc1] |
| 19 | 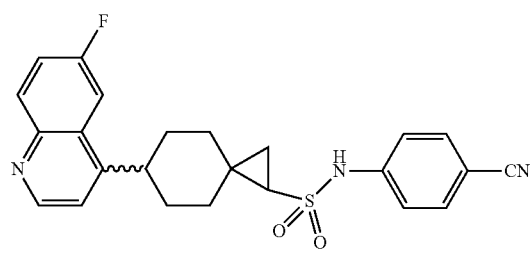 [SMILES: N#Cc1ccc(NS(=O)(=O)C2CC23CCC(c2ccnc4ccc(F)cc24)CC3)cc1] |

-continued
| NO. | Compound structure |
|---|---|
| 20 | 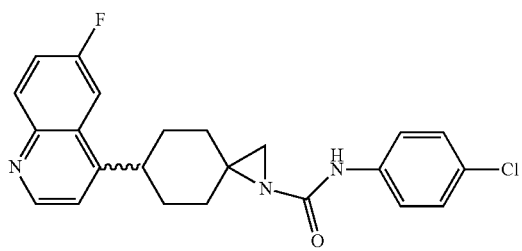 [SMILES: O=C(Nc1ccc(Cl)cc1)N1CC12CCC(c1ccnc3ccc(F)cc13)CC2] |
| 21 | 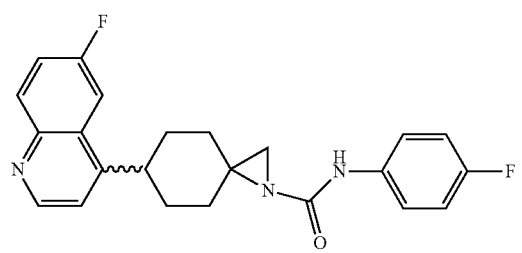 [SMILES: O=C(Nc1ccc(F)cc1)N1CC12CCC(c1ccnc3ccc(F)cc13)CC2] |
| 22 | 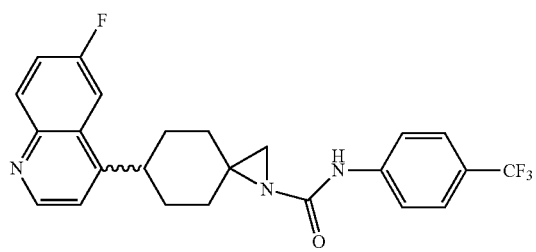 [SMILES: O=C(Nc1ccc(C(F)(F)F)cc1)N1CC12CCC(c1ccnc3ccc(F)cc13)CC2] |
| 23 | 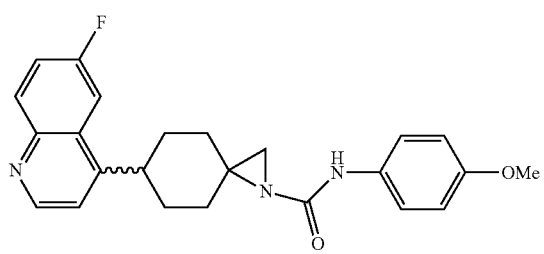 [SMILES: COc1ccc(NC(=O)N2CC23CCC(c2ccnc4ccc(F)cc24)CC3)cc1] |
| 24 | 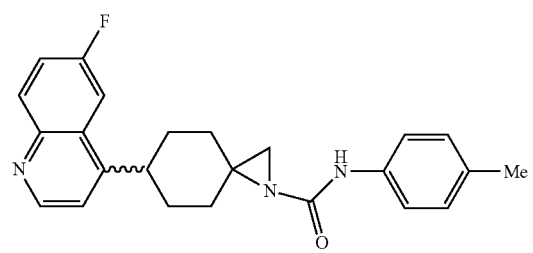 [SMILES: Cc1ccc(NC(=O)N2CC23CCC(c2ccnc4ccc(F)cc24)CC3)cc1] |
| 25 | 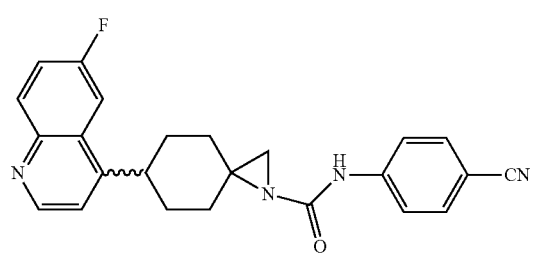 [SMILES: N#Cc1ccc(NC(=O)N2CC23CCC(c2ccnc4ccc(F)cc24)CC3)cc1] |

-continued
| NO. | Compound structure |
|---|---|
| 26 | 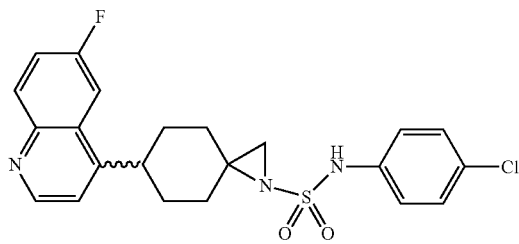 [SMILES: O=S(=O)(Nc1ccc(Cl)cc1)N1CC12CCC(c1ccnc3ccc(F)cc13)CC2] |
| 27 | 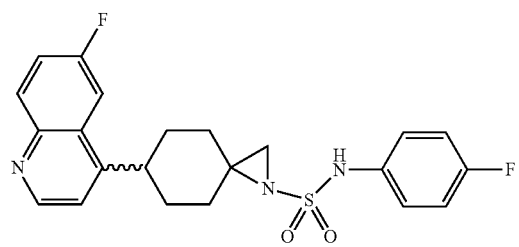 [SMILES: O=S(=O)(Nc1ccc(F)cc1)N1CC12CCC(c1ccnc3ccc(F)cc13)CC2] |
| 28 | 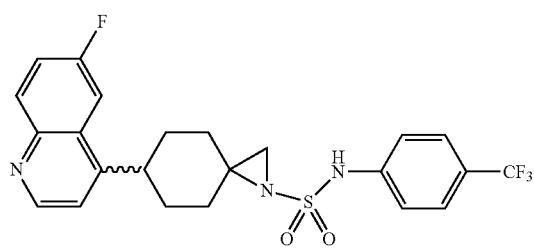 [SMILES: O=S(=O)(Nc1ccc(C(F)(F)F)cc1)N1CC12CCC(c1ccnc3ccc(F)cc13)CC2] |
| 29 | 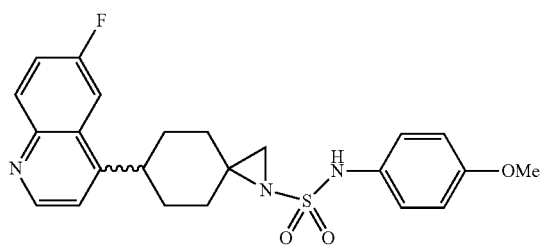 [SMILES: COc1ccc(NS(=O)(=O)N2CC23CCC(c2ccnc4ccc(F)cc24)CC3)cc1] |
| 30 | 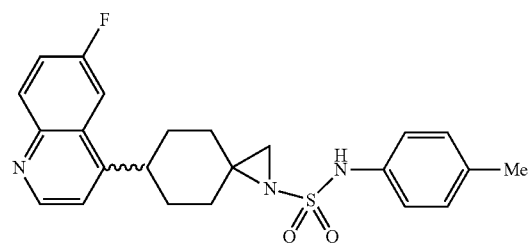 [SMILES: Cc1ccc(NS(=O)(=O)N2CC23CCC(c2ccnc4ccc(F)cc24)CC3)cc1] |
| 31 | 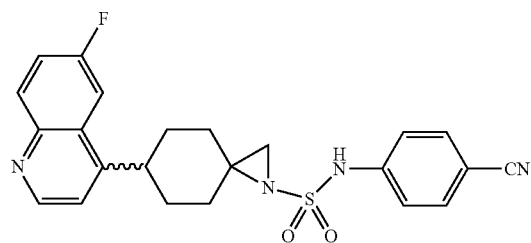 [SMILES: N#Cc1ccc(NS(=O)(=O)N2CC23CCC(c2ccnc4ccc(F)cc24)CC3)cc1] |

-continued
| NO. | Compound structure |
|---|---|
| 32 | 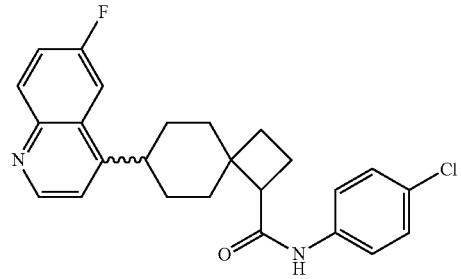 [SMILES: O=C(Nc1ccc(Cl)cc1)C1CCC12CCC(c1ccnc3ccc(F)cc13)CC2] |
| 33 | 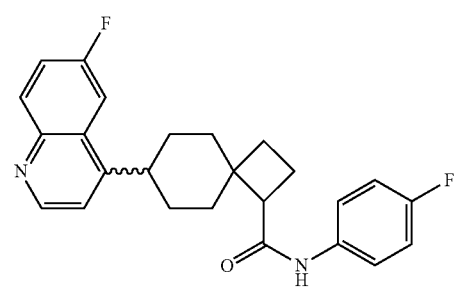 [SMILES: O=C(Nc1ccc(F)cc1)C1CCC12CCC(c1ccnc3ccc(F)cc13)CC2] |
| 34 | 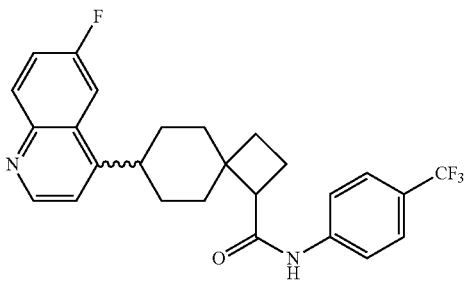 |
| 35 | 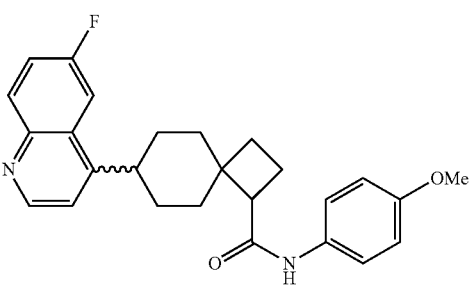 |
| 36 | 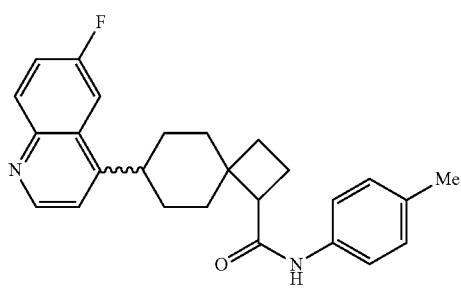 [SMILES: Cc1ccc(NC(=O)C2CCC23CCC(c2ccnc4ccc(F)cc24)CC3)cc1] |

-continued
| NO. | Compound structure |
|---|---|
| 37 | 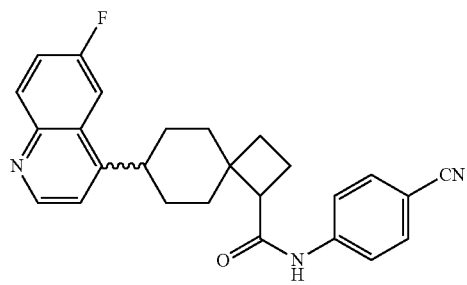 |
| 38 | 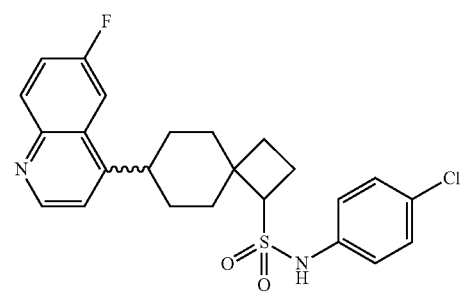 [SMILES: O=S(=O)(Nc1ccc(Cl)cc1)C1CCC12CCC(c1ccnc3ccc(F)cc13)CC2] |
| 39 | 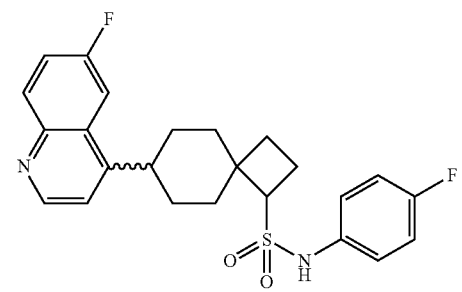 [SMILES: O=S(=O)(Nc1ccc(F)cc1)C1CCC12CCC(c1ccnc3ccc(F)cc13)CC2] |
| 40 | 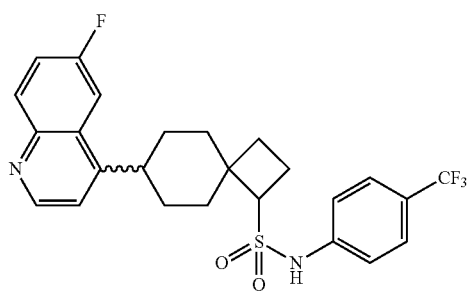 |
| 41 | 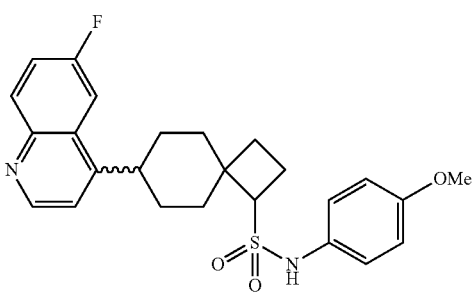 [SMILES: COc1ccc(NS(=O)(=O)C2CCC23CCC(c2ccnc4ccc(F)cc24)CC3)cc1] |

-continued
| NO. | Compound structure |
|---|---|
| 42 | 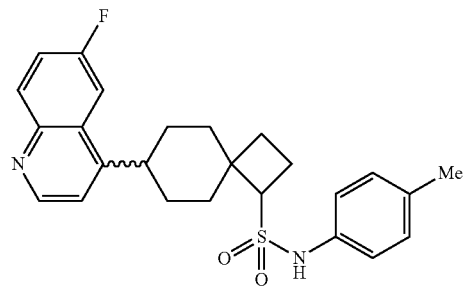 [SMILES: Cc1ccc(NS(=O)(=O)C2CCC23CCC(c2ccnc4ccc(F)cc24)CC3)cc1] |
| 43 | 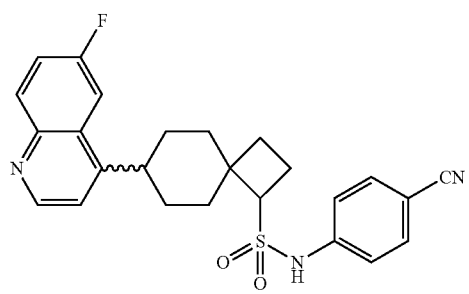 [SMILES: N#Cc1ccc(NS(=O)(=O)C2CCC23CCC(c2ccnc4ccc(F)cc24)CC3)cc1] |
| 44 | 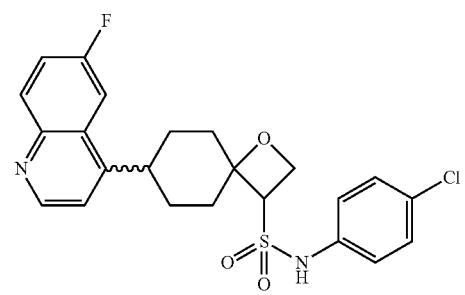 [SMILES: O=S(=O)(Nc1ccc(Cl)cc1)C1COC12CCC(c1ccnc3ccc(F)cc13)CC2] |
| 45 | 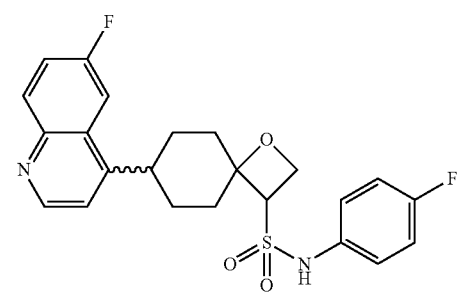 [SMILES: O=S(=O)(Nc1ccc(F)cc1)C1COC12CCC(c1ccnc3ccc(F)cc13)CC2] |
| 46 | 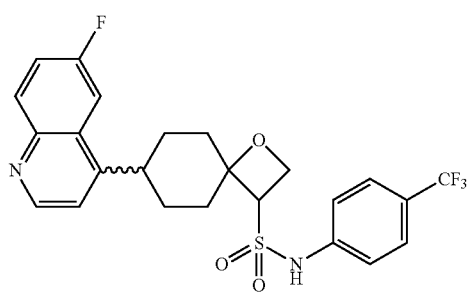 |

| NO. | Compound structure |
|---|---|
| 47 | 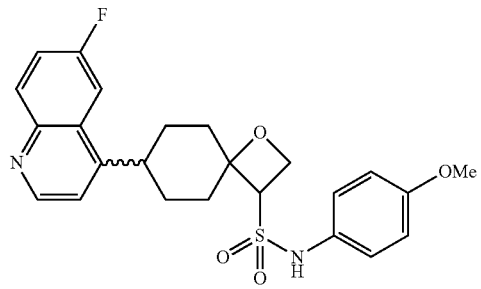 [SMILES: COc1ccc(NS(=O)(=O)C2COC23CCC(c2ccnc4ccc(F)cc24)CC3)cc1] |
| 48 | 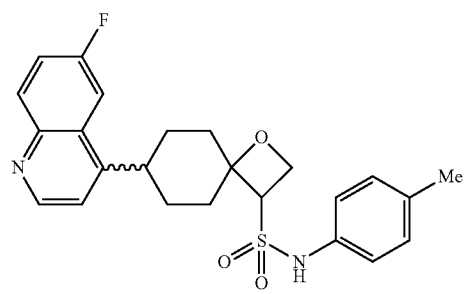 [SMILES: Cc1ccc(NS(=O)(=O)C2COC23CCC(c2ccnc4ccc(F)cc24)CC3)cc1] |
| 49 | 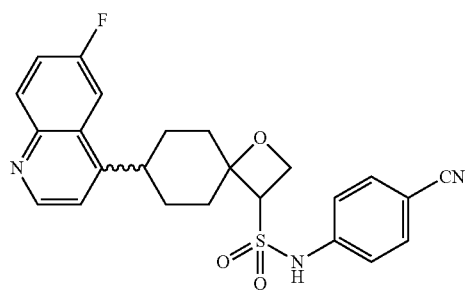 [SMILES: N#Cc1ccc(NS(=O)(=O)C2COC23CCC(c2ccnc4ccc(F)cc24)CC3)cc1] |
| 50 | 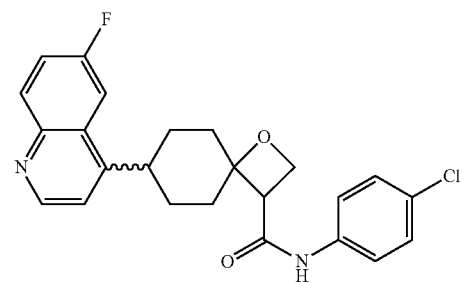 [SMILES: O=C(Nc1ccc(Cl)cc1)C1COC12CCC(c1ccnc3ccc(F)cc13)CC2] |
| 51 | 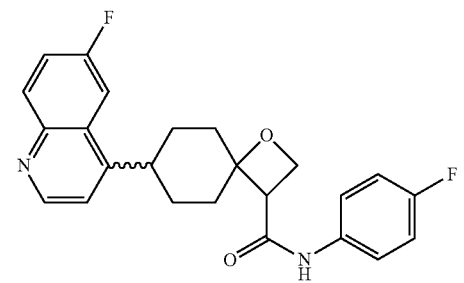 |

| NO. | Compound structure |
|---|---|
| 52 | 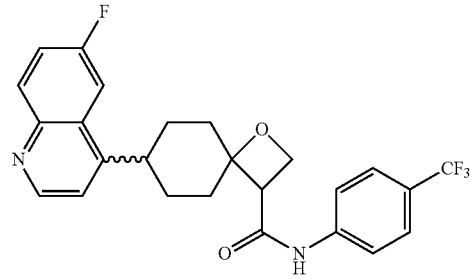 |
| 53 | 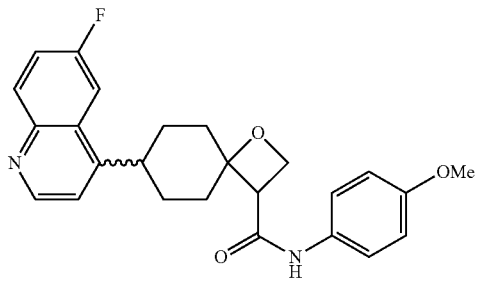 |
| 54 | 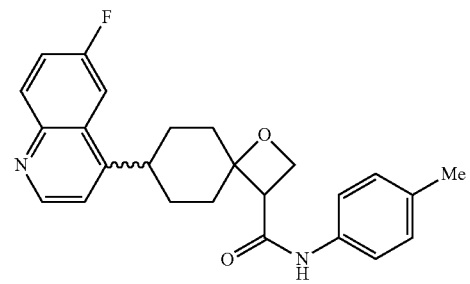 [SMILES: Cc1ccc(NC(=O)C2COC23CCC(c2ccnc4ccc(F)cc24)CC3)cc1] |
| 55 | 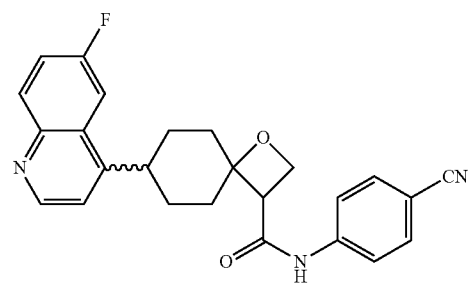 |
| 56 | 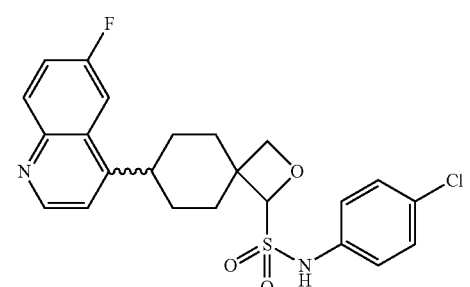 |

| NO. | Compound structure |
|---|---|
| 57 | 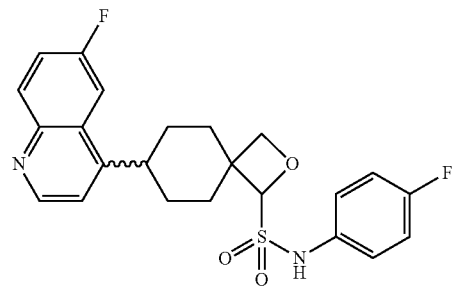 [SMILES: O=S(=O)(Nc1ccc(F)cc1)C1OCC12CCC(c1ccnc3ccc(F)cc13)CC2] |
| 58 | 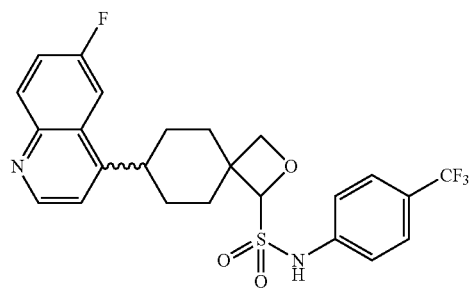 [SMILES: O=S(=O)(Nc1ccc(C(F)(F)F)cc1)C1OCC12CCC(c1ccnc3ccc(F)cc13)CC2] |
| 59 | 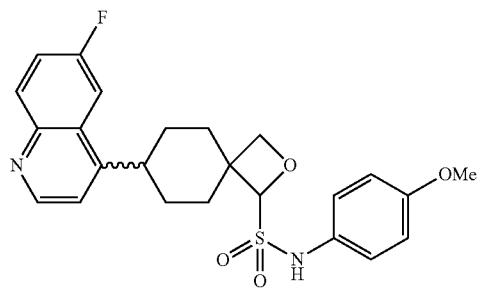 [SMILES: COc1ccc(NS(=O)(=O)C2OCC23CCC(c2ccnc4ccc(F)cc24)CC3)cc1] |
| 60 | 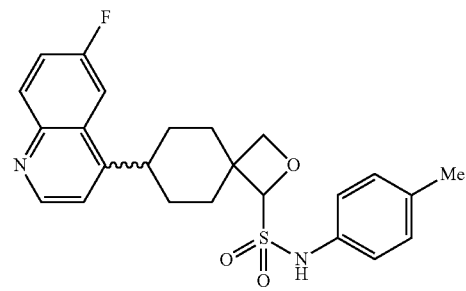 [SMILES: Cc1ccc(NS(=O)(=O)C2OCC23CCC(c2ccnc4ccc(F)cc24)CC3)cc1] |
| 61 | 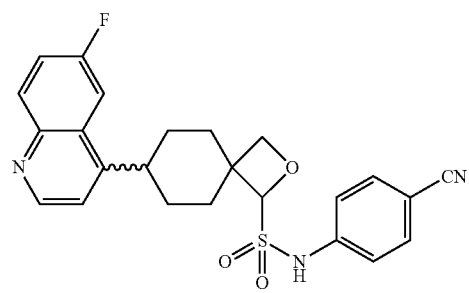 [SMILES: N#Cc1ccc(NS(=O)(=O)C2OCC23CCC(c2ccnc4ccc(F)cc24)CC3)cc1] |

-continued
| NO. | Compound structure |
|---|---|
| 62 | 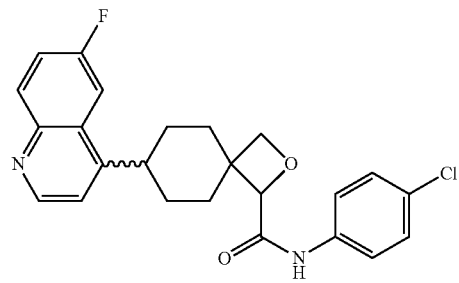 [SMILES: O=C(Nc1ccc(Cl)cc1)C1OCC12CCC(c1ccnc3ccc(F)cc13)CC2] |
| 63 | 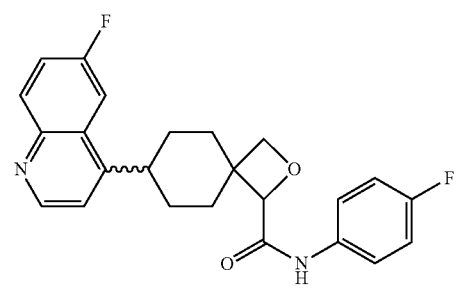 |
| 64 | 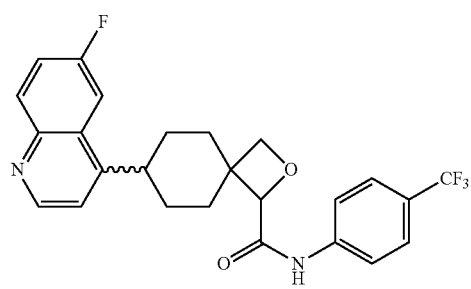 |
| 65 | 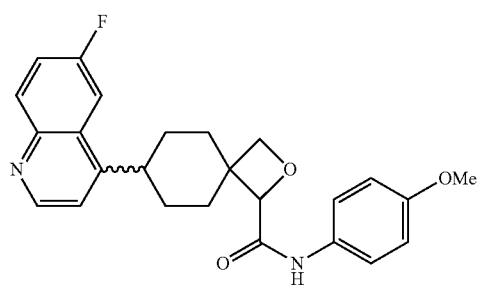 [SMILES: COc1ccc(NC(=O)C2OCC23CCC(c2ccnc4ccc(F)cc24)CC3)cc1] |
| 66 | 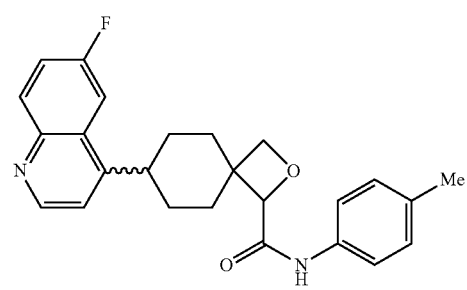 [SMILES: Cc1ccc(NC(=O)C2OCC23CCC(c2ccnc4ccc(F)cc24)CC3)cc1] |

| NO. | Compound structure |
|---|---|
| 67 | 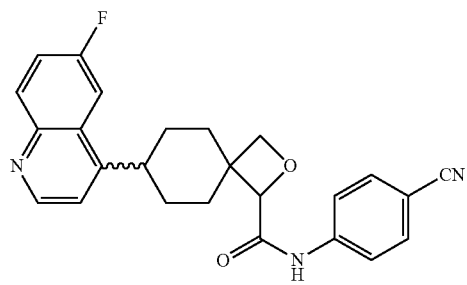 [SMILES: N#Cc1ccc(NC(=O)C2OCC23CCC(c2ccnc4ccc(F)cc24)CC3)cc1] |
| 68 | 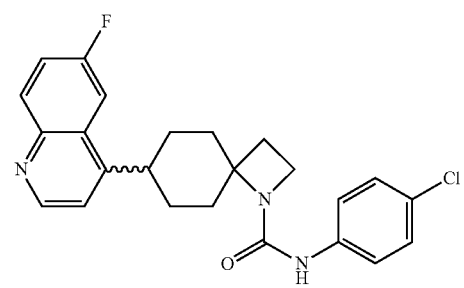 |
| 69 | 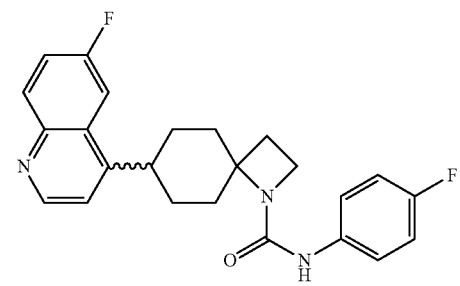 |
| 70 | 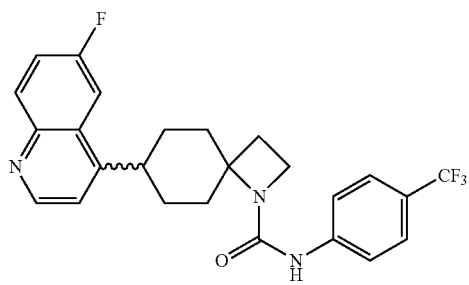 [SMILES: O=C(Nc1ccc(C(F)(F)F)cc1)N1CCC12CCC(c1ccnc3ccc(F)cc13)CC2] |
| 71 | 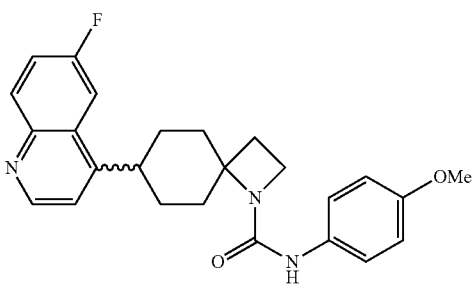 [SMILES: COc1ccc(NC(=O)N2CCC23CCC(c2ccnc4ccc(F)cc24)CC3)cc1] |

| NO. | Compound structure |
|---|---|
| 72 | 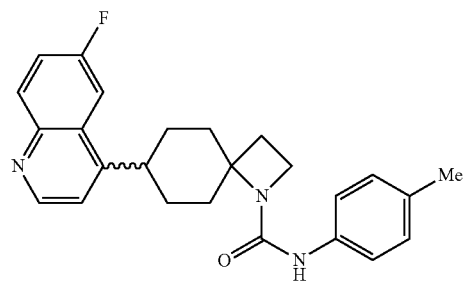 [SMILES: Cc1ccc(NC(=O)N2CCC23CCC(c2ccnc4ccc(F)cc24)CC3)cc1] |
| 73 | 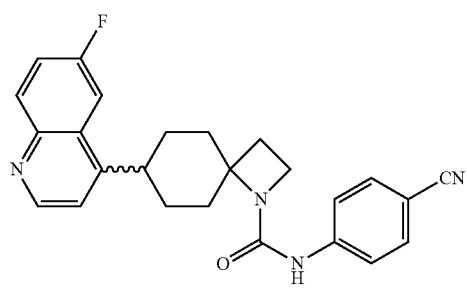 |
| 74 | 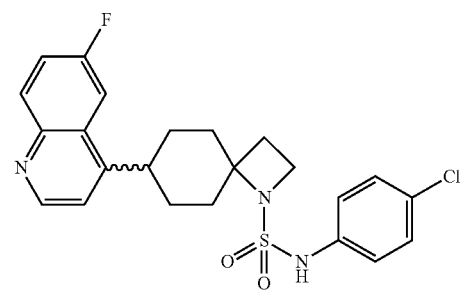 |
| 75 | 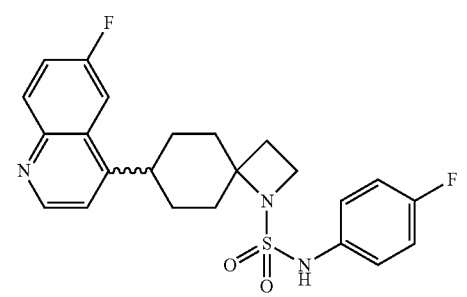 [SMILES: O=S(=O)(Nc1ccc(F)cc1)N1CCC12CCC(c1ccnc3ccc(F)cc13)CC2] |
| 76 | 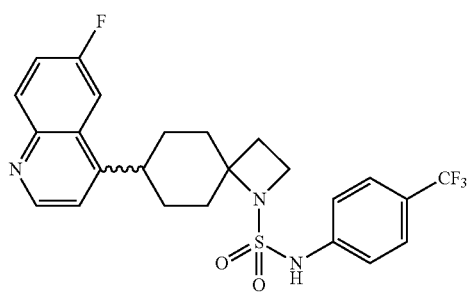 |

| NO. | Compound structure |
|---|---|
| 77 | 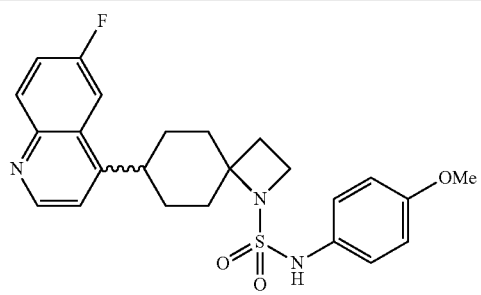 [SMILES: COc1ccc(NS(=O)(=O)N2CCC23CCC(c2ccnc4ccc(F)cc24)CC3)cc1] |
| 78 | 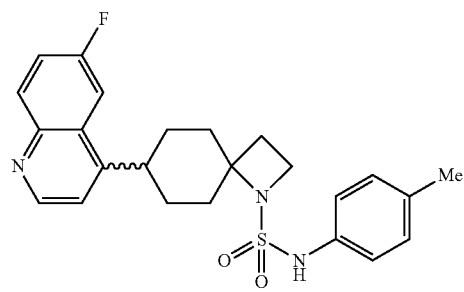 [SMILES: Cc1ccc(NS(=O)(=O)N2CCC23CCC(c2ccnc4ccc(F)cc24)CC3)cc1] |
| 79 | 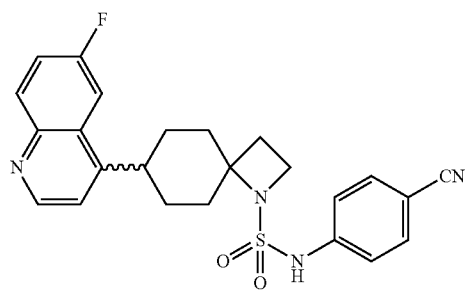 [SMILES: N#Cc1ccc(NS(=O)(=O)N2CCC23CCC(c2ccnc4ccc(F)cc24)CC3)cc1] |
| 80 | 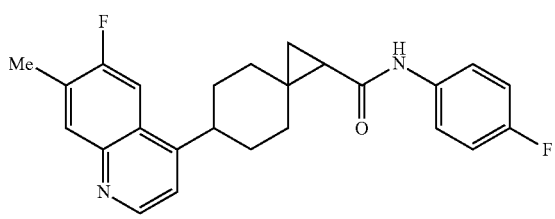 [SMILES: Cc1cc2nccc(C3CCC4(CC3)CC4C(=O)Nc3ccc(F)cc3)c2cc1F] |
| 81 | 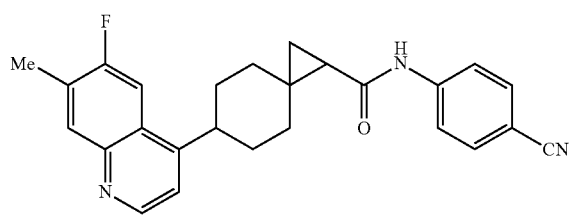 [SMILES: Cc1cc2nccc(C3CCC4(CC3)CC4C(=O)Nc3ccc(C#N)cc3)c2cc1F] |
| 82 | 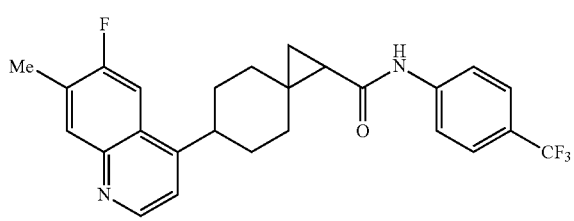 [SMILES: Cc1cc2nccc(C3CCC4(CC3)CC4C(=O)Nc3ccc(C(F)(F)F)cc3)c2cc1F] |

| NO. | Compound structure |
|---|---|
| 83 | 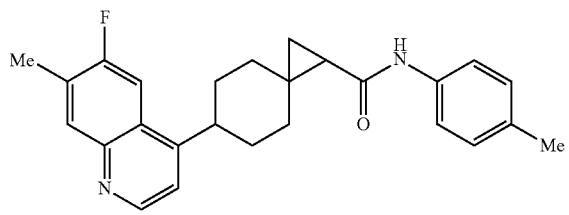 [SMILES: Cc1ccc(NC(=O)C2CC23CCC(c2ccnc4cc(C)c(F)cc24)CC3)cc1] |
| 84 | 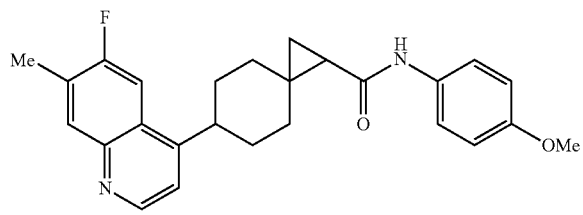 [SMILES: COc1ccc(NC(=O)C2CC23CCC(c2ccnc4cc(C)c(F)cc24)CC3)cc1] |
| 85 | 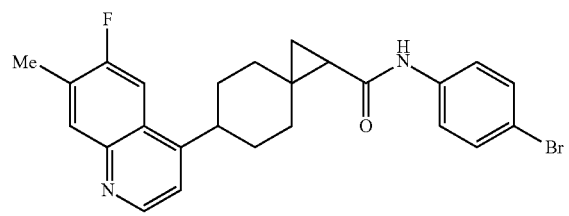 [SMILES: Cc1cc2nccc(C3CCC4(CC3)CC4C(=O)Nc3ccc(Br)cc3)c2cc1F] |
| 86 | 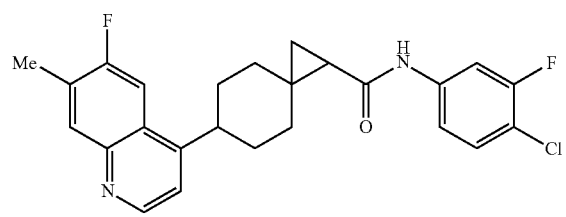 |
| 87 | 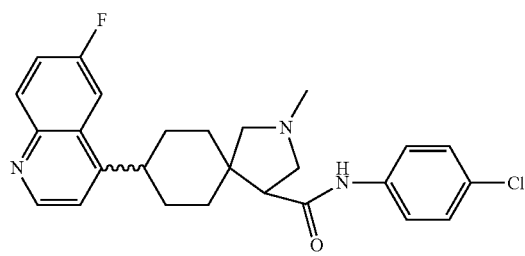 [SMILES: CN1CC(C(=O)Nc2ccc(Cl)cc2)C2(CCC(c3ccnc4ccc(F)cc34)CC2)C1] |
| 88 | 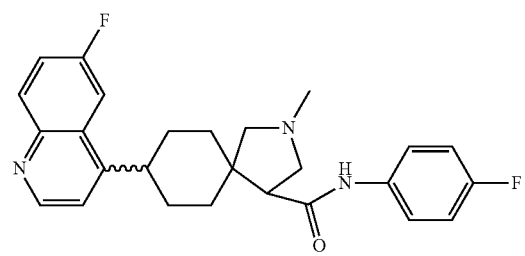 [SMILES: CN1CC(C(=O)Nc2ccc(F)cc2)C2(CCC(c3ccnc4ccc(F)cc34)CC2)C1] |

| NO. | Compound structure |
|---|---|
| 89 | 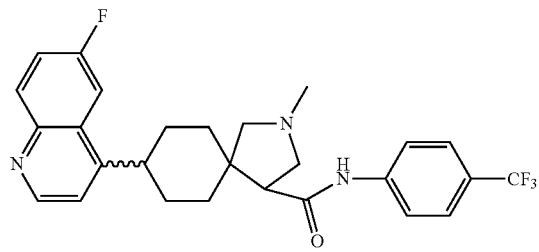 [SMILES: CN1CC(C(=O)Nc2ccc(C(F)(F)F)cc2)C2(CCC(c3ccnc4ccc(F)cc34)CC2)C1] |
| 90 | 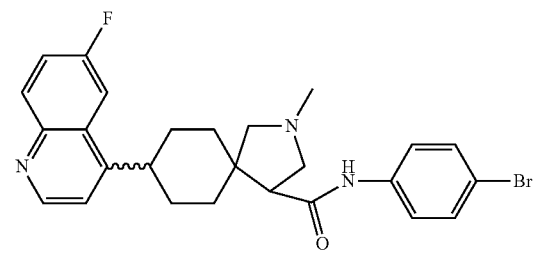 [SMILES: CN1CC(C(=O)Nc2ccc(Br)cc2)C2(CCC(c3ccnc4ccc(F)cc34)CC2)C1] |
| 91 | 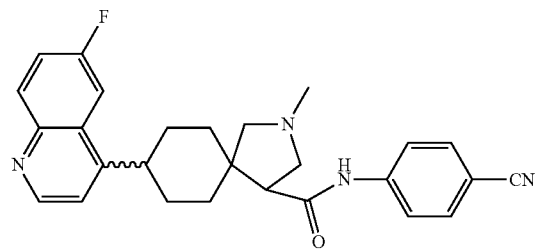 [SMILES: CN1CC(C(=O)Nc2ccc(C#N)cc2)C2(CCC(c3ccnc4ccc(F)cc34)CC2)C1] |
| 92 | 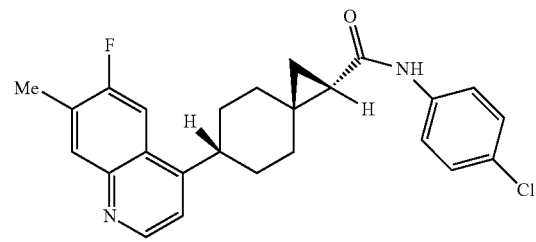 [SMILES: Cc1cc2nccc([C@H]3CC[C@@]4(CC3)C[C@@H]4C(=O)Nc3ccc(Cl)cc3)c2cc1F] |
| 93 | 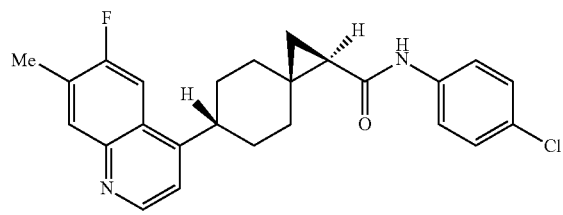 [SMILES: Cc1cc2nccc([C@H]3CC[C@@]4(CC3)C[C@H]4C(=O)Nc3ccc(Cl)cc3)c2cc1F] |
| 94 | 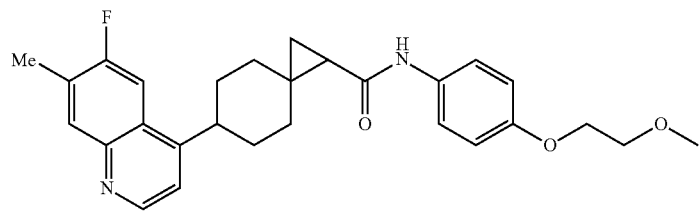 [SMILES: COCCOc1ccc(NC(=O)C2CC23CCC(c2ccnc4cc(C)c(F)cc24)CC3)cc1] |

| NO. | Compound structure |
|---|---|
| 95 | 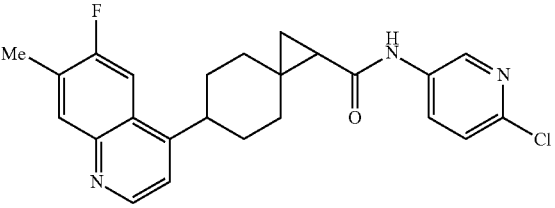 [SMILES: Cc1cc2nccc(C3CCC4(CC3)CC4C(=O)Nc3ccc(Cl)nc3)c2cc1F] |
| 96 | 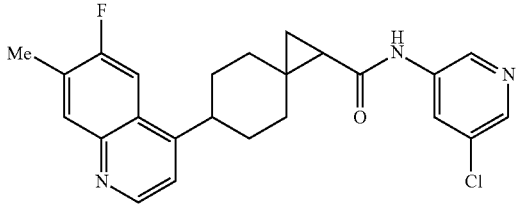 [SMILES: Cc1cc2nccc(C3CCC4(CC3)CC4C(=O)Nc3cncc(Cl)c3)c2cc1F] |
| 97 | 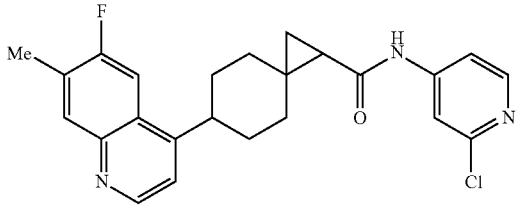 [SMILES: Cc1cc2nccc(C3CCC4(CC3)CC4C(=O)Nc3ccnc(Cl)c3)c2cc1F] |
| 98 | 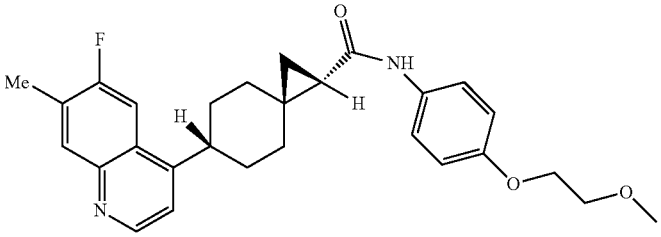 [SMILES: COCCOc1ccc(NC(=O)[C@H]2C[C@]23CC[C@H](c2ccnc4cc(C)c(F)cc42)CC3)cc1] |
| 99 | 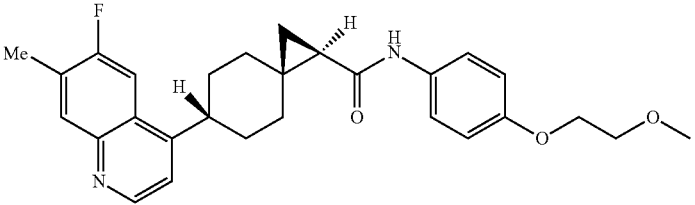 [SMILES: COCCOc1ccc(NC(=O)[C@@H]2C[C@]23CC[C@H](c2ccnc4cc(C)c(F)cc42)CC3)cc1] |
| 100 | 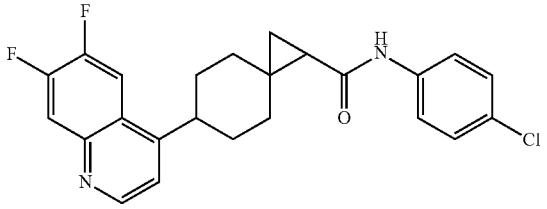 [SMILES: O=C(Nc1ccc(Cl)cc1)C1CC12CCC(c1ccnc3cc(F)c(F)cc13)CC2] |
| 101 | 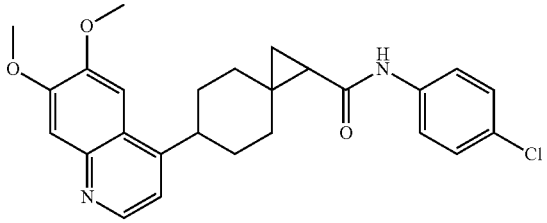 [SMILES: COc1cc2nccc(C3CCC4(CC3)CC4C(=O)Nc3ccc(Cl)cc3)c2cc1OC] |

-continued

| NO. | Compound structure |
|---|---|
| 102 | 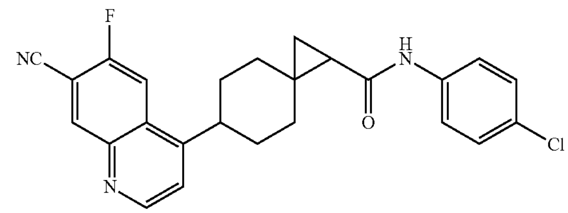 [SMILES: N#Cc1cc2nccc(C3CCC4(CC3)CC4C(=O)Nc3ccc(Cl)cc3)c2cc1F] |
| 103 | 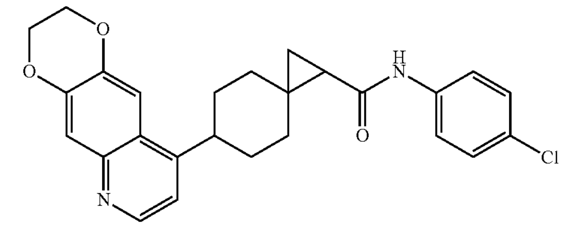 [SMILES: O=C(Nc1ccc(Cl)cc1)C1CC12CCC(c1ccnc3cc4c(cc13)OCCO4)CC2] |
| 104 | 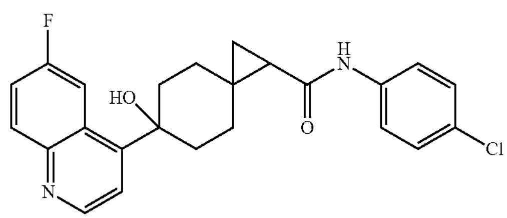 [SMILES: O=C(Nc1ccc(Cl)cc1)C1CC12CCC(O)(c1ccnc3ccc(F)cc13)CC2] |
| 105 | 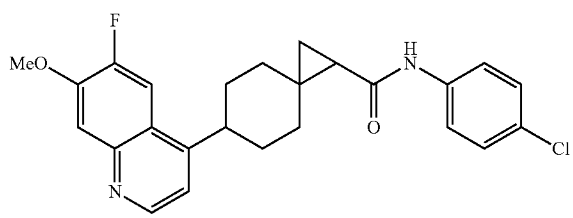 [SMILES: COc1cc2nccc(C3CCC4(CC3)CC4C(=O)Nc3ccc(Cl)cc3)c2cc1F] |
| 106 | 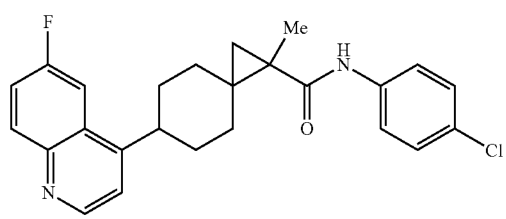 [SMILES: CC1(C(=O)Nc2ccc(Cl)cc2)CC12CCC(c1ccnc3ccc(F)cc13)CC2] |
| 107 | 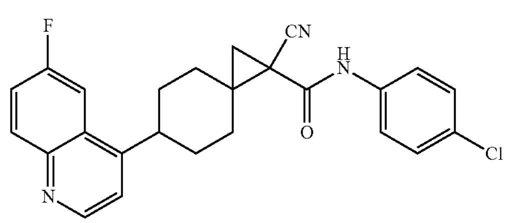 [SMILES: N#CC1(C(=O)Nc2ccc(Cl)cc2)CC12CCC(c1ccnc3ccc(F)cc13)CC2] |
| 108 | 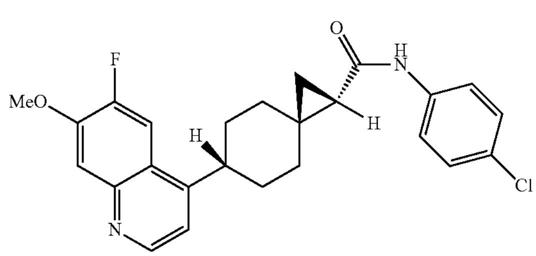 [SMILES: COc1cc2nccc([C@H]3CC[C@@]4(CC3)C[C@@H]4C(=O)Nc3ccc(Cl)cc3)c2cc1F] |

| NO. | Compound structure |
|---|---|
| 109 | (structure) |
| 110 | (structure) |
| 111 | (structure) |
| 112 | (structure) |
| 113 | (structure) |
| 114 | (structure) |
| 115 | (structure) |

Synthesis

The compounds of the present invention can be synthesized by known procedures with reference to the following description. All purchased solvents and reagents are used without treatment. All synthesized compounds can be analyzed and verified by, but not limited to, the following methods: LCMS (liquid chromatography mass spectrometry, liquid phase mass spectrometry) and NMR (nuclear magnetic resonance, nuclear magnetic resonance). Nuclear magnetic resonance (NMR) is measured by Bruker AVANCE-500 nuclear magnetic instrument. The deuterated solvent used in the measurement is deuterated dimethyl sulfoxide ($d_6$-DMSO), deuterated chloroform ($CDCl_3$), tetramethylsilane (TMS) as Internal standard. The following abbreviations represent various types of splitting peaks: singlet (s), doublet (d), triplet (t), multiplet (m), broad (br). Thermo Fisher-MSQ Plus liquid-mass spectrometry was used for the determination of mass spectrometry (MS). General synthetic analysis and examples are described as follows:

Example 1

N-(4-chlorophenyl)-6-(6-fluoroquinolin-4-yl)spiro[2.5]octane-1-carboxamide

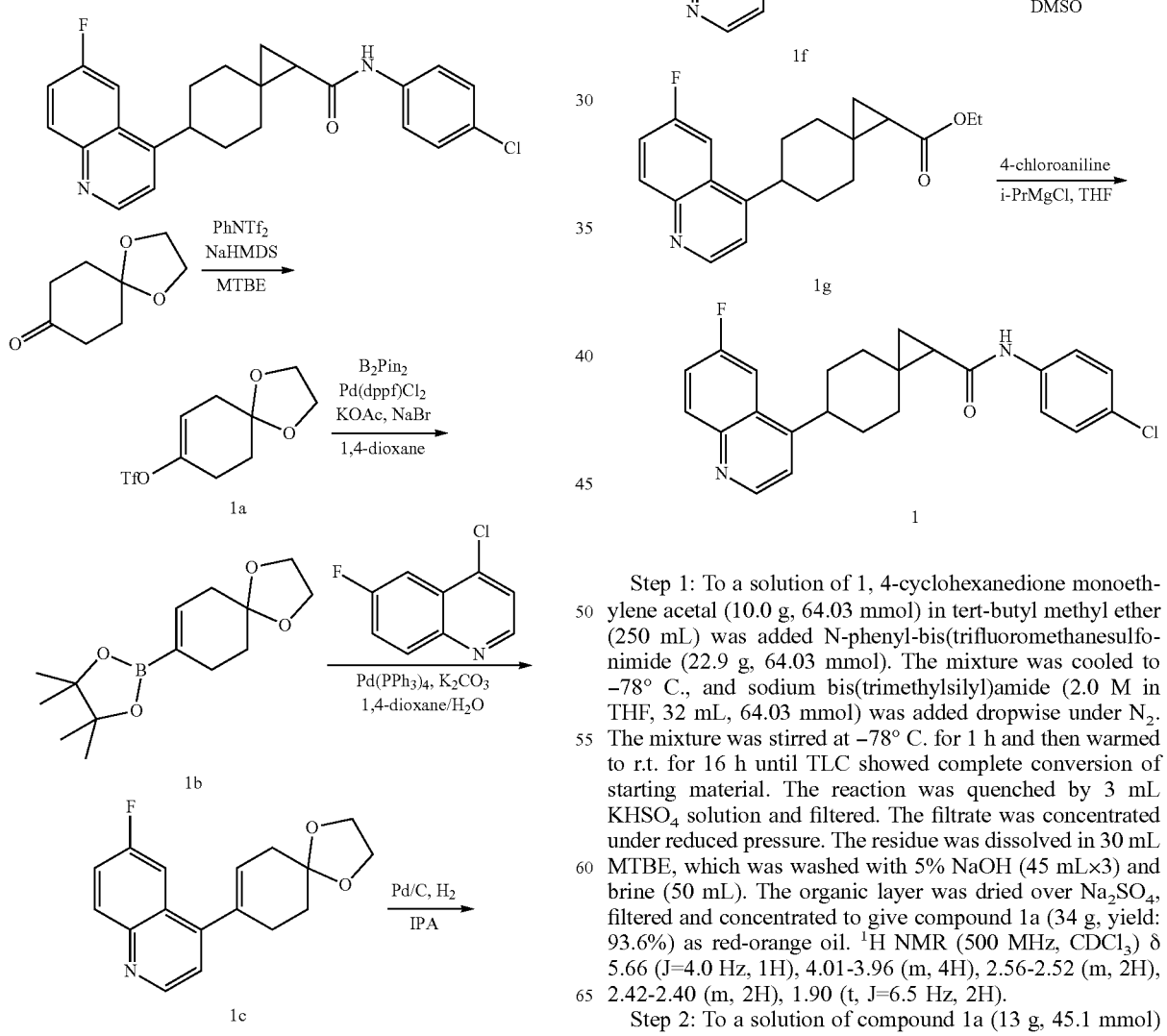

Step 1: To a solution of 1, 4-cyclohexanedione monoethylene acetal (10.0 g, 64.03 mmol) in tert-butyl methyl ether (250 mL) was added N-phenyl-bis(trifluoromethanesulfonimide (22.9 g, 64.03 mmol). The mixture was cooled to −78° C., and sodium bis(trimethylsilyl)amide (2.0 M in THF, 32 mL, 64.03 mmol) was added dropwise under $N_2$. The mixture was stirred at −78° C. for 1 h and then warmed to r.t. for 16 h until TLC showed complete conversion of starting material. The reaction was quenched by 3 mL $KHSO_4$ solution and filtered. The filtrate was concentrated under reduced pressure. The residue was dissolved in 30 mL MTBE, which was washed with 5% NaOH (45 mL×3) and brine (50 mL). The organic layer was dried over $Na_2SO_4$, filtered and concentrated to give compound 1a (34 g, yield: 93.6%) as red-orange oil. $^1$H NMR (500 MHz, $CDCl_3$) δ 5.66 (J=4.0 Hz, 1H), 4.01-3.96 (m, 4H), 2.56-2.52 (m, 2H), 2.42-2.40 (m, 2H), 1.90 (t, J=6.5 Hz, 2H).

Step 2: To a solution of compound 1a (13 g, 45.1 mmol) in dioxane (100 mL) were added bis(pinacolato)diboron (14.9 g, 58.64 mmol), KOAc (13.3 g, 135.3 mmol) and Pd(dppf)Cl₂ (1.65 g, 2.26 mmol). The reaction mixture was stirred at 100° C. under N₂ for 16 h. The mixture was concentrated under reduced pressure. The residue was suspended in EA and filtered over a pad of celite. The filtrate was concentrated and purified by column chromatography on silica gel to afford compound 1b (7.6 g, yield: 63%) as a pale-yellow solid. ¹H NMR (500 MHz, CDCl₃) δ 6.48-6.45 (m, 1H), 3.98 (s, 4H), 2.40-2.34 (m, 4H), 1.73 (t, J=6.5 Hz, 2H), 1.25 (s, 12H).

Step 3: To a solution of compound 1b (5.7 g, 21.48 mmol) in dioxane (60 mL) and water (15 mL) were added 4-chloro-6-fluoroquinoline (3.0 g, 16.53 mmol), potassium carbonate (6.8 g, 49.56 mmol), and tetrakis(triphenylphosphine) palladium(0) (954 mg, 0.83 mmol). The reaction mixture was stirred at 100° C. under N₂ for 16 h. The mixture was concentrated under reduced pressure. The residue was diluted with H₂O and extracted with EtOAc. The organic layer was concentrated. The residue was purified by column chromatography on silica gel to afford compound 1c (2.42 g, yield 51%) as pale-yellow oil. MS (ESI): m/z 286.1 (M+H)⁺. ¹H NMR (500 MHz, CDCl₃) δ 8.81 (d, J=4.5 Hz, 1H), 8.15 (dd, J=9.0, 5.5 Hz, 1H), 7.65 (dd, J=10.0, 2.5 Hz, 1H), 7.49 (td, J=9.0, 2.5 Hz, 1H), 7.26 (d, J=4.5 Hz, 1H), 5.77 (t, J=3.5 Hz, 1H), 4.08-40.6 (m, 4H), 2.65-2.60 (m, 2H), 2.56-2.53 (m, 2H), 2.00 (t, J=6.5 Hz, 2H).

Step 4: To a solution of compound 1c (2.42 g, 8.49 mmol) in isopropyl alcohol (45 mL) was added 10% w/w palladium on carbon (300 mg). The mixture was stirred at 55° C. under hydrogen atmosphere for 16 h. The reaction was filtered over a pad of celite. The filtrate was concentrated to give compound 1d (2.04 g, yield: 84%) as slurry oil, which was used to the next step directly. MS (ESI): m/z 288.1 (M+H)⁺.

Step 5: To a solution of compound 1d (2.04 g, 7.11 mmol) in acetone (36 mL) was added HCl (4N in water, 9 mL, 36 mmol) and the mixture was stirred at 45° C. for 16 h. The organic volatiles were removed and the remaining aqueous solution was adjusted to pH=9 by 6N NaOH solution. The mixture was extracted with EtOAc three times. The combined organic layers were washed with brine, dried over Na₂SO₄, filtered and concentrated under reduced pressure. The residue was purified by column chromatography on silica gel to give compound 1e (1.17 g, yield 67%) as a pale-yellow solid. MS (ESI): m/z 244.3 (M+H)⁺. ¹H NMR (500 MHz, CDCl₃) δ 8.85 (d, J=4.5 Hz, 1H), 8.22 (dd, J=9.0, 5.5 Hz, 1H), 7.74 (dd, J=10.0, 2.5 Hz, 1H), 7.57-7.50 (m, 1H), 7.33 (d, J=4.5 Hz, 1H), 3.74-3.66 (m, 1H), 2.72-2.58 (m, 4H), 2.41-2.34 (m, 2H), 2.11-2.00 (m, 2H).

Step 6: To a solution of triethyl phosphonoacetate (968 mg, 4.32 mmol) in dry THF (16 mL) at 0° C., sodium tert-butoxide (415 mg, 4.32 mmol) was added. After 10 min, a solution of compound 1e (1 g, 4.12 mmol) in THF (4 mL) was added to the above mixture and the resulting reaction mixture was stirred for 2 h. The reaction was quenched by H₂O, extracted with EtOAc three times. The combined organic layers were washed with brine (20 mL), dried over Na₂SO₄, filtered and concentrated under reduced pressure. The residue was purified by column chromatography on silica gel to give compound 1f (1.18 g, yield: 92%) as a white solid. MS (ESI): m/z 314.0 (M+H)⁺. ¹H NMR (500 MHz, CDCl₃) δ 8.81 (d, J=4.5 Hz, 1H), 8.17 (dd, J=9.0, 5.5 Hz, 1H), 7.72 (dd, J=10.0, 2.5 Hz, 1H), 7.53-7.47 (m, 1H), 7.28 (d, J=4.5 Hz, 1H), 5.75 (s, 1H), 4.19 (q, J=7.0 Hz, 2H), 3.52-3.42 (m, 1H), 2.54-2.48 (m, 2H), 2.26-2.11 (m, 4H), 1.80-1.68 (m, 2H), 1.30 (t, J=7.0 Hz, 3H).

Step 7: To a suspension of NaH (60% w/w in mineral oil, 383 mg, 9.57 mmol) in DMSO (15 mL) was added trimethylsulfoxonium iodide (2.11 g, 9.57 mmol). After the mixture was stirred at r.t. for 1.5 h, a solution of compound 1f (1.0 g, 3.19 mmol) in DMSO (5 mL) was added to the above mixture and the resulting reaction mixture was stirred at r.t. for 16 h. The mixture was quenched by H₂O and extracted with EtOAc. The organic layer was concentrated and the residue was purified by column chromatography on silica gel to give compound 1g (820 mg, yield: 78%) as colorless oil. MS (ESI): m/z 328.1 (M+H)⁺. ¹H NMR (500 MHz, CDCl₃) δ 8.83 (d, J=4.5 Hz, 1H), 8.24 (dd, J=9.0, 5.5 Hz, 1H), 7.71 (dd, J=10.0, 2.5 Hz, 1H), 7.55-7.49 (m, 1H), 7.35 (d, J=4.5 Hz, 1H), 4.19 (q, J=7.0 Hz, 2H), 3.32-3.24 (m, 1H), 2.17 (td, J=13.0, 3.5 Hz, 1H), 2.07-1.90 (m, 4H), 1.87-1.78 (m, 1H), 1.58 (dd, J=8.0, 5.5 Hz, 1H), 1.46-1.37 (m, 1H), 1.30 (t, J=7.0 Hz, 3H), 1.28-1.24 (m, 2H), 1.16-1.11 (m, 1H), 1.00 (dd, J=8.0, 4.5 Hz, 1H).

Step 8: To a mixture of 4-chloroaniline (94 mg, 0.73 mmol) in dry THF (5 mL) at 0° C., isopropylmagnesium chloride solution (2.0 M in THF, 0.4 mL, 0.73 mmol) was added dropwise. After the mixture was stirred at r.t. for 5 min, a solution of compound 1g (60 mg, 0.18 mmol) in dry THF (2 mL) was added dropwise. The resulting mixture was stirred at r.t. for 16 h. The reaction was quenched by aq. NH₄Cl solution. The mixture was extracted with ethyl acetate three times and the combined organic layers were dried over Na₂SO₄, filtered and concentrated under reduced pressure. The residue was purified by Prep-HPLC to give compound 1 (16.04 mg, yield: 21%) as a white solid. MS (ESI): m/z 408.9 (M+H)⁺. ¹H NMR (500 MHz, d₆-DMSO) δ 10.37 (s, 1H), 8.81 (s, 1H), 8.11-8.05 (m, 1H), 8.02 (d, J=11.0 Hz, 1H), 7.69-7.63 (m, 3H), 7.38-7.31 (m, 3H), 3.48-3.40 (m, 1H), 2.20 (t, J=12.0 Hz, 1H), 1.97-1.84 (m, 4H), 1.78 (d, J=12.5 Hz, 1H), 1.72 (t, J=6.5 Hz, 1H), 1.35-1.26 (m, 1H), 1.17-1.08 (m, 2H), 0.96-0.90 (m, 1H).

Example 2

N-(4-fluorophenyl)-6-(6-fluoroquinolin-4-yl)spiro[2.5]octane-1-carboxamide

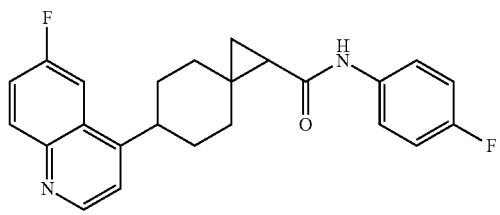 [SMILES: O=C(Nc1ccc(F)cc1)C1CC12CCC(c1ccnc3ccc(F)cc13)CC2]

Compound 2 was prepared using the similar procedures as described for compound 1 using 4-fluoro aniline to replace 4-chloro aniline. MS (ESI): m/z 393.3 (M+H)⁺. ¹H NMR (500 MHz, d₆-DMSO) δ 10.28 (s, 1H), 8.81 (s, 1H), 8.10-8.05 (m, 1H), 8.03 (d, J=11.0 Hz, 1H), 7.69-7.60 (m, 3H), 7.37 (s, 1H), 7.13 (t, J=8.0 Hz, 2H), 3.49-3.40 (m, 1H), 2.20 (t, J=12.0 Hz, 1H), 1.98-1.85 (m, 4H), 1.78 (d, J=11.0 Hz, 1H), 1.72 (t, J=6.5 Hz, 1H), 1.37-1.28 (m, 1H), 1.17-1.07 (m, 2H), 0.94-0.89 (m, 1H).

Example 3

N-(4-chlorobenzyl)-6-(6-fluoroquinolin-4-yl)spiro[2.5]octane-1-carboxamide

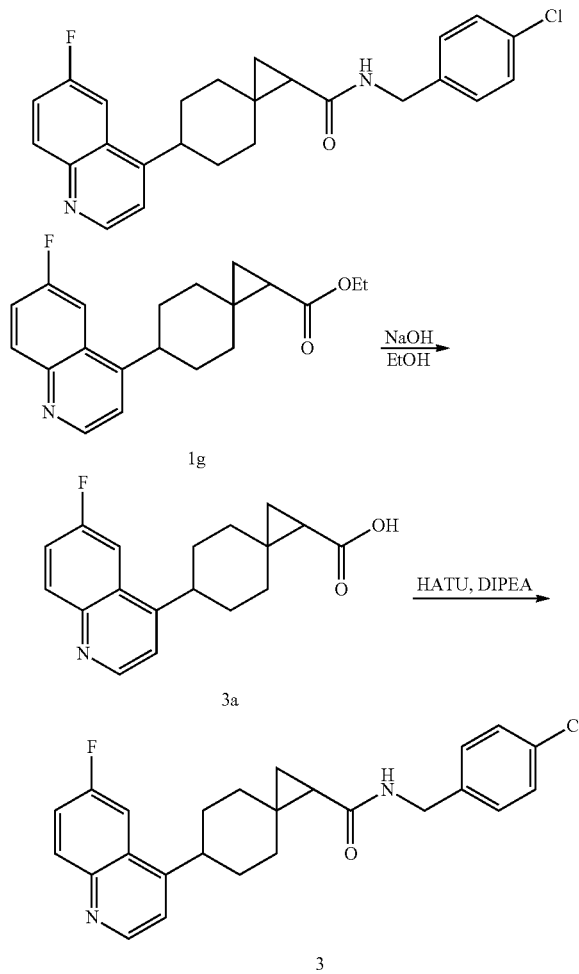

Step 1: To a solution of compound 1g (200 mg, 0.61 mmol) in ethanol (10 mL) was added NaOH (2N in water, 4 mL, 8 mmol) and the mixture was stirred at 50° C. for 2 h. The mixture was cooled to r.t. and adjusted to pH=1 by 4N HCl solution. The mixture was extracted with EtOAc three times. The combined organic layers were dried over Na$_2$SO$_4$, filtered and concentrated under reduced pressure. The residue was purified by Prep-TLC to give compound 3a (150 mg, yield 83%) as a white solid. MS (ESI): m/z 300.0 (M+H)$^+$. $^1$H NMR (500 MHz, d$_6$-DMSO) δ 12.02 (br, 1H), 8.83 (d, J=4.5 Hz, 1H), 8.10 (dd, J=9.0, 5.5 Hz, 1H), 8.03 (dd, J=10.0, 2.5 Hz, 1H), 7.71-7.64 (m, 1H), 7.38 (d, J=4.5 Hz, 1H), 3.48-3.41 (m, 1H), 2.21-2.13 (m, 1H), 2.01-1.80 (m, 4H), 1.75-1.65 (m, 1H), 1.51 (dd, J=8.0, 5.5 Hz, 1H), 1.38-1.32 (m, 1H), 1.11-1.05 (m, 1H), 1.04-0.99 (m, 1H), 0.95 (dd, J=7.5, 4.0 Hz, 1H).

Step 2: To a solution of compound 3a (40 mg, 0.13 mmol) in DMF (5 mL) were added DIPEA (52 mg, 0.39 mmol) and HATU (61 mg, 0.16 mmol) and the mixture was stirred at r.t. for 30 min. 4-chlorobenzylamine (57 mg, 0.39 mmol) was added to the above mixture and the resulting reaction mixture was stirred at r.t. for 2 h. The mixture was quenched by H$_2$O (20 mL) and extracted with EtOAc three times. The combined organic layers were dried over Na$_2$SO$_4$, filtered and concentrated under reduced pressure. The residue was purified by Prep-HPLC to give compound 3 (6.34 mg, yield 11%) as a white solid. MS (ESI): m/z 423.4 (M+H)$^+$. $^1$H NMR (500 MHz, d$_6$-DMSO) δ 8.81 (s, 1H), 8.68 (s, 1H), 8.12-8.07 (m, 1H), 8.00 (d, J=11.0 Hz, 1H), 7.67 (t, J=8.5 Hz, 1H), 7.36-7.31 (m, 4H), 7.14 (s, 1H), 4.44 (dd, J=15.0, 6.5 Hz, 1H), 4.18 (dd, J=15.0, 5.0 Hz, 1H), 3.42-3.34 (m, 1H), 2.13 (t, J=12.5 Hz, 1H), 1.86-1.74 (m, 4H), 1.63 (d, J=12.5 Hz, 1H), 1.54-1.48 (m, 1H), 1.25-1.15 (m, 1H), 1.08-0.96 (m, 2H), 0.82-0.76 (m, 1H).

Example 4

N-(4-chlorophenethyl)-6-(6-fluoroquinolin-4-yl)spiro[2.5]octane-1-carboxamide

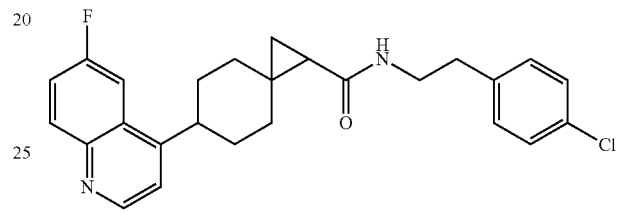

Compound 4 was prepared using the similar procedures as described for compound 3 using 4-chlorophenethylamine to replace 4-chlorobenzylamine. MS (ESI): m/z 437.4 (M+H)$^+$. $^1$H NMR (500 MHz, d$_6$-DMSO) δ 8.84 (d, J=4.5 Hz, 1H), 8.19 (t, J=5.5 Hz, 1H), 8.12-8.07 (m, 1H), 7.99 (d, J=11.0 Hz, 1H), 7.67 (t, J=8.5 Hz, 1H), 7.27 (d, J=4.1 Hz, 1H), 7.25-7.21 (m, 4H), 3.49-3.42 (m, 1H), 3.30-3.22 (m, 2H), 2.74 (t, J=6.5 Hz, 2H), 2.11 (t, J=12.5 Hz, 1H), 1.85-1.75 (m, 4H), 1.67 (d, J=12.5 Hz, 1H), 1.46-1.41 (m, 1H), 1.26-1.14 (m, 1H), 1.03-0.95 (m, 2H), 0.75-0.70 (m, 1H).

Example 5

6-(6-fluoroquinolin-4-yl)-N-(4-(trifluoromethyl)phenyl)spiro[2.5]octane-1-carboxamide -continued

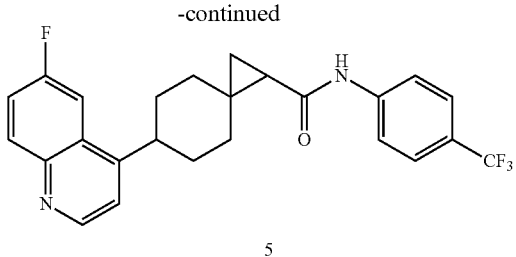

5

To a solution of compound 3a (40 mg, 0.13 mmol) in EA (5 mL) were subsequently added pyridine (32 mg, 0.39 mmol) and 2,4,6-Tripropyl-1,3,5,2,4,6-Trioxatriphosphorinane-2,4,6-Trioxide (127 mg, 0.33 mmol) and the mixture was stirred at r.t. for 10 min. 4-Aminobenzotrifluoride (65 mg, 0.39 mmol) was added to the above mixture and the resulting reaction mixture was stirred at r.t. for 16 h. The mixture was quenched by NaOH (2N in water, 2 mL) and diluted with H$_2$O (20 mL). The resulting mixture was extracted with EtOAc three times. The combined organic layers were dried over Na$_2$SO$_4$, filtered and concentrated under reduced pressure. The residue was purified by Prep-HPLC to give compound 5 (2.65 mg, yield 5%) as a white solid. MS (ESI): m/z 437.4 (M+H)$^+$. $^1$H NMR (500 MHz, d$_6$-DMSO) δ 10.63 (s, 1H), 8.80 (d, J=4.5 Hz, 1H), 8.10-8.05 (m, 1H), 8.03 (d, J=11.0 Hz, 1H), 7.84 (d, J=8.0 Hz, 2H), 7.69-7.63 (m, 3H), 7.36 (s, 1H), 3.48-3.41 (m, 1H), 2.25-2.17 (m, 1H), 1.99-1.85 (m, 4H), 1.80-1.74 (m, 2H), 1.35-1.25 (m, 1H), 1.21-1.09 (m, 2H), 0.99-0.95 (m, 1H).

Example 6

N-(4-cyanophenyl)-6-(6-fluoroquinolin-4-yl)spiro[2.5]octane-1-carboxamide

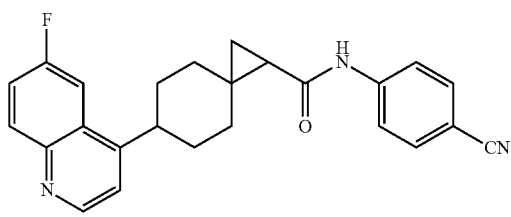 [SMILES: N#Cc1ccc(NC(=O)C2CC23CCC(c2ccnc4ccc(F)cc24)CC3)cc1]

Compound 6 was prepared using the similar procedures as described for compound 5 using 4-aminobenzonitrile to replace 4-aminobenzotrifluoride. MS (ESI): m/z 400.4 (M+H)$^+$. $^1$H NMR (500 MHz, d$_6$-DMSO) δ 10.70 (s, 1H), 8.80 (d, J=4.5 Hz, 1H), 8.10-8.06 (m, 1H), 8.03 (d, J=11.0 Hz, 1H), 7.82 (d, J=8.5 Hz, 2H), 7.75 (d, J=8.5 Hz, 2H), 7.66 (t, J=9.0 Hz, 1H), 7.35 (d, J=3.5 Hz, 1H), 3.48-3.40 (m, 1H), 2.25-2.17 (m, 1H), 1.99-1.83 (m, 4H), 1.81-1.74 (m, 2H), 1.33-1.23 (m, 1H), 1.21-1.10 (m, 2H), 1.02-0.96 (m, 1H).

Example 7

N-(6-chloropyridin-3-yl)-6-(6-fluoroquinolin-4-yl)spiro[2.5]octane-1-carboxamide

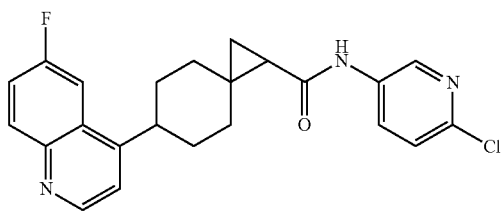 [SMILES: O=C(Nc1ccc(Cl)nc1)C1CC12CCC(c1ccnc3ccc(F)cc13)CC2]

Compound 7 was prepared using the similar procedures as described for compound 5 using 5-amino-2-chloropyridine to replace 4-aminobenzotrifluoride. MS (ESI): m/z 410.4 (M+H)$^+$. $^1$H NMR (500 MHz, d$_6$-DMSO) δ 10.62 (s, 1H), 8.81 (s, 1H), 8.63 (s, 1H), 8.15-8.06 (m, 2H), 8.03 (d, J=11.0 Hz, 1H), 7.66 (t, J=8.5 Hz, 1H), 7.45 (d, J=8.0 Hz, 1H), 7.38 (s, 1H), 3.48-3.41 (m, 1H), 2.25-2.16 (m, 1H), 1.99-1.82 (m, 4H), 1.82-1.72 (m, 2H), 1.35-1.26 (m, 1H), 1.20-1.09 (m, 2H), 1.00-0.95 (m, 1H).

Example 8

N-(5-chloropyridin-2-yl)-6-(6-fluoroquinolin-4-yl)spiro[2.5]octane-1-carboxamide

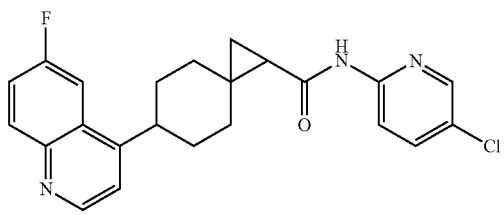 [SMILES: O=C(Nc1ccc(Cl)cn1)C1CC12CCC(c1ccnc3ccc(F)cc13)CC2]

Compound 8 was prepared using the similar procedures as described for compound 5 using 2-amino-5-chloropyridine to replace 4-aminobenzotrifluoride. MS (ESI): m/z 410.4 (M+H)$^+$. $^1$H NMR (500 MHz, d$_6$-DMSO) δ 11.04 (s, 1H), 8.80 (s, 1H), 8.38 (s, 1H), 8.13 (d, J=8.5 Hz, 1H), 8.07 (t, J=8.0 Hz, 1H), 8.02 (d, J=11.0 Hz, 1H), 7.85 (d, J=9.0 Hz, 1H), 7.66 (t, J=8.0 Hz, 1H), 7.34 (s, 1H), 3.47-3.40 (m, 1H), 2.19 (t, J=12.5 Hz, 1H), 2.02-1.84 (m, 5H), 1.78 (d, J=11.0 Hz, 1H), 1.33-1.22 (m, 1H), 1.21-1.15 (m, 1H), 1.08 (d, J=12.5 Hz, 1H), 0.98-0.92 (m, 1H).

Example 9

N-(4-chlorophenyl)-6-(6-fluoro-7-methylquinolin-4-yl)spiro[2.5]octane-1-carboxamide

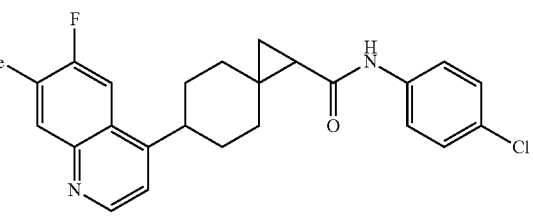

65

-continued

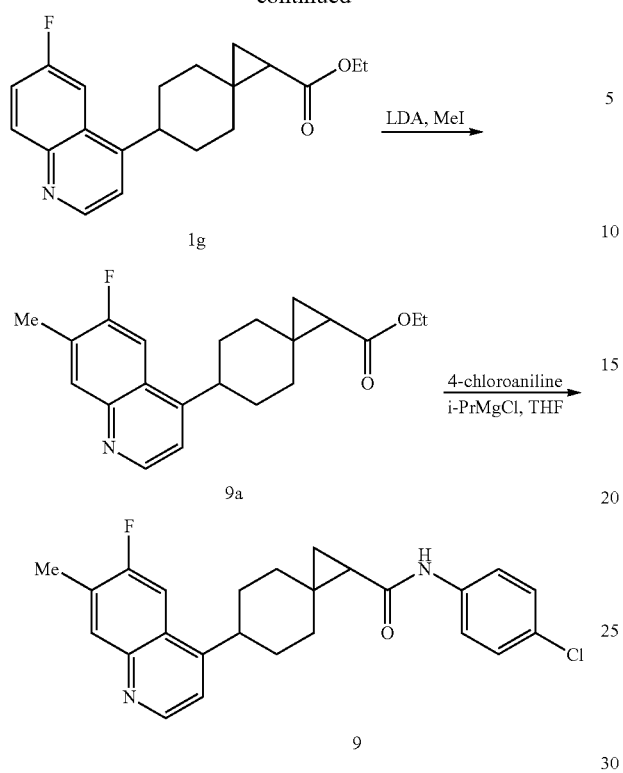

Step 1: To a mixture of diisopropylamine (123 mg, 1.22 mmol) in dry THF (5 mL) at −78° C., n-BuLi (2.5 M, 0.5 mL, 1.25 mmol) was added dropwise, followed by a solution of compound 1g (200 mg, 0.61 mmol) in THF (2 mL). After the mixture was stirred at −78° C. for 1 h, a solution of CH₃I (173 mg, 1.22 mmol) in dry THF (2 mL) was added dropwise. The resulting mixture was stirred at −78° C. for 0.5 h and then warmed to r.t. for 16 h. The reaction was quenched by aq. NH₄Cl solution. The mixture was extracted with ethyl acetate three times and the combined organic layers were dried over Na₂SO₄, filtered and concentrated under reduced pressure. The residue was purified by Prep-TLC to give compound 9a (24 mg, yield: 12%) as colorless oil. MS (ESI): m/z 342.4 (M+H)⁺.

Step 2: To a mixture of 4-chloroaniline (36 mg, 0.28 mmol) in dry THF (2 mL) at 0° C., isopropylmagnesium chloride solution (2.0 M in THF, 0.2 mL, 0.4 mmol) was added dropwise. After the mixture was stirred at r.t. for 5 min, a solution of compound 9a (24 mg, 0.07 mmol) in dry THF (1 mL) was added dropwise. The resulting mixture was stirred at r.t. for 16 h. The reaction was quenched by aq. NH₄Cl solution. The mixture was extracted with ethyl acetate three times and the combined organic layers were dried over Na₂SO₄, filtered and concentrated under reduced pressure. The residue was purified by Prep-HPLC to give compound 9 (12.01 mg, yield: 41%) as a white solid. MS (ESI): m/z 423.4 (M+H)⁺. ¹H NMR (500 MHz, d₆-DMSO) δ 10.37 (s, 1H), 8.75 (s, 1H), 7.99-7.91 (m, 2H), 7.80-7.56 (m, 3H), 7.34 (d, J=8.0 Hz, 2H), 7.28 (s, 1H), 3.44-3.37 (m, 1H), 2.44 (s, 3H), 2.23-2.14 (m, 1H), 1.98-1.84 (m, 4H), 1.78-1.69 (m, 2H), 1.17-1.07 (m, 2H), 0.95-0.92 (m, 1H).

66

Example 10

(S)-N-(4-chlorophenyl)-6-(6-fluoroquinolin-4-yl) spiro[2.5]octane-1-carboxamide (10a)

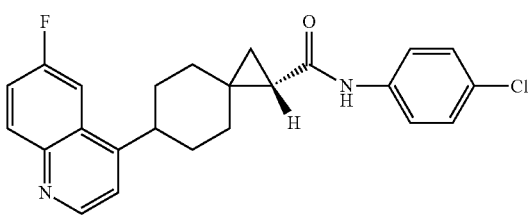 [SMILES: O=C(Nc1ccc(Cl)cc1)[C@H]1CC12CCC(c1ccnc3ccc(F)cc13)CC2]

(R)-N-(4-chlorophenyl)-6-(6-fluoroquinolin-4-yl) spiro[2.5]octane-1-carboxamide (10b)

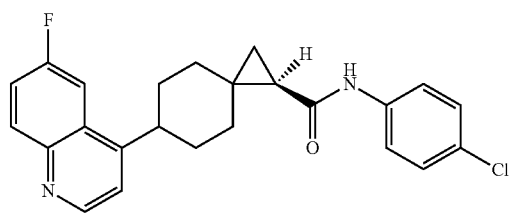 [SMILES: O=C(Nc1ccc(Cl)cc1)[C@@H]1CC12CCC(c1ccnc3ccc(F)cc13)CC2]

Compound 10a and compound 10b were obtained by chiral column separation of compound 1. Absolute stereochemistry arbitrarily assigned.

Compound 10a: MS (ESI): m/z 409.4 (M+H)⁺. ¹H NMR (500 MHz, d₆-DMSO) δ 10.37 (s, 1H), 8.81 (s, 1H), 8.11-8.05 (m, 1H), 8.02 (d, J=11.0 Hz, 1H), 7.69-7.63 (m, 3H), 7.38-7.31 (m, 3H), 3.48-3.40 (m, 1H), 2.20 (t, J=12.0 Hz, 1H), 2.00-1.85 (m, 4H), 1.78 (d, J=12.0 Hz, 1H), 1.72 (d, J=6.5 Hz, 1H), 1.36-1.28 (m, 1H), 1.17-1.08 (m, 2H), 0.96-0.90 (m, 1H). Compound 10b: MS (ESI): m/z 409.4 (M+H)⁺. ¹H NMR (500 MHz, d₆-DMSO) δ 10.37 (s, 1H), 8.81 (s, 1H), 8.10-8.05 (m, 1H), 8.02 (d, J=11.0 Hz, 1H), 7.69-7.63 (m, 3H), 7.38-7.31 (m, 3H), 3.48-3.40 (m, 1H), 2.20 (t, J=12.0 Hz, 1H), 1.98-1.84 (m, 4H), 1.78 (d, J=12.0 Hz, 1H), 1.72 (d, J=6.5 Hz, 1H), 1.37-1.28 (m, 1H), 1.17-1.08 (m, 2H), 0.96-0.90 (m, 1H).

Example 11

N-(4-bromophenyl)-6-(6-fluoroquinolin-4-yl)spiro [2.5]octane-1-carboxamide

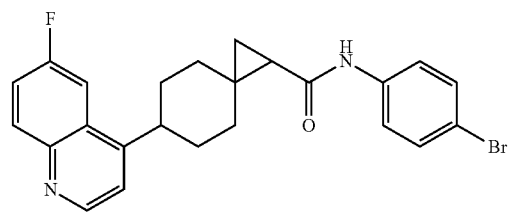 [SMILES: O=C(Nc1ccc(Br)cc1)C1CC12CCC(c1ccnc3ccc(F)cc13)CC2]

Compound 11 was prepared using the similar procedures as described for compound 5 using 4-bromoaniline to replace 4-aminobenzotrifluoride. MS (ESI): m/z 454.1 (M+H)$^+$. $^1$H NMR (500 MHz, d$_6$-DMSO) δ 10.40 (s, 1H), 8.80 (d, J=4.5 Hz, 1H), 8.08 (dd, J=9.0, 6.0 Hz, 1H), 8.03 (dd, J=11.0, 2.5 Hz, 1H), 7.69-7.64 (m, 1H), 7.63-7.58 (m, 2H), 7.50-7.44 (m, 2H), 7.35 (d, J=4.5 Hz, 1H), 3.44 (t, J=11.5 Hz, 1H), 2.20 (td, J=12.5, 4.0 Hz, 1H), 2.00-1.84 (m, 4H), 1.77 (d, J=12.5 Hz, 1H), 1.72 (dd, J=7.5, 5.5 Hz, 1H), 1.35-1.25 (m, 1H), 1.17-1.13 (m, 1H), 1.10 (d, J=12.5 Hz, 1H), 0.93 (dd, J=7.5, 4.0 Hz, 1H).

Example 12

N-(4-chloro-3-fluorophenyl)-6-(6-fluoroquinolin-4-yl)spiro[2.5]octane-1-carboxamide

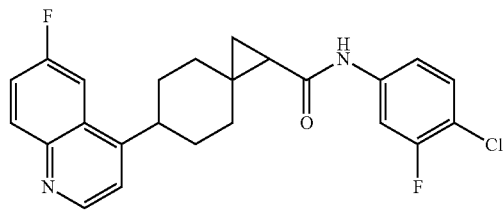 [SMILES: O=C(Nc1ccc(Cl)c(F)c1)C1CC12CCC(c1ccnc3ccc(F)cc13)CC2]

Compound 12 was prepared using the similar procedures as described for compound 5 using 4-chloro-3-fluoroaniline to replace 4-aminobenzotrifluoride. MS (ESI): m/z 428.1 (M+H)$^+$. $^1$H NMR (500 MHz, d$_6$-DMSO) $^1$H NMR (500 MHz, d$_6$-DMSO) δ 10.62 (s, 1H), 8.80 (d, J=3.5 Hz, 1H), 8.10-8.05 (m, 1H), 8.02 (d, J=10.5 Hz, 1H), 7.82 (d, J=12.0 Hz, 1H), 7.66 (t, J=8.5 Hz, 1H), 7.49 (t, J=8.5 Hz, 1H), 7.37 (d, J=9.5 Hz, 2H), 3.47-3.41 (m, 1H), 2.23-2.15 (m, 1H), 1.97-1.82 (m, 4H), 1.77 (d, J=12.5 Hz, 1H), 1.71 (t, J=6.0 Hz, 1H), 1.32-1.21 (m, 1H), 1.18-1.14 (m, 1H), 1.11 (d, J=12.5 Hz, 1H), 0.98-0.94 (m, 1H).

Example 13

N-(5-chlorothiophen-2-yl)-6-(6-fluoroquinolin-4-yl)spiro[2.5]octane-1-carboxamide

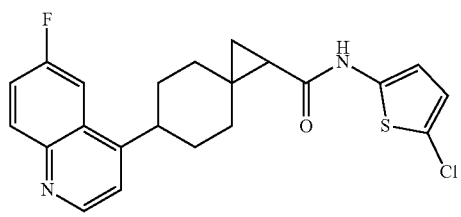 [SMILES: O=C(Nc1ccc(Cl)s1)C1CC12CCC(c1ccnc3ccc(F)cc13)CC2]

Compound 13 was prepared using the similar procedures as described for compound 5 using 5-chloro-thiophen-2-ylamine to replace 4-aminobenzotrifluoride. MS (ESI): m/z 415.3 (M+H)$^+$. $^1$H NMR (500 MHz, d$_6$-DMSO) δ 11.71 (s, 1H), 8.81 (d, J=4.0 Hz, 1H), 8.10-8.06 (m, 1H), 8.03 (d, J=11.0 Hz, 1H), 7.67 (t, J=8.5 Hz, 1H), 7.36 (d, J=4.0 Hz, 1H), 1H), 6.86 (d, J=3.5 Hz, 1H), 6.50 (d, J=3.5 Hz, 1H), 3.48-3.40 (m, 1H), 2.23-2.16 (m, 1H), 1.97-1.74 (m, 5H), 1.72-1.67 (m, 1H), 1.28-1.16 (m, 2H), 1.11 (d, J=12.5 Hz, 1H), 1.02-0.98 (m, 1H).

Example 14

N-(4-chlorophenyl)-6-(6-fluoroquinolin-4-yl)spiro[2.5]octane-1-sulfonamide

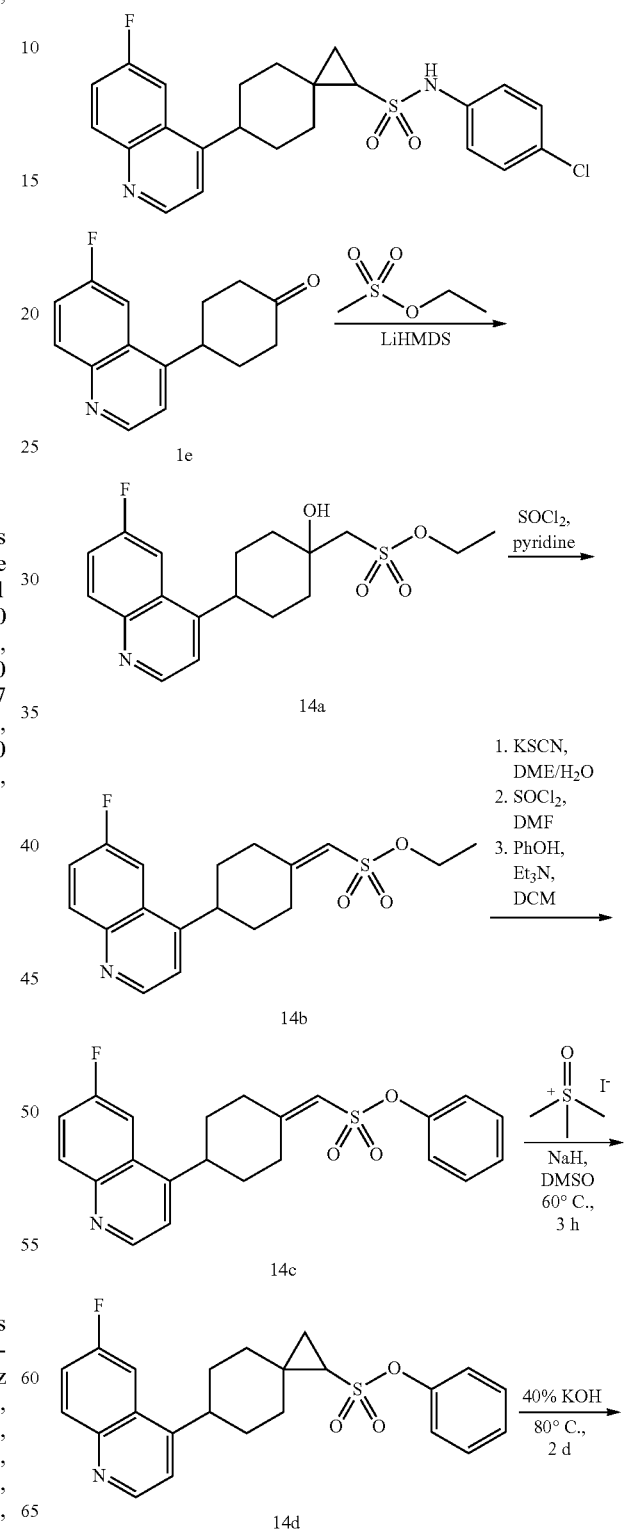

-continued

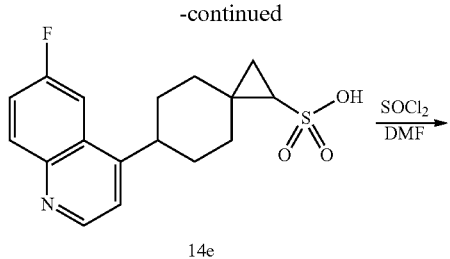

14e

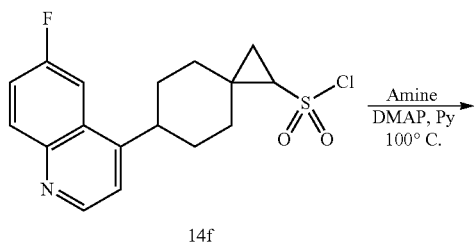

14f

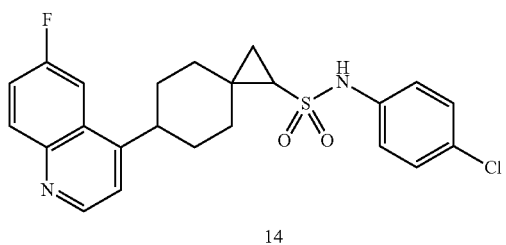

14

Step 1: To a mixture of ethyl methanesulfonate (2.45 g, 19.75 mmol) in dry THF (30 mL) under $N_2$ at −78° C., lithium bis(trimethylsilyl)amide (1.0 M in THF, 19.8 mL, 19.8 mmol) was added dropwise. After the mixture was stirred at −78° C. for 30 min, a solution of compound 1e (4.0 g, 16.46 mmol) in dry THF (20 mL) was added dropwise. The resulting mixture was stirred at −78° C. for 3 h. The reaction was quenched by $H_2O$. The mixture was concentrated under reduced pressure to give compound 14a (6.2 g, yield: 100%) as a white solid, which was used to the next step directly. MS (ESI): m/z 368.4 (M+H)$^+$.

Step 2: To a mixture of compound 14a (2.0 g, 5.45 mmol) in pyridine (10 mL) at 0° C., thionyl chloride (1.30 g, 10.90 mmol) was added dropwise. The mixture was stirred at 0° C. for 2 h and then warmed to r.t. for 16 h. The reaction was quenched by aq. $NaHCO_3$. The mixture was extracted with ethyl acetate three times and the combined organic layers were washed with brine, dried over $Na_2SO_4$, filtered and concentrated under reduced pressure. The residue was purified by column chromatography on silica gel to give compound 14b (216 mg, yield: 11%) as yellow oil. MS (ESI): m/z 350.4 (M+H)$^+$.

Step 3: To a solution of compound 14b (216 mg, 0.62 mmol) in 1, 2-dimethoxyethane (5 mL) and $H_2O$ (5 mL) was added KSCN (60 mg, 0.62 mmol), and the mixture was stirred at 90° C. for 16 h. The mixture was cooled to r.t. and diluted with $H_2O$ (10 mL), washed with EA three times. The aqueous phase was concentrated under reduced pressure to afford crude product, which was dissolved in thionyl chloride (5 mL). DMF (0.5 mL) was added dropwise to the above solution; the resulting reaction mixture was stirred at 80° C. for 3 h. The reaction mixture was concentrated under reduced pressure. The residue was dissolved in DCM (5 mL) at 0° C., phenol (117 mg, 1.24 mmol) was added to the above solution, followed by the addition of $Et_3N$ (313 mg, 3.10 mmol). The resulting mixture was stirred at 0° C. for 1 h and then warmed to r.t. while stirring for another 16 h. The reaction was quenched by aq. $NH_4Cl$ solution. The mixture was extracted with ethyl acetate three times and the combined organic layers were washed with brine, dried over $Na_2SO_4$, filtered and concentrated under reduced pressure. The residue was purified by Prep-TLC to give compound 14c (124 mg, yield: 50%) as a yellow solid. MS (ESI): m/z 398.4 (M+H)$^+$.

Step 4: To a suspension of NaH (60% w/w in mineral oil, 37 mg, 0.93 mmol) in DMSO (15 mL) was added trimethylsulfoxonium iodide (205 mg, 0.93 mmol). After the mixture was stirred at r.t. for 1 h, a solution of compound 14c (124 mg, 0.31 mmol) in DMSO (5 mL) was added to the above mixture and the resulting reaction mixture was stirred at 60° C. for 3 h. The mixture was quenched by $H_2O$ and extracted with EtOAc three times. The combined organic layers were washed with brine, dried over $Na_2SO_4$, filtered and concentrated under reduced pressure. The residue was purified by Prep-TLC to give compound 14d (65 mg, yield: 51%) as a white solid. MS (ESI): m/z 412.4 (M+H)$^+$.

Step 5: To a solution of compound 14d (50 mg, 0.12 mmol) in ethanol (5 mL) was added KOH (40% in water, 3 mL) and the mixture was stirred at 80° C. for 48 h. The mixture was cooled to r.t. and adjusted to pH=1~3 by 4N HCl solution. The mixture was concentrated under reduced pressure to afford a white solid, which was suspended in MeOH. After filtration, the filtrate was concentrated under reduced pressure to give compound 14e (35 mg, yield 87%) as a yellow solid, which was used to the next step directly. MS (ESI): m/z 336.5 (M+H)$^+$.

Step 6: To a solution of compound 14e (35 mg, 0.10 mmol) in thionyl chloride (5 mL) was added DMF (0.5 mL), and the mixture was stirred at 80° C. for 3 h. The mixture was concentrated under reduced pressure to give compound 14f (30 mg, yield: 85%) as a white solid, which was used to the next step directly. MS (ESI): m/z 354.5 (M+H)$^+$.

Step 7: To a solution of compound 14f (30 mg, 0.08 mmol) in pyridine (2 mL) were subsequently added 4-chloroaniline (20 mg, 0.16 mmol) and DMAP (12 mg, 0.01 mmol) and the mixture was stirred at 100° C. for 16 h. The mixture was concentrated under reduced pressure. The residue was diluted with $H_2O$ (20 mL). The mixture was extracted with ethyl acetate three times and the combined organic layers were washed with brine, dried over $Na_2SO_4$, filtered and concentrated under reduced pressure. The residue was purified by Prep-HPLC to give compound 14 (5.69 mg, yield: 16%) as a white solid. MS (ESI): m/z 445.5

(M+H)+. 1H NMR (500 MHz, d6-DMSO) δ 10.10 (br, 1H), 8.82 (d, J=4.5 Hz, 1H), 8.09 (dd, J=9.0, 6.0 Hz, 1H), 8.02 (dd, J=11.0, 2.5 Hz, 1H), 7.71-7.64 (m, 1H), 7.40 (d, J=9.0 Hz, 2H), 7.27 (d, J=9.0 Hz, 2H), 7.16 (d, J=4.5 Hz, 1H), 3.45-3.40 (m, 1H), 2.56 (dd, J=8.0, 5.5 Hz, 1H), 2.13 (d, J=13.5 Hz, 1H), 2.08-1.98 (m, 2H), 1.88-1.74 (m, 3H), 1.52-1.42 (m, 1H), 1.20-1.12 (m, 2H), 1.09 (d, J=13.5 Hz, 1H).

Compound 15, 16, 17, 18, 19 was prepared using the similar procedures as described for compound 14

| Compound | Structure | LCMS (M + H)+ | NMR |
|---|---|---|---|
| 15 | 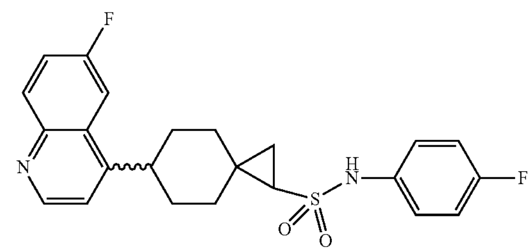 [SMILES: O=S(=O)(Nc1ccc(F)cc1)C1CC12CCC(c1ccnc3ccc(F)cc13)CC2] | 429.14 | 1H NMR (500 MHz, d6-DMSO) δ 10.27 (s, 1H), 8.79 (d, J = 5.2 Hz, 1H), 8.01-7.94 (m, 2H), 7.54 (d, J = 8.3 Hz, 1H), 7.47 (d, J = 5.0 Hz, 1H), 7.15-6.98 (m, 4H), 3.20-3.12 (m, 1H), 2.48 (dd, J = 8.0, 7.1 Hz, 1H), 1.98 (dd, J = 10.2, 3.2 Hz, 1H), 1.91-1.45 (m, 7H), 1.45-1.22 (m, 2H) |
| 16 | 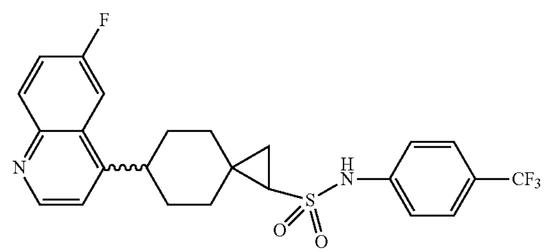 [SMILES: O=S(=O)(Nc1ccc(C(F)(F)F)cc1)C1CC12CCC(c1ccnc3ccc(F)cc13)CC2] | 479.14 | 1H NMR (500 MHz, d6-DMSO) δ 10.82 (s, 1H), 8.74 (d, J = 5.1 Hz, 1H), 7.90-8.01 (m, 2H), 7.61 (dd, J = 8.4, 1.9 Hz, 2H), 7.53 (dd, J = 8.3, 1.7 Hz, 1H), 7.44 (d, J = 5.1 Hz, 1H), 7.21 (dd, J = 8.4, 1.3 Hz, 2H), 3.15 (tt, J = 10.2, 2.5 Hz, 1H), 2.46 (dd, J = 8.1, 7.5 Hz, 1H), 1.45-1.98 (m, 8H), 1.30-1.45 (m, 2H) |
| 17 | 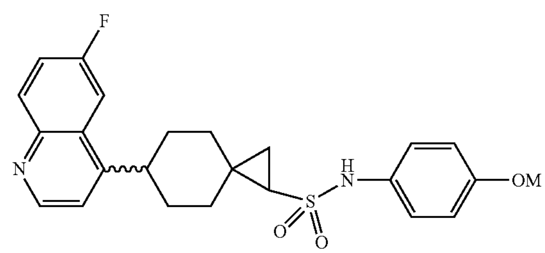 | 441.16 | 1H NMR (500 MHz, d6-DMSO) δ 10.42 (s, 1H), 8.92 (d, J = 5.0 Hz, 1H), 8.11-7.97 (m, 2H), 7.59 (d, J = 8.0 Hz, 1H), 7.41 (d, J = 5.2 Hz, 1H), 6.94 (dd, J = 8.5, 1.6 Hz, 2H), 6.66 (dd, J = 8.5, 1.7 Hz, 2H), 3.77 (s, 3H), 3.22-3.11 (m, 1H), 2.55 (dd, J = 8.2, 7.0 Hz, 1H), 2.08 (dd, J = 10.7, 3.5 Hz, 1H), 1.95-1.40 (m, 7H), 1.35-1.12 (m, 2H) |
| 18 | 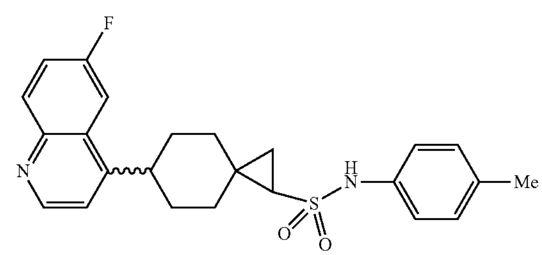 [SMILES: Cc1ccc(NS(=O)(=O)C2CC23CCC(c2ccnc4ccc(F)cc24)CC3)cc1] | 425.17 | 1H NMR (500 MHz, d6-DMSO) δ 10.6 (s, 1H), 8.77 (d, J = 5.1 Hz, 1H), 7.90-7.97 (m, 2H), 7.56 (dd, J = 8.2, 1.6 Hz, 1H), 7.42 (d, J = 5.1 Hz, 1H), 7.33 (dd, J = 8.1, 1.3 Hz, 2H), 6.90 (dd, J = 8.1, 1.3 Hz, 2H), 3.15 (tt, J = 10.2, 2.5 Hz, 1H), 2.46 (dd, J = 8.1, 7.5 Hz, 1H), 2.21 (s, 3H), 1.49-1.95 (m, 8H), 1.45-1.10 (m, 2H) |
| 19 | 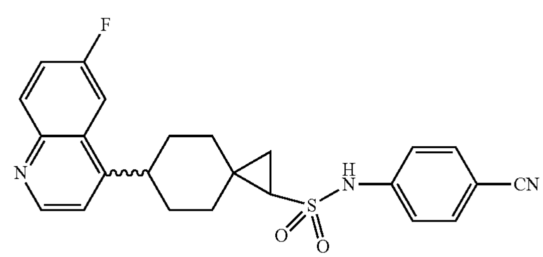 [SMILES: N#Cc1ccc(NS(=O)(=O)C2CC23CCC(c2ccnc4ccc(F)cc24)CC3)cc1] | 436.15 | 1H NMR (500 MHz, d6-DMSO) δ 10.20 (s, 1H), 8.82 (d, J = 5.3 Hz, 1H), 8.14-7.99 (m, 2H), 7.79 (d, J = 8.1 Hz, 1H), 7.61 (d, J = 5.5 Hz, 1H), 7.02 (dd, J = 8.2, 1.7 Hz, 2H), 6.72 (dd, J = 8.3, 1.8 Hz, 2H), 3.20-3.10 (m, 1H), 2.54 (dd, J = 8.0, 7.2 Hz, 1H), 2.18 (dd, J = 10.2, 3.2 Hz, 1H), 1.99-1.42 (m, 7H), 1.39-1.10 (m, 2H) |

Example 20

N-(4-chlorophenyl)-6-(6-fluoroquinolin-4-yl)-1-azaspiro[2.5]octane-1-carboxamide

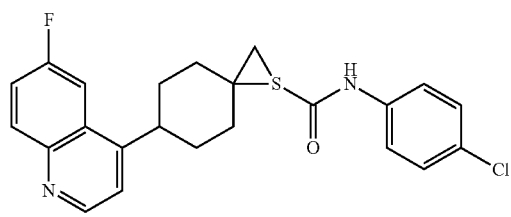

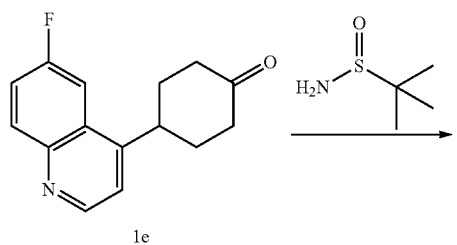

1e

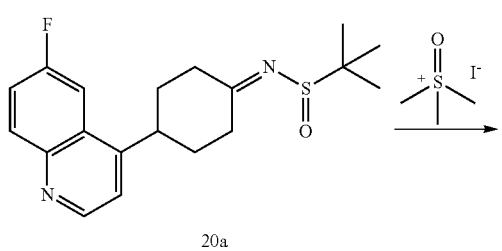

20a

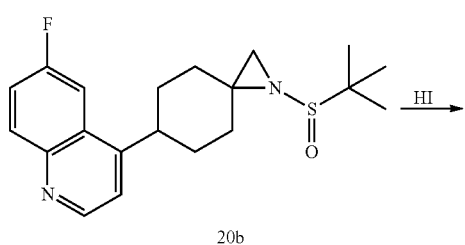

20b

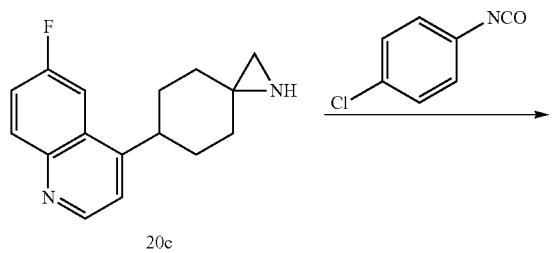

20c

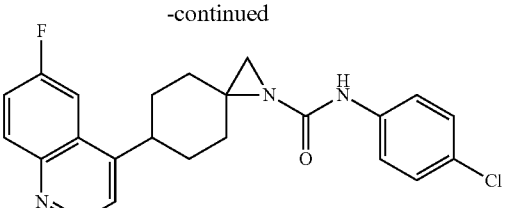

20

Step 1: To a mixture of compound 1e (500 mg, 2.06 mmol) in dry THF (20 mL), titanium ethoxide (2.81 g, 12.36 mmol) was added under $N_2$, followed by the addition of tert-butanesulfinamide (747 mg, 6.18 mmol). The mixture was stirred at 60° C. for 4 h. The mixture was cooled to r.t. and brine (20 mL) was added while stirring. The suspension was filtered and the filter cake was washed with EtOAc. The filtrate was washed with brine, dried over $Na_2SO_4$, filtered and concentrated under reduced pressure. The residue was purified by column chromatography on silica gel to give compound 20a (510 mg, yield: 86%). MS (ESI): m/z 347.4 $(M+H)^+$.

Step 2: To a solution of trimethylsulfoxonium iodide (486 mg, 2.21 mmol) in DMSO (20 mL) was added NaH (60% w/w in mineral oil, 88 mg, 2.21 mmol). After the mixture was stirred at r.t. for 20 min, a solution of compound 20a (510 mg, 1.47 mmol) in DMSO (2 mL) was added to the above mixture and the resulting reaction mixture was stirred at r.t. for 1 h. The mixture was quenched by $H_2O$ and extracted with EtOAc (20 mL×3). The combined organic layers were washed with brine (20 mL), dried over dried over $Na_2SO_4$, filtered and concentrated under reduced pressure. The residue was purified by column chromatography on silica gel to give compound 20b (320 mg, yield: 60%). MS (ESI): m/z 361.4 $(M+H)^+$.

Step 3: To a solution of compound 20b (320 mg, 0.89 mmol) in THF (20 mL) was added HI (57% w/w in water, 3 mL) and the mixture was stirred at r.t. for 30 min. The mixture was cooled to 0° C. and adjusted to pH=12-14 by 2N KOH solution. The resulting mixture was stirred at r.t. for 45 min and then extracted with EtOAc (20 mL×3). The combined organic layers were washed with brine (20 mL), dried over $Na_2SO_4$, filtered and concentrated under reduced pressure to give compound 20c (200 mg, yield: 88%), which was used to the next step directly. MS (ESI): m/z 257.5 $(M+H)^+$.

Step 4: To a solution of compound 20c (100 mg, 0.39 mmol) in THF (10 mL) at 0° C. was added triethyl amine (118 mg, 1.17 mmol), followed by the addition of 4-chlorophenyl isocyanate (60 mg, 0.39 mmol); the mixture was stirred at r.t. for 3 h. The mixture was quenched by aq. $NH_4Cl$ (10 mL) and extracted with EtOAc (10 mL×3). The combined organic layers were washed with brine (10 mL), dried over dried over $Na_2SO_4$, filtered and concentrated under reduced pressure. The residue was purified by Prep-HPLC to give compound 20 (700 mg, yield: 44%) as a white solid. MS (ESI): m/z 410.4 $(M+H)^+$.

Compound 21, 22, 23, 24, 25 was prepared using the similar procedures as described for compound 20.

| compound | Structure | LCMS (M + H)+ | NMR |
|---|---|---|---|
| 20 | 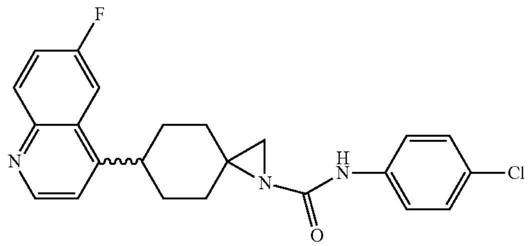 [SMILES: O=C(Nc1ccc(Cl)cc1)N1CC12CCC(c1ccnc3ccc(F)cc13)CC2] | 410.4 | ¹H NMR (500 MHz, d₆-DMSO) δ 9.88 (s, 1H), 8.86 (s, 1H), 8.13-8.07 (m, 2H), 7.68 (t, J = 8.5 Hz, 1H), 7.63 (d, J = 8.0 Hz, 2H), 7.33 (d, J = 8.0 Hz, 2H), 7.29-7.23 (m, 1H), 3.54-3.48 (m, 1H), 2.26-2.22 (m, 3H), 2.17-2.08 (m, 2H), 1.87-1.79 (m, 3H), 1.40 (d, J = 13.5 Hz, 2H). |
| 21 | 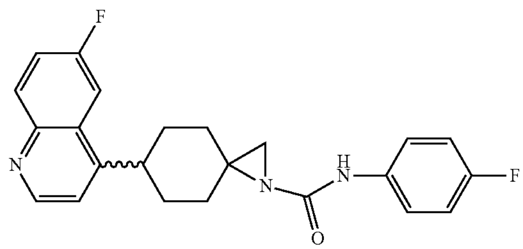 [SMILES: O=C(Nc1ccc(F)cc1)N1CC12CCC(c1ccnc3ccc(F)cc13)CC2] | 394.17 | ¹H NMR (500 MHz, d₆-DMSO) δ 9.94 (s, 1H), 8.81 (s, 1H), 8.13-8.07 (m, 2H), 7.68 (t, J = 8.5 Hz, 1H), 7.63 (d, J = 8.0 Hz, 2H), 7.33 (d, J = 8.0 Hz, 2H), 7.29-7.23 (m, 1H), 3.54-3.48 (m, 1H), 2.26-2.22 (m, 3H), 2.17-2.08 (m, 2H), 1.87-1.79 (m, 3H), 1.40 (d, J = 13.5 Hz, 2H). |
| 22 | 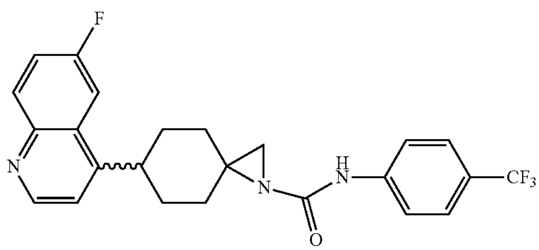 [SMILES: O=C(Nc1ccc(C(F)(F)F)cc1)N1CC12CCC(c1ccnc3ccc(F)cc13)CC2] | 444.17 | ¹H NMR (500 MHz, d₆-DMSO) δ 9.92 (s, 1H), 8.76 (d, J = 5.1 Hz, 1H), 8.17-8.00 (m, 2H), 7.68-7.63 (m, 3H), 7.43 (d, J = 8.0 Hz, 2H), 7.29 (d, J = 5.1 Hz, 1H), 3.54-3.48 (m, 1H), 2.25-2.22 (m, 2H), 2.17-1.79 (m, 6H), 1.50 (d, J = 13.5 Hz, 2H). |
| 23 | 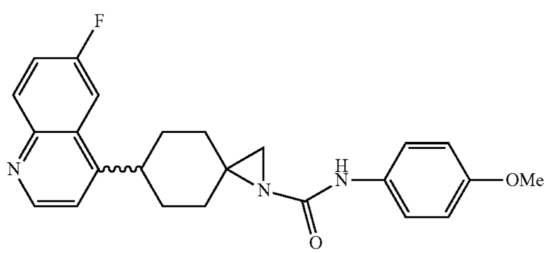 [SMILES: COc1ccc(NC(=O)N2CC23CCC(c2ccnc4ccc(F)cc24)CC3)cc1] | 406.19 | ¹H NMR (500 MHz, d6-DMSO) δ 10.22 (s, 1H), 8.87 (d, J = 5.4 Hz, 1H), 8.10-7.93 (m, 2H), 7.55-7.46 (m, 2H), 7.40 (d, J = 5.5 Hz, 2H), 6.60 (dd, J = 8.2, 2.7 Hz, 2H), 3.71 (s, 3H), 3.26-3.14 (m, 1H), 2.75 (s, 2H), 2.05-1.70 (m, 8H) |
| 24 | 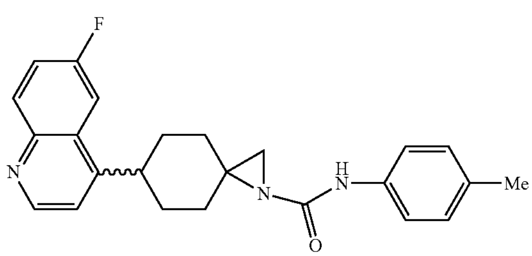 [SMILES: Cc1ccc(NC(=O)N2CC23CCC(c2ccnc4ccc(F)cc24)CC3)cc1] | 390.19 | ¹H NMR (500 MHz, d₆-DMSO) δ 9.98 (s, 1H), 8.86 (s, 1H), 8.10-7.97 (m, 2H), 7.62 (t, J = 8.5 Hz, 1H), 7.53 (d, J = 8.0 Hz, 2H), 7.31 (d, J = 8.0 Hz, 2H), 7.32-7.25 (m, 1H), 3.51-3.42 (m, 1H), 2.28-2.24 (m, 3H), 2.21 (s, 3H), 2.19-2.03 (m, 2H), 1.88-1.78 (m, 3H), 1.45 (d, J = 13.5 Hz, 2H). |
| 25 | 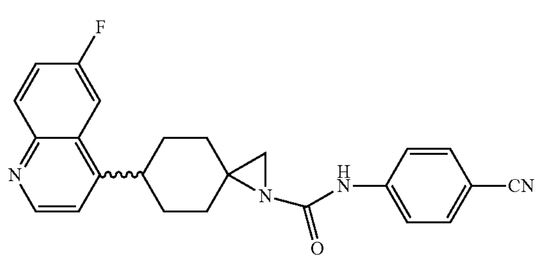 [SMILES: N#Cc1ccc(NC(=O)N2CC23CCC(c2ccnc4ccc(F)cc24)CC3)cc1] | 401.17 | ¹H NMR (500 MHz, d₆-DMSO) δ 9.64 (s, 1H), 8.61 (s, 1H), 8.23-8.02 (m, 2H), 7.88 (dd, J = 8.1, 1.9 Hz, 2H), 7.55 (d, J = 8.2 Hz, 1H), 7.43 (d, J = 5.2 Hz, 1H), 7.39-7.27 (m, 1H), 3.54-3.22 (m, 1H), 2.75 (s, 2H), 2.09-1.71 (m, 8H) |

Example 26

N-(4-chlorophenyl)-6-(6-fluoroquinolin-4-yl)-1-azaspiro[2.5]octane-1-sulfonamide

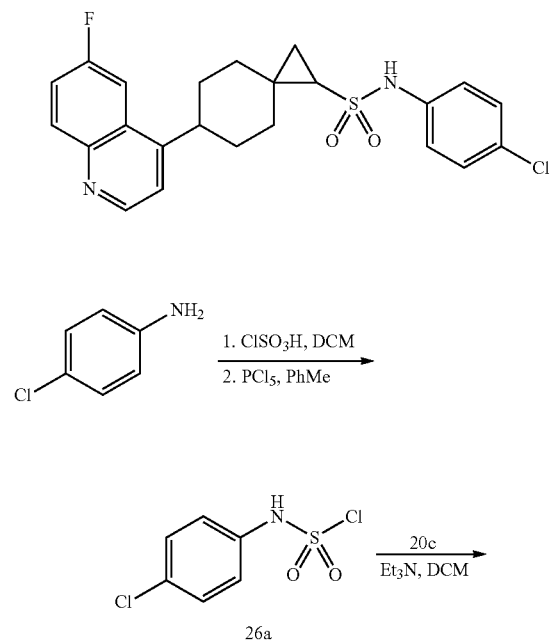

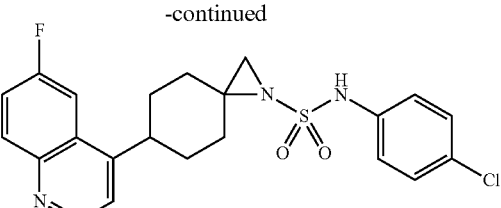

26

Step 1: To a mixture of 4-chloroaniline (3.0 eq) in DCM at 0° C., chlorosulfonic acid (1.0 eq) in DCM was added dropwise. The mixture was stirred at 0° C. for 30 min and then warmed to r.t. for 1 h. Precipitation was formed and filtered. The pale-red solid was dried in vacuum. The crude product was dissolved in toluene, and $PCl_5$ (1.0 eq) was added to the above solution and the resulting mixture was stirred at 75° C. for 2 h. The mixture was cooled to r.t. and filtered. The filter cake was washed with toluene and the filtrate was concentrated and dried in vacuum to give compound 26a (yield: 72%), which was used to the next step directly.

Step 2: To a solution of compound 20c (1.0 eq) in THF at 0° C. was added triethyl amine (2.0 eq), followed by compound 26a (1.2 eq) and the mixture was stirred at r.t. for 3 h. The mixture was quenched by aq. $NH_4Cl$ and extracted with EtOAc (20 mL×3). The combined organic layers were washed with brine (20 mL), dried over dried over $Na_2SO_4$, filtered and concentrated under reduced pressure. The residue was purified by Prep-HPLC to give compound 26 as a white solid.

Compound 28, 30 was prepared using the similar procedures as described for compound 26.

| Compound | Structure | LCMS (M + H)+ | NMR |
|---|---|---|---|
| 26 | 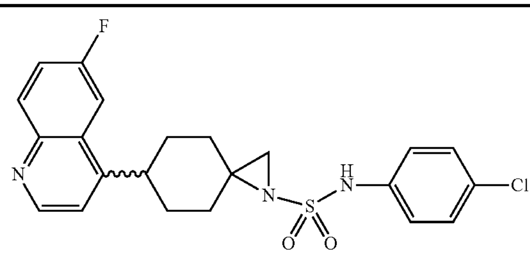 | 447.10 | $^1$H NMR (500 MHz, $d_6$-DMSO) δ 10.08 (s, 1H), 8.76 (d, J = 5.1 Hz, 1H), 8.03-7.97 (m, 2H), 7.68-7.54 (m, 3H), 7.53 (d, J = 5.0 Hz, 1H), 7.23 (d, J = 8.0 Hz, 2H), 3.34-3.28 (m, 1H), 3.26-3.12 (m, 3H), 2.17-2.08 (m, 2H), 1.87-1.39 (m, 5H). |
| 28 | 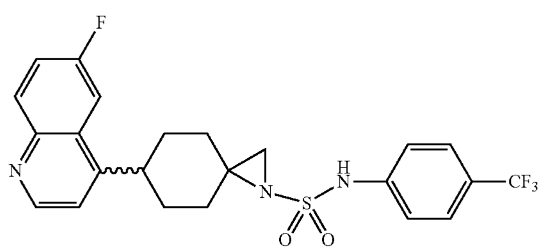 [SMILES: O=S(=O)(Nc1ccc(C(F)(F)F)cc1)N1CC12CCC(c1ccnc3ccc(F)cc13)CC2] | 480.13 | $^1$H NMR (500 MHz, $d_6$-DMSO) δ 10.18 (s, 1H), 8.70 (d, J = 5.1 Hz, 1H), 8.13-8.02 (m, 2H), 7.64-7.50 (m, 3H), 7.43 (d, J = 5.2 Hz, 1H), 7.25 (d, J = 8.2 Hz, 2H), 3.37-3.20 (m, 1H), 3.22-3.10 (m, 3H), 2.19-2.08 (m, 2H), 1.80-1.35 (m, 5H). |
| 30 | 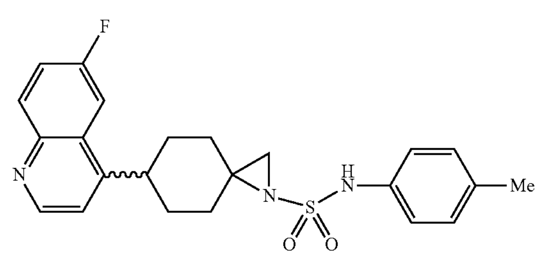 [SMILES: Cc1ccc(NS(=O)(=O)N2CC23CCC(c2ccnc4ccc(F)cc24)CC3)cc1] | 426.16 | $^1$H NMR (500 MHz, $d_6$-DMSO) δ 10.01 (s, 1H), 8.82 (d, J = 5.2 Hz, 1H), 8.00-7.95 (m, 2H), 7.54 (d, J = 8.3 Hz, 1H), 7.43 (d, J = 5.1 Hz, 1H), 7.28 (d, J = 8.1 Hz, 2H), 7.08 (d, J = 8.1 Hz, 2H), 3.24-3.18 (m, 1H), 3.26-3.12 (m, 3H), 2.26 (s, 3H), 2.17-2.08 (m, 2H), 1.87-1.39 (m, 5H). |

Example 32

N-(4-chlorophenyl)-7-(6-fluoroquinolin-4-yl)spiro[3.5]nonane-1-carboxamide

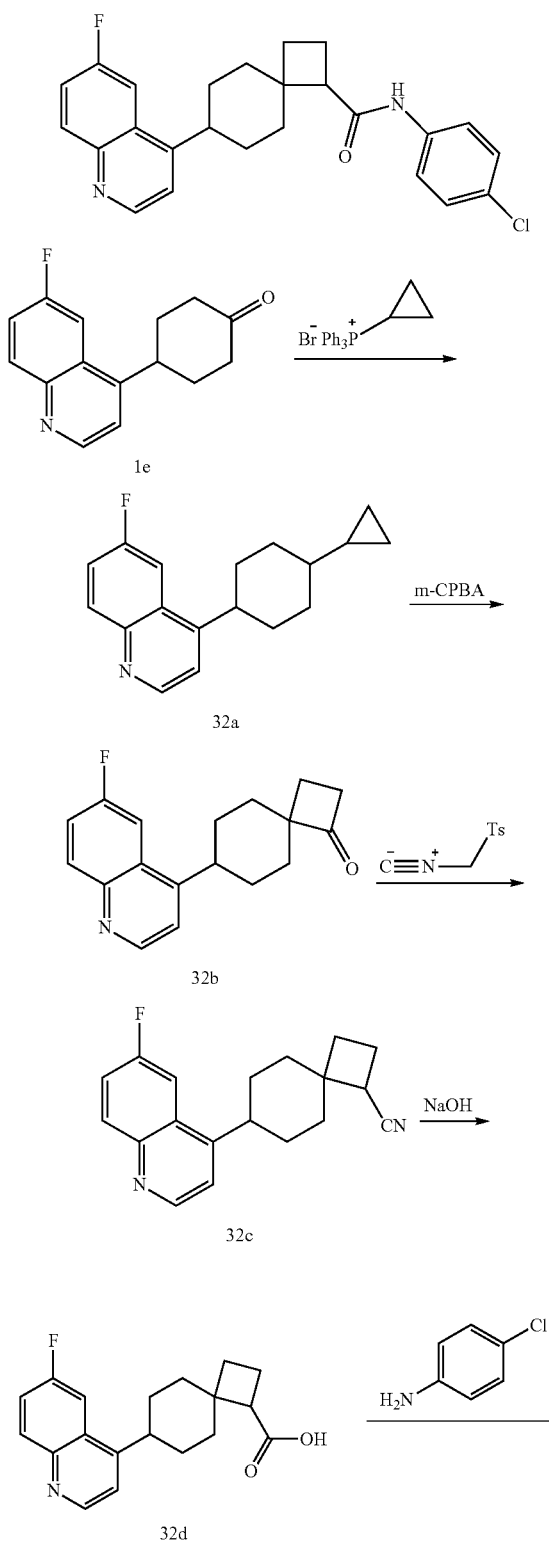

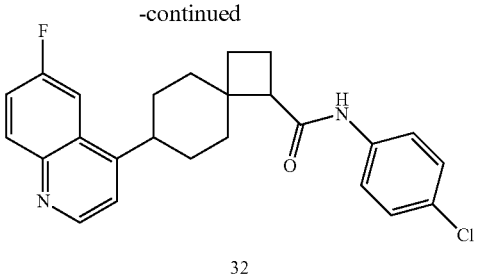

32

Step 1: To a mixture of (cyclopropylmethyl)triphenylphosphonium bromide (2.0 eq) in dry THF, NaH (60% w/w in mineral oil, 2.0 eq) was added. The mixture was stirred at r.t. for 2 h. Compound 1e (1.0 eq) and tris(2-(2-methoxyethoxy)ethyl)amine (0.1 eq) were added to the above solution. The resulting mixture was stirred at r.t. for 10 min and then heated to 62° C. for 4 h. The mixture was concentrated under reduced pressure. The residue was purified by column chromatography on silica gel to afford compound 32a (yield: 51%). MS (ESI): m/z 268.3 (M+H)$^+$.

Step 2: To a mixture of compound 32a (2.0 eq) in DCM, m-CPBA (1.4 eq) was added in portions at 0-5° C. The mixture was stirred at 0-5° C. for 40 min and then warmed to r.t. for 1 h. The mixture was diluted with DCM, washed with 10% NaOH solution and brine. The organic layer was dried over Na$_2$SO$_4$, filtered and concentrated under reduced pressure. The residue was purified by column chromatography on silica gel to afford compound 32b (yield: 35%). MS (ESI): m/z 284.3 (M+H)$^+$.

Step 3: To a mixture of compound 32b (1.0 eq) and tosylmethyl isocyanide (2.0 eq) in 1,2-dimethoxyethane/MeOH (v/v, 16/1), potassium tert-butoxide (3.0 eq) was added at 0-5° C. The mixture was stirred at r.t. for 4 h. The mixture was poured into water and the whole solution was adjusted to pH=6-7 by 1N HCl solution. The mixture was extracted with EtOAc three times. The combined organic layers were washed with brine, dried over Na$_2$SO$_4$, filtered and concentrated under reduced pressure. The residue was purified by column chromatography on silica gel to give compound 32c (yield: 20%). MS (ESI): m/z 295.3 (M+H)$^+$.

Step 4: To a solution of compound 32c (1.0 eq) in ethanol was added NaOH (40% w/w in water, 10.0 eq) and the mixture was stirred at 95° C. for 3 h. The mixture was diluted with water and the whole solution was adjusted to pH=1-2 by 4N HCl solution. The mixture was extracted with EtOAc three times. The combined organic layers were washed with brine, dried over Na$_2$SO$_4$, filtered and concentrated under reduced pressure to give 32d (yield: 82%), which was used to the next step directly. MS (ESI): m/z 314.3 (M+H)$^+$.

Step 5: To a solution of compound 32d (1.0 eq) in ethyl acetate were subsequently added pyridine (3.0 eq) and 2,4,6-Tripropyl-1,3,5,2,4,6-Trioxatriphosphorinane-2,4,6-Trioxide (2.5 eq) and the mixture was stirred at r.t. for 10 min. 4-chlorobenzylamine (3.0 eq) was added to the above mixture and the resulting reaction mixture was stirred at r.t. for 16 h. The mixture was quenched by 2N NaOH solution and diluted with water. The resulting mixture was extracted with EtOAc three times. The combined organic layers were dried over Na$_2$SO$_4$, filtered and concentrated under reduced pressure. The residue was purified by Prep-HPLC to give compound 32 as a white solid.

Compound 33, 34, 35, 36, 37 was prepared using the similar procedures as described for compound 32.

| Compound | Structure | LCMS (M + H)+ | NMR |
|---|---|---|---|
| 32 | 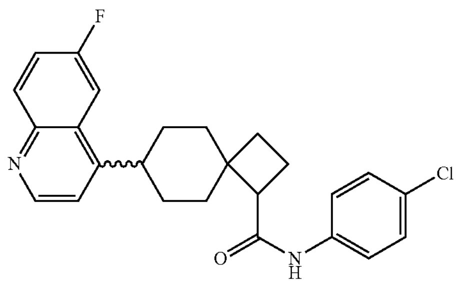 | 424.15 | ¹H NMR (500 MHz, d₆-DMSO) δ 10.27 (s, 1H), 8.81 (s, 1H), 8.11-8.05 (m, 1H), 8.02 (d, J = 11.0 Hz, 1H), 7.69-7.63 (m, 3H), 7.38-7.31 (m, 3H), 3.38-3.20 (m, 1H), 2.78 (d, J = 6.8 Hz, 1H), 2.20 (t, J = 12.0 Hz, 1H), 1.97 (dd, J = 13.9, 6.8 Hz, 1H), 1.84-1.55 (m, 8H), 1.35-1.26 (m, 2H). |
| 33 | 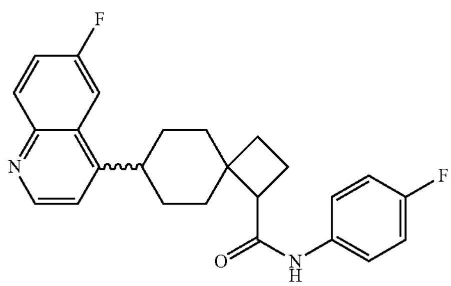 | 407.19 | ¹H NMR (500 MHz, d₆-DMSO) δ 10.27 (s, 1H), 8.82 (s, 1H), 8.09-8.02 (m, 1H), 7.93 (d, J = 11.2 Hz, 1H), 7.73-7.52 (m, 3H), 7.56-7.43 (m, 3H), 3.30-3.10 (m, 1H), 2.77 (d, J = 6.6 Hz, 1H), 2.21 (t, J = 11.4 Hz, 1H), 1.96 (dd, J = 13.3, 6.6 Hz, 1H), 1.87-1.50 (m, 8H), 1.36-1.25 (m, 2H). |
| 34 | 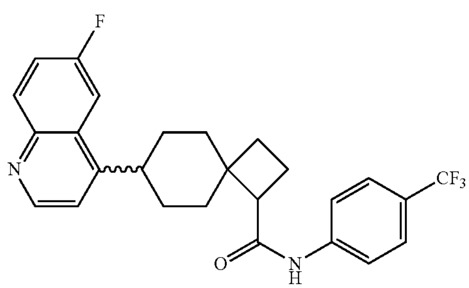 | 457.23 | ¹H NMR (500 MHz, d₆-DMSO) δ 10.07 (s, 1H), 8.78 (s, 1H), 8.14-8.08 (m, 1H), 8.03 (d, J = 11.0 Hz, 1H), 7.63-7.58 (m, 3H), 7.48-7.41 (m, 3H), 3.34-3.16 (m, 1H), 2.73 (d, J = 6.8 Hz, 1H), 2.24 (t, J = 12.0 Hz, 1H), 1.92 (dd, J = 13.9, 6.8 Hz, 1H), 1.81-1.51 (m, 8H), 1.32-1.23 (m, 2H). |
| 35 | 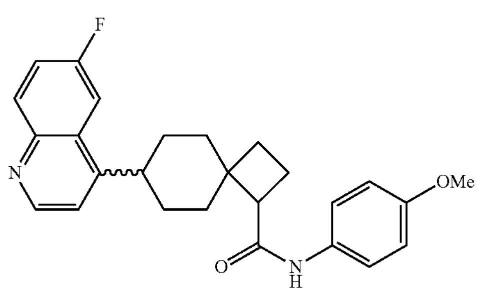 | 419.21 | ¹H NMR (500 MHz, d₆-DMSO) δ 10.13 (s, 1H), 8.80 (s, 1H), 8.03-7.98 (m, 2H), 7.67 (d, J = 8.4 Hz, 1H), 7.44 (d, J = 5.1 Hz, 1H), 7.25 (d, J = 8.3 Hz, 2H), 6.66 (d, J = 8.8 Hz, 2H), 3.78 (s, 3H), 3.30-3.10 (m, 1H), 2.72 (d, J = 6.1 Hz, 1H), 2.21 (t, J = 11.4 Hz, 1H), 1.91 (dd, J = 13.3, 6.6 Hz, 1H), 1.81-1.52 (m, 8H), 1.50-1.25 (m, 2H). |
| 36 | 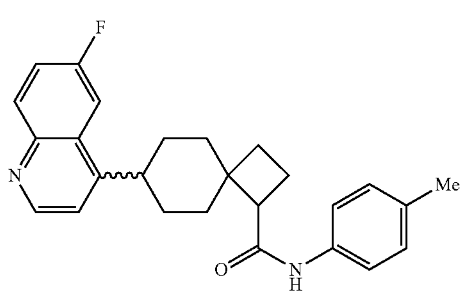 [SMILES: Cc1ccc(NC(=O)C2CCC23CCC(c2ccnc4ccc(F)cc24)CC3)cc1] | 403.21 | ¹H NMR (500 MHz, d₆-DMSO) δ 10.12 (s, 1H), 8.83 (s, 1H), 8.22-8.07 (m, 1H), 8.01 (d, J = 11.0 Hz, 1H), 7.73-7.65 (m, 3H), 7.53-7.46 (m, 3H), 3.39-3.18 (m, 1H), 2.77 (d, J = 6.9 Hz, 1H), 2.29 (t, J = 12.0 Hz, 1H), 2.20 (s, 3H), 1.82 (dd, J = 13.6, 6.6 Hz, 1H), 1.80-1.44 (m, 8H), 1.30-1.18 (m, 2H). |

| Compound | Structure | LCMS (M + H)+ | NMR |
|---|---|---|---|
| 37 | 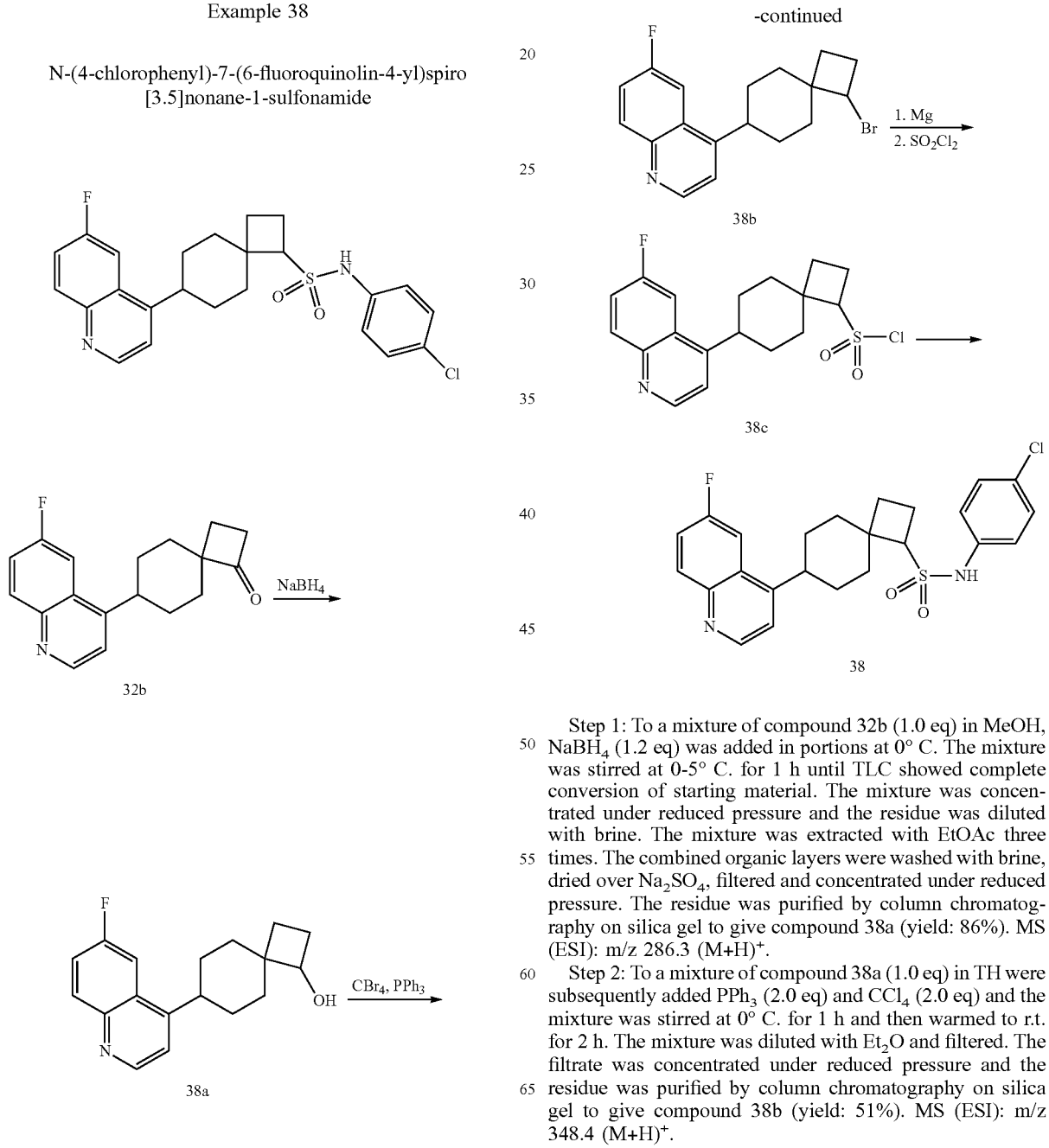 | 414.19 | $^1$H NMR (500 MHz, d$_6$-DMSO) δ 10.43 (s, 1H), 8.92 (s, 1H), 8.13-8.04 (m, 2H), 7.72 (d, J = 8.1 Hz, 1H), 7.24 (d, J = 5.2 Hz, 1H), 7.15 (d, J = 8.1 Hz, 2H), 6.63 (d, J = 8.2 Hz, 2H), 3.31-3.10 (m, 1H), 2.73 (d, J = 6.3 Hz, 1H), 2.25 (t, J = 11.1 Hz, 1H), 1.96 (dd, J = 13.1, 6.2 Hz, 1H), 1.83-1.58 (m, 8H), 1.53-1.21 (m, 2H). |

Example 38

N-(4-chlorophenyl)-7-(6-fluoroquinolin-4-yl)spiro[3.5]nonane-1-sulfonamide

Step 1: To a mixture of compound 32b (1.0 eq) in MeOH, NaBH$_4$ (1.2 eq) was added in portions at 0° C. The mixture was stirred at 0-5° C. for 1 h until TLC showed complete conversion of starting material. The mixture was concentrated under reduced pressure and the residue was diluted with brine. The mixture was extracted with EtOAc three times. The combined organic layers were washed with brine, dried over Na$_2$SO$_4$, filtered and concentrated under reduced pressure. The residue was purified by column chromatography on silica gel to give compound 38a (yield: 86%). MS (ESI): m/z 286.3 (M+H)$^+$.

Step 2: To a mixture of compound 38a (1.0 eq) in TH were subsequently added PPh$_3$ (2.0 eq) and CCl$_4$ (2.0 eq) and the mixture was stirred at 0° C. for 1 h and then warmed to r.t. for 2 h. The mixture was diluted with Et$_2$O and filtered. The filtrate was concentrated under reduced pressure and the residue was purified by column chromatography on silica gel to give compound 38b (yield: 51%). MS (ESI): m/z 348.4 (M+H)$^+$.

Step 3: To a suspension of magnesium turning (1.7 eq) in dry Et$_2$O, compound 38b (1.0 eq) in dry Et$_2$O was added in portions. After the end of reaction exothermic, the mixture was heated refluxed for 30 min. The resulting suspension was cooled to 0° C., sulfuryl chloride (3.0 eq) in dry DCM was added dropwise. The mixture was warmed to 25° C. and concentrated under reduced pressure. The residue was diluted with water and extracted with n-hexane three times. The combined organic layers were concentrated under reduced pressure to give compound 38c, which was used to the next step directly.

Step 4: To a solution of compound 38c (1.0 eq) in dry DCM were subsequently added 4-chloro aniline (1.0 eq) and TEA (1.1 eq) at 0° C. and the mixture was stirred at 25° C. for 30 min. The mixture was concentrated under reduced pressure. The residue was purified by Prep-HPLC to give compound 38 as a white solid. MS (ESI): m/z 459.4 (M+H)$^+$.

Compound 39, 40, 41, 42, 43 was prepared using the similar procedures as described for compound 38.

| Compound | Structure | LCMS (M + H)+ | NMR |
|---|---|---|---|
| 38 | 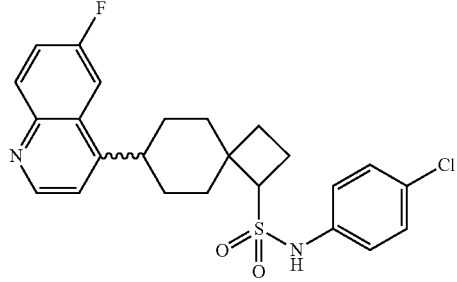 | 460.17 | $^1$H NMR (500 MHz, d$_6$-DMSO) δ 10.12 (s, 1H), 8.82 (d, J = 5.1 Hz, 1H), 8.15-8.07 (m, 2H), 7.63-7.46 (m, 3H), 7.38-7.31 (m, 3H), 3.38-3.20 (m, 1H), 2.78 (d, J = 6.8 Hz, 1H), 2.20 (t, J = 12.0 Hz, 1H), 1.97 (dd, J = 13.9, 6.8 Hz, 1H), 1.84-1.55 (m, 8H), 1.35-1.26 (m, 2H). |
| 40 | 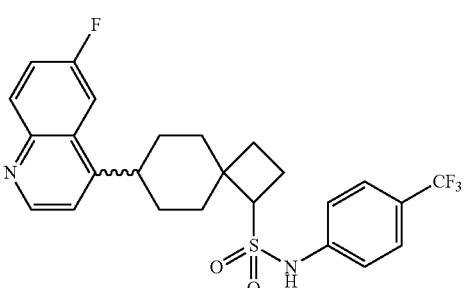 | 493.15 | $^1$H NMR (500 MHz, d$_6$-DMSO) δ 10.17 (s, 1H), 8.85 (d, J = 5.1 Hz, 1H), 8.16-8.03 (m, 2H), 7.66-7.48 (m, 3H), 7.41-7.35 (m, 3H), 3.42-3.25 (m, 1H), 2.82 (d, J = 6.7 Hz, 1H), 2.24 (t, J = 12.1 Hz, 1H), 1.95 (dd, J = 13.5, 6.6 Hz, 1H), 1.88-1.52 (m, 8H), 1.37-1.21 (m, 2H). |
| 42 | 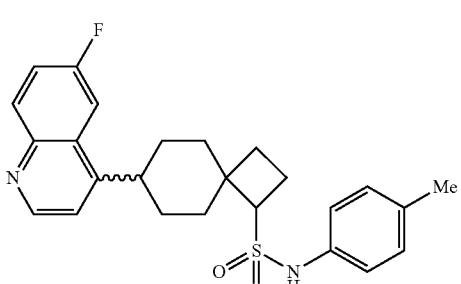 | 439.23 | $^1$H NMR (500 MHz, d$_6$-DMSO) δ 10.07 (s, 1H), 8.78 (d, J = 5.2 Hz, 1H), 8.07-7.92 (m, 2H), 7.51 (d, J = 8.3 Hz, 1H), 7.44 (d, J = 5.1 Hz, 1H), 7.33 (d, J = 8.1 Hz, 2H), 6.95 (d, J = 8.1 Hz, 2H), 3.39-3.18 (m, 1H), 3.11-3.09 (m, 1H), 2.45-2.25 (m, 2H), 2.21 (s, 3H), 2.15-2.05 (m, 2H), 1.80-1.54 (m, 8H). |

Example 50

N-(4-chlorophenyl)-7-(6-fluoroquinolin-4-yl)-1-oxaspiro[3.5]nonane-3-carboxamide

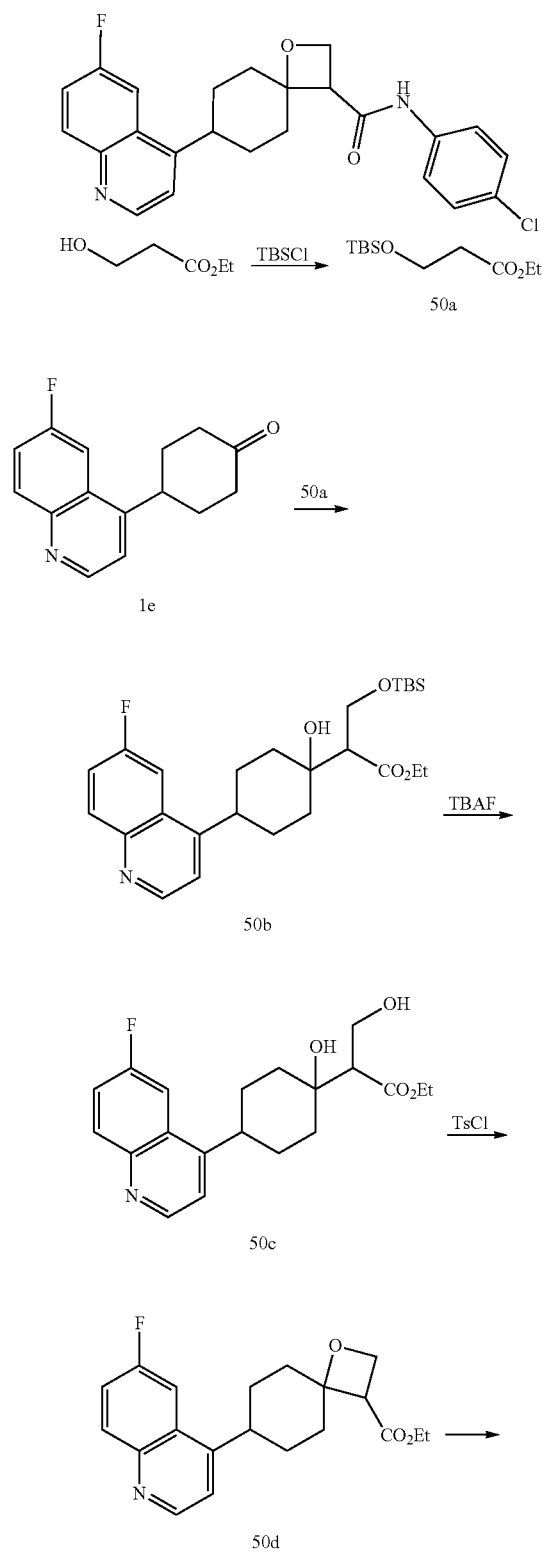

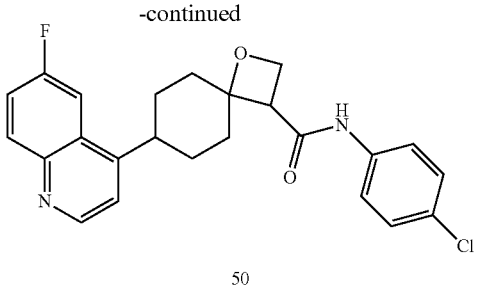

Step 1: To a solution of ethyl 3-hydroxypropanoate (1.0 eq) in dry DCM was added imidazole (1.5 eq). The mixture was cooled to 0° C. and TBSCl (1.2 eq) was added. The resulting mixture was stirred at r.t. for 2 h. The reaction was quenched by aq. NH$_4$Cl solution. The mixture was extracted with ethyl acetate three times and the combined organic layers were washed with brine, dried over Na$_2$SO$_4$, filtered and concentrated under reduced pressure. The residue was purified by column chromatography on silica gel to give compound 50a (yield: 88%).

Step 2: To a mixture of diisopropylamine (2.0 eq) in dry THF at −78° C., n-BuLi (2.5 M, 2.0 eq) was added dropwise under N$_2$, followed by a solution of compound 50a (2.0 eq) in THF. After the mixture was stirred at −78° C. for 1 h, a solution of compound 1e (1.0 eq) in dry THF was added dropwise. The resulting mixture was warmed to r.t. for 3 h. The reaction was quenched by aq. NH$_4$Cl solution. The mixture was extracted with ethyl acetate three times and the combined organic layers were washed with brine, dried over Na$_2$SO$_4$, filtered and concentrated under reduced pressure. The residue was purified by column chromatography on silica gel to give compound 50b (yield: 54%). MS (ESI): m/z 476.4 (M+H)$^+$.

Step 3: To a mixture of compound 50b (1.0 eq) in THF was added TBAF (1.0 M in THF, 10.0 eq), and the mixture was stirred at 60° C. for 4 h. The mixture was diluted with water and extracted with ethyl acetate three times and the combined organic layers were washed with brine, dried over Na$_2$SO$_4$, filtered and concentrated under reduced pressure to give compound 50c (yield: 76%), which was used to the next step directly. MS (ESI): m/z 362.3 (M+H)$^+$.

Step 4: To a mixture of compound 50c (1.0 eq) in pyridine was added p-toluenesulfonyl chloride (1.5 eq), and the mixture was stirred at 80° C. for 16 h. The mixture was concentrated under reduced pressure. The residue was purified by column chromatography on silica gel to give compound 50d (yield: 41%). MS (ESI): m/z 344.4 (M+H)$^+$.

Step 5: To a mixture of 4-chloroaniline (4.0 eq) in dry THF at 0° C., isopropylmagnesium chloride solution (2.0 M in THF, 4.0 eq) was added. After the mixture was stirred at r.t. for 5 m, a solution of compound 50d (1.0 eq) in dry THF was added. The resulting mixture was stirred at r.t. for 16 h. The reaction mixture was quenched by aq. N$_4$Cl solution. The mixture was extracted with ethyl acetate three times and the combined organic layers were dried over Na$_2$SO$_4$, filtered and concentrated under reduced pressure. The residue was purified by Prep-HPLC to give compound 50 as a white solid.

Compound 51, 52, 53, 54, 55 was prepared using the similar procedures as described for compound 50.

| Compound | Structure | LCMS (M + H)+ | NMR |
|---|---|---|---|
| 50 | 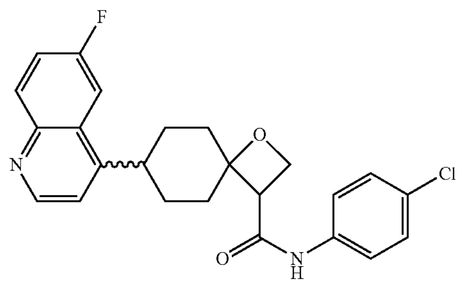 [SMILES: O=C(Nc1ccc(Cl)cc1)C1COC12CCC(c1ccnc3ccc(F)cc13)CC2] | 426.17 | ¹H NMR (500 MHz, d₆-DMSO) δ 10.22 (s, 1H), 8.78 (d, J = 5.1 Hz, 1H), 7.94-7.91 (m, 2H), 7.76 (d, J = 8.1 Hz, 2H), 7.51 (d, J = 8.0 Hz, 1H), 7.40-7.37 (m, 3H), 4.02 (dd, J = 14.1, 7.0 Hz, 1H), 3.89 (dd, J = 14.1, 2.6 Hz, 1H), 3.20-3.13 (m, 1H), 3.10 (dd, J = 7.0, 2.6 Hz, 1H), 2.15-2.08 (m, 1H), 2.00-1.95 (m, 1H), 1.83-1.75 (m, 3H), 1.70-1.45 (m, 3H) |
| 51 | 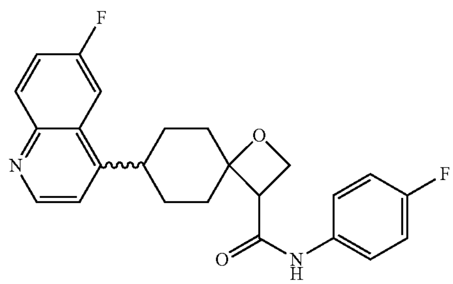 [SMILES: O=C(Nc1ccc(F)cc1)C1COC12CCC(c1ccnc3ccc(F)cc13)CC2] | 409.17 | ¹H NMR (500 MHz, d₆-DMSO) δ 10.22 (s, 1H), 8.78 (d, J = 5.1 Hz, 1H), 7.94-7.91 (m, 2H), 7.76 (d, J = 8.1 Hz, 2H), 7.51 (d, J = 8.0 Hz, 1H), 7.40-7.37 (m, 3H), 4.02 (dd, J = 14.1, 7.0 Hz, 1H), 3.89 (dd, J = 14.1, 2.6 Hz, 1H), 3.20-3.13 (m, 1H), 3.10 (dd, J = 7.0, 2.6 Hz, 1H), 2.15-2.08 (m, 1H), 2.00-1.95 (m, 1H), 1.83-1.75 (m, 3H), 1.70-1.45 (m, 3H) |
| 52 | 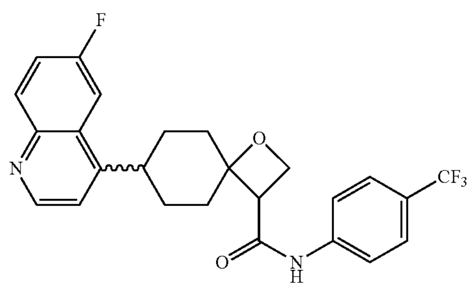 [SMILES: O=C(Nc1ccc(C(F)(F)F)cc1)C1COC12CCC(c1ccnc3ccc(F)cc13)CC2] | 459.21 | ¹H NMR (500 MHz, d₆-DMSO) δ 10.25 (s, 1H), 8.82 (d, J = 5.3 Hz, 1H), 7.97-7.90 (m, 2H), 7.78 (d, J = 8.2 Hz, 2H), 7.55 (d, J = 8.3 Hz, 1H), 7.44-7.38 (m, 3H), 4.05 (dd, J = 14.3, 7.2 Hz, 1H), 3.93 (dd, J = 14.3, 2.7 Hz, 1H), 3.23-3.15 (m, 1H), 3.13 (dd, J = 7.2, 2.7 Hz, 1H), 2.18-2.07 (m, 1H), 2.01-1.97 (m, 1H), 1.84-1.70 (m, 3H), 1.66-1.45 (m, 3H) |
| 53 | 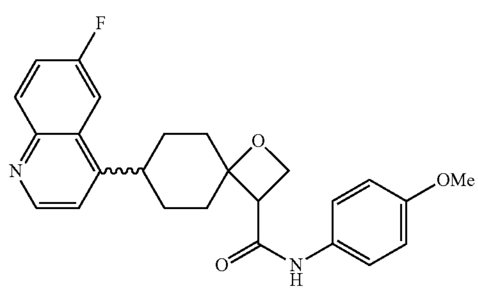 [SMILES: COc1ccc(NC(=O)C2COC23CCC(c2ccnc4ccc(F)cc24)CC3)cc1] | 421.19 | ¹H NMR (500 MHz, d₆-DMSO) δ 10.22 (s, 1H), 8.78 (d, J = 5.1 Hz, 1H), 7.94-7.91 (m, 2H), 7.76 (d, J = 8.1 Hz, 2H), 7.51 (d, J = 8.0 Hz, 1H), 7.40-7.37 (m, 3H), 4.02 (dd, J = 14.1, 7.0 Hz, 1H), 3.89 (dd, J = 14.1, 2.6 Hz, 1H), 3.77 (s, 3H), 3.20-3.13 (m, 1H), 3.10 (dd, J = 7.0, 2.6 Hz, 1H), 2.15-2.08 (m, 1H), 2.00-1.95 (m, 1H), 1.83-1.75 (m, 3H), 1.70-1.45 (m, 3H) |
| 54 | 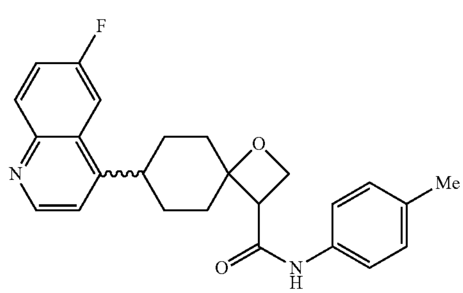 [SMILES: Cc1ccc(NC(=O)C2COC23CCC(c2ccnc4ccc(F)cc24)CC3)cc1] | 405.21 | ¹H NMR (500 MHz, d₆-DMSO) δ 10.10 (s, 1H), 8.80 (d, J = 5.4 Hz, 1H), 8.01-7.92 (m, 2H), 7.71 (d, J = 8.0 Hz, 2H), 7.48 (d, J = 8.1 Hz, 1H), 7.44-7.36 (m, 3H), 4.01 (dd, J = 14.3, 7.2 Hz, 1H), 3.90 (dd, J = 14.2, 2.8 Hz, 1H), 3.25-3.12 (m, 1H), 3.13 (dd, J = 7.3, 2.8 Hz, 1H), 2.22 (s, 3H), 2.19-2.04 (m, 1H), 1.99-1.94 (m, 1H), 1.81-1.66 (m, 3H), 1.63-1.37 (m, 3H) |

| Compound | Structure | LCMS (M + H)+ | NMR |
|---|---|---|---|
| 55 | 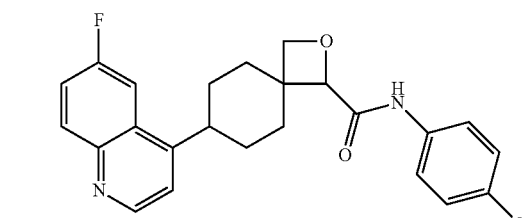 | 416.17 | $^1$H NMR (500 MHz, d$_6$-DMSO) δ 10.22 (s, 1H), 8.78 (d, J = 5.1 Hz, 1H), 7.94-7.91 (m, 2H), 7.76 (d, J = 8.1 Hz, 2H), 7.51 (d, J = 8.0 Hz, 1H), 7.40-7.37 (m, 3H), 4.02 (dd, J = 14.1, 7.0 Hz, 1H), 3.89 (dd, J = 14.1, 2.6 Hz, 1H), 3.20-3.13 (m, 1H), 3.10 (dd, J = 7.0, 2.6 Hz, 1H), 2.15-2.08 (m, 1H), 2.00-1.95 (m, 1H), 1.83-1.75 (m, 3H), 1.70-1.45 (m, 3H) |

Example 62

N-(4-chlorophenyl)-7-(6-fluoroquinolin-4-yl)-2-oxaspiro[3.5]nonane-1-carboxamide

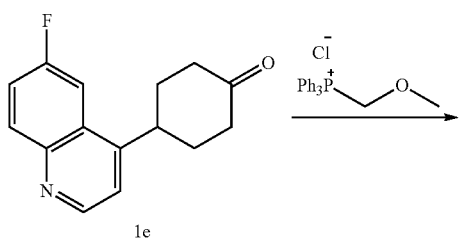

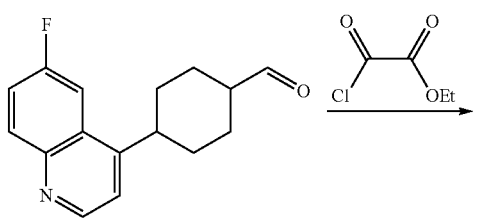

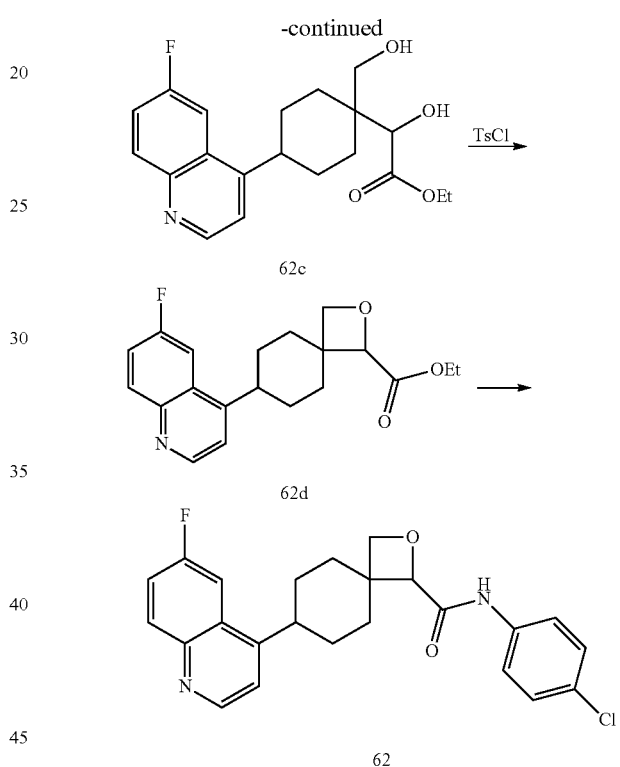

Step 1: To a mixture of (methoxymethyl)triphenylphodphonium chloride (1.1 eq) in dry THF at −78° C., LiHMDS (1 M in THF, 1.1 eq) was added dropwise. After the mixture was stirred at −78° C. for 2 h, compound 1e (1.0 eq) in THF was added to the above solution. The resulting mixture was warmed to r.t. for 16 h. The mixture was quenched with 2N HCl solution and the resulting mixture was stirred for 1 h. The mixture was extracted with ethyl acetate three times and the combined organic layers were washed with brine, dried over Na$_2$SO$_4$, filtered and concentrated under reduced pressure. The residue was purified by column chromatography on silica gel to give compound 62a (yield: 90%).

Step 2: To a mixture of diisopropylamine (2.0 eq) in dry THF at −78° C., n-BuLi (2.5 M in hexane, 2.0 eq) was added dropwise under N$_2$, followed by the addition of a solution of compound 62a (1.0 eq) in THF. After the mixture was stirred at −78° C. for 1 h, a solution of ethyl oxalyl monochloride (1.0 eq) in dry THF was added. The resulting mixture was warmed to r.t. for 3 h. The reaction was quenched by aq.

NH₄Cl solution. The mixture was extracted with ethyl acetate three times and the combined organic layers were washed with brine, dried over Na₂SO₄, filtered and concentrated under reduced pressure. The residue was purified by column chromatography on silica gel to give compound 62b (yield: 51%). MS (ESI): m/z 358.4 (M+H)⁺.

Step 3: To a mixture of compound 62b (1.0 eq) in EtOH, NaBH₄ (2.0 eq) was added at −18° C. The mixture was stirred at −18° C. for 30 min. The reaction was quenched by aq. NH₄Cl solution. The mixture was extracted with ethyl acetate three times and the combined organic layers were washed with brine, dried over Na₂SO₄, filtered and concentrated under reduced pressure. The residue was purified by column chromatography on silica gel to give compound 62c (yield: 83%). MS (ESI): m/z 362.4 (M+H)⁺.

Step 4: To a mixture of compound 62c (1.0 eq) in pyridine was added p-toluenesulfonyl chloride (1.5 eq), and the mixture was stirred at 80° C. for 16 h. The mixture was concentrated under reduced pressure. The residue was purified by column chromatography on silica gel to give compound 62d (yield: 50%). MS (ESI): m/z 344.4 (M+H)⁺.

Step 5: To a mixture of 4-chloroaniline (4.0 eq) in dry THF at 0° C., isopropylmagnesium chloride solution (2.0 M in THF, 4.0 eq) was added. After the mixture was stirred at r.t. for 5 min, a solution of compound 62d (1.0 eq) in dry THF was added. The resulting mixture was stirred at r.t. for 16 h. The reaction mixture was quenched by aq. NH₄Cl solution. The mixture was extracted with ethyl acetate three times and the combined organic layers were dried over Na₂SO₄, filtered and concentrated under reduced pressure. The residue was purified by Prep-HPLC to give compound 62 as a white solid.

Compound 63, 64, 65, 66, 67 was prepared using the similar procedures as described for compound 62.

| Compound | Structure | LCMS (M + H)+ | NMR |
|---|---|---|---|
| 62 | 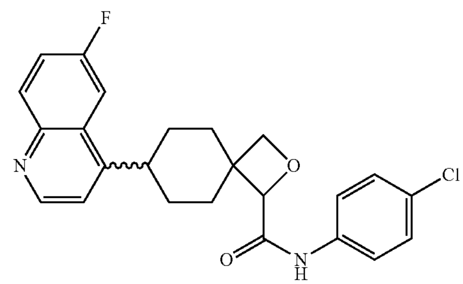 [SMILES: O=C(Nc1ccc(Cl)cc1)C1OCC12CCC(c1ccnc3ccc(F)cc13)CC2] | 426.13 | ¹H NMR (500 MHz, d₆-DMSO) δ 10.21 (s, 1H), 8.82 (d, J = 5.3 Hz, 1H), 7.99-7.94 (m, 2H), 7.68-7.44 (m, 3H), 7.40 (d, J = 5.0 Hz, 1H), 7.02 (d, J = 8.1 Hz, 2H), 4.82 (s, 1H), 3.92 (d, J = 16.1 Hz, 1H), 3.87 (d, J = 16.2 Hz, 1H), 3.22-3.10 (m, 1H), 1.98-1.54 (m, 8H). |
| 63 | 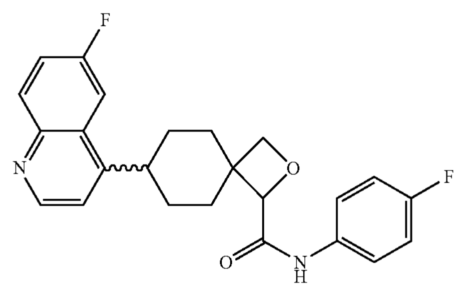 [SMILES: O=C(Nc1ccc(F)cc1)C1OCC12CCC(c1ccnc3ccc(F)cc13)CC2] | 409.17 | ¹H NMR (500 MHz, d₆-DMSO) δ 10.21 (s, 1H), 8.82 (d, J = 5.3 Hz, 1H), 7.99-7.94 (m, 2H), 7.68-7.44 (m, 3H), 7.40 (d, J = 5.0 Hz, 1H), 7.02 (d, J = 8.1 Hz, 2H), 4.82 (s, 1H), 3.92 (d, J = 16.1 Hz, 1H), 3.87 (d, J = 16.2 Hz, 1H), 3.22-3.10 (m, 1H), 1.98-1.54 (m, 8H). |
| 64 | 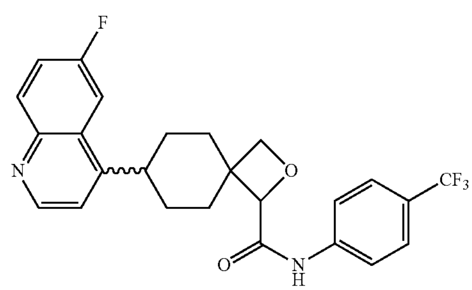 [SMILES: O=C(Nc1ccc(C(F)(F)F)cc1)C1OCC12CCC(c1ccnc3ccc(F)cc13)CC2] | 459.17 | ¹H NMR (500 MHz, d₆-DMSO) δ 10.17 (s, 1H), 8.80 (d, J = 5.1 Hz, 1H), 7.94-7.87 (m, 2H), 7.62-7.38 (m, 3H), 7.33 (d, J = 5.2 Hz, 1H), 7.01 (d, J = 8.2 Hz, 2H), 4.86 (s, 1H), 3.94 (d, J = 16.3 Hz, 1H), 3.88 (d, J = 16.1 Hz, 1H), 3.23-3.10 (m, 1H), 1.97-1.51 (m, 8H). |
| 65 | 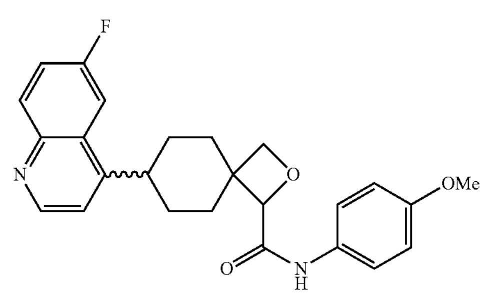 [SMILES: COc1ccc(NC(=O)C2OCC23CCC(c2ccnc4ccc(F)cc24)CC3)cc1] | 421.19 | ¹H NMR (500 MHz, d₆-DMSO) δ 10.21 (s, 1H), 8.82 (d, J = 5.3 Hz, 1H), 7.99-7.94 (m, 2H), 7.68-7.44 (m, 3H), 7.40 (d, J = 5.0 Hz, 1H), 7.02 (d, J = 8.1 Hz, 2H), 4.82 (s, 1H), 3.92 (d, J = 16.1 Hz, 1H), 3.87 (d, J = 16.2 Hz, 1H), 3.72 (s, 3H), 3.22-3.10 (m, 1H), 1.98-1.54 (m, 8H). |

-continued

| Compound | Structure | LCMS (M + H)+ | NMR |
|---|---|---|---|
| 66 | 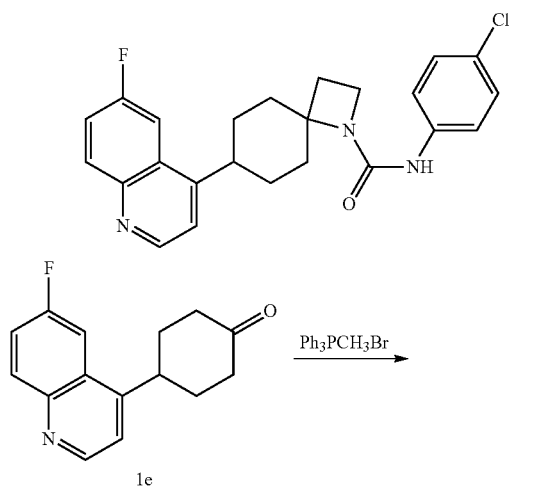 | 405.19 | $^1$H NMR (500 MHz, $d_6$-DMSO) δ 10.19 (s, 1H), 8.69 (d, J = 5.1 Hz, 1H), 7.96-7.90 (m, 2H), 7.47 (d, J = 8.1 Hz, 1H), 7.38 (d, J = 5.2 Hz, 1H), 7.29 (d, J = 8.1 Hz, 2H), 6.95 (d, J = 8.1 Hz, 2H), 4.84 (s, 1H), 3.95 (d, J = 16.0 Hz, 1H), 3.79 (d, J = 16.2 Hz, 1H), 3.25-3.13 (m, 1H), 2.21 (s, 3H), 1.98-1.54 (m, 8H). |
| 67 | 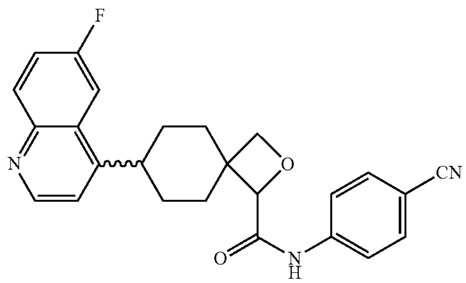 [SMILES: N#Cc1ccc(NC(=O)C2OCC23CCC(c2ccnc4ccc(F)cc24)CC3)cc1] | 416.17 | $^1$H NMR (500 MHz, $d_6$-DMSO) δ 10.21 (s, 1H), 8.82 (d, J = 5.3 Hz, 1H), 7.99-7.94 (m, 2H), 7.68-7.44 (m, 3H), 7.40 (d, J = 5.0 Hz, 1H), 7.02 (d, J = 8.1 Hz, 2H), 4.82 (s, 1H), 3.92 (d, J = 16.1 Hz, 1H), 3.87 (d, J = 16.2 Hz, 1H), 3.22-3.10 (m, 1H), 1.98-1.54 (m, 8H). |

Example 68

N-(4-chlorophenyl)-7-(6-fluoroquinolin-4-yl)-1-azaspiro[3.5]nonane-1-carboxamide

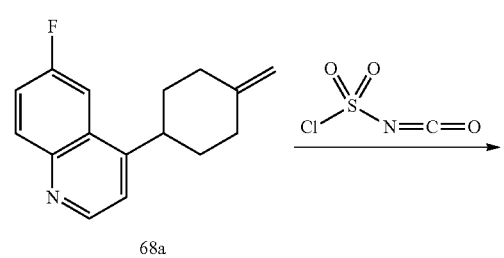

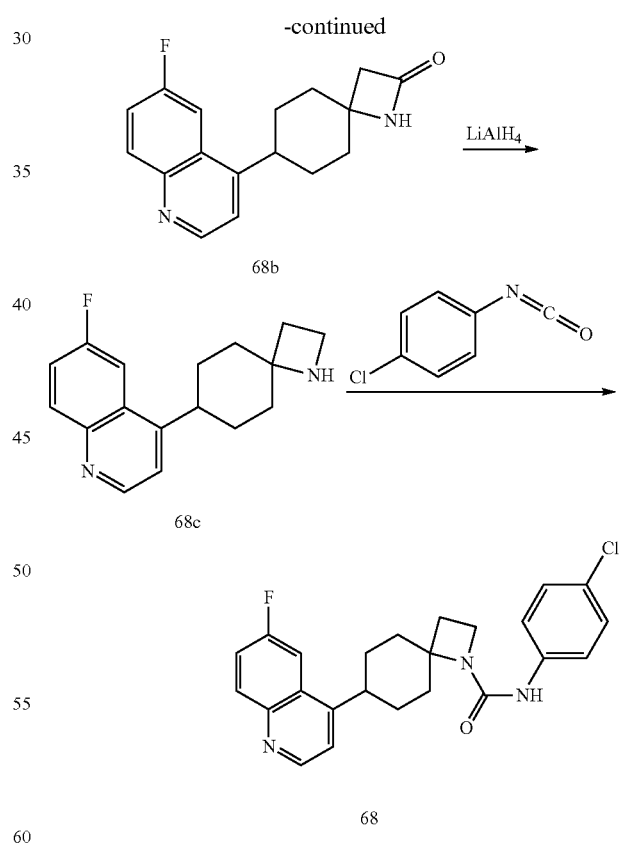

Step 1: To a suspension of methyltriphenylphosphonium bromide (1.5 eq) in dry THF at 0° C., n-BuLi (2.5 M in hexane, 1.3 eq) was added. The mixture was stirred at r.t. for 4 h. Compound 1e (1.0 eq) in dry THF was added to the above solution and the resulting mixture was stirred at r.t. for 16 h. The reaction was quenched by aq. NH$_4$Cl solution. The mixture was extracted with ethyl acetate three times and the combined organic layers were washed with brine, dried over Na₂SO₄, filtered and concentrated under reduced pressure. The residue was purified by column chromatography on silica gel to give compound 68a (yield: 90%). MS (ESI): m/z 268.3 (M+H)⁺.

Step 2: To a solution of compound 68a (1.0 eq) in Et₂O at 0° C. was added chlorosulfonyl isocyanate (1.0 eq) and the mixture was stirred at r.t. for 20 h. Saturated Na₂SO₃ solution and 10% KOH solution were subsequently added to the reaction mixture and the resulting mixture was stirred for 1 h. The mixture was extracted with ethyl acetate three times and the combined organic layers were washed with brine, dried over Na₂SO₄, filtered and concentrated under reduced pressure. The residue was purified by column chromatography on silica gel to give compound 68b (yield: 56%). MS (ESI): m/z 285.3 (M+H)⁺.

Step 3: To a solution of compound 68b (1.0 eq) in THF at 0° C. was added LiAlH₄ (2.0 eq) and the mixture was stirred at r.t. for 2 h. Water (2 eq) and Na₂SO₄ were subsequently added to the reaction mixture and the resulting suspension was filtered. The filter cake was washed with EtOAc and the filtrate was concentrated under reduced pressure. The residue was purified by column chromatography on silica gel to give compound 68c (yield: 75%). MS (ESI): m/z 271.3 (M+H)⁺.

Step 4: To a solution of compound 68c (1.0 eq) in THF (10 mL) at 0° C. was added triethyl amine (3.0 eq), followed by the addition of 4-chlorophenyl isocyanate (1.0 eq) and the mixture was stirred at r.t. for 3 h. The mixture was quenched by aq. N₄C and extracted with EtOAc three times. The combined organic layers were washed with brine, dried over Na₂SO₄, filtered and concentrated under reduced pressure. The residue was purified by Prep-HPLC to give compound 68 as a white solid. MS (ESI): m/z 424.4 (M+H)⁺.

Compound 69, 70, 71, 72, 73 was prepared using the similar procedures as described for compound 68.

| Compound | Structure | LCMS (M + H)+ | NMR |
|---|---|---|---|
| 68 | 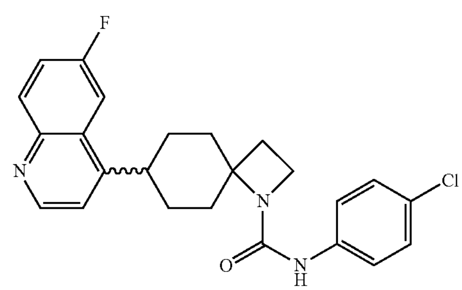 [SMILES: O=C(Nc1ccc(Cl)cc1)N1CCC12CCC(c1ccnc3ccc(F)cc13)CC2] | 425.15 | ¹H NMR (500 MHz, d₆-DMSO) δ 10.07 (s, 1H), 8.71 (s,1H), 8.01-7.95 (m, 2H), 7.76 (d, J = 8.0 Hz, 2H), 7.53 (d, J = 8.1 Hz, 1H), 7.49-7.33 (m, 3H), 3.51 (dd, J = 13.8, 9.0 Hz, 2H), 3.28-3.10 (m, 1H), 1.98(dd, J = 9.0, 6.6 Hz, 2H), 1.84-1.65 (m, 8H) |
| 70 | 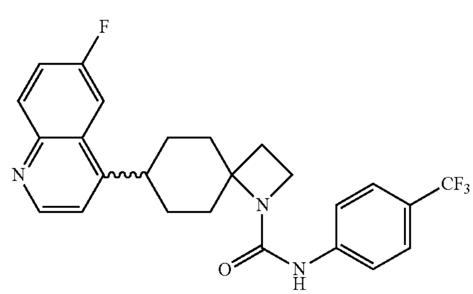 [SMILES: O=C(Nc1ccc(C(F)(F)F)cc1)N1CCC12CCC(c1ccnc3ccc(F)cc13)CC2] | 458.18 | ¹H NMR (500 MHz, d₆-DMSO) δ 1007 (s, 1H), 8.71 (s,1H), 8.01-7.95 (m, 2H), 7.76 (d, J = 8.0 Hz, 2H), 7.53 (d, J = 8.1 Hz, 1H), 7.49-7.33 (m, 3H), 3.51 (dd, J = 13.8, 9.0 Hz, 2H), 3.28-3.10 (m, 1H), 1.98(dd, J = 9.0, 6.6 Hz, 2H), 1.84-1.65 (m, 8H) |
| 72 | 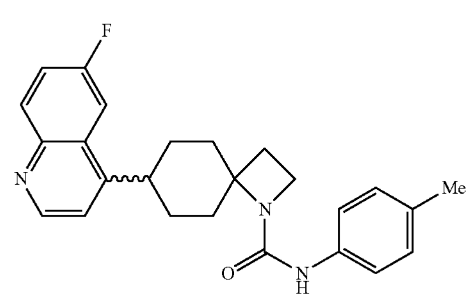 [SMILES: Cc1ccc(NC(=O)N2CCC23CCC(c2ccnc4ccc(F)cc24)CC3)cc1] | 404.21 | ¹H NMR (500 MHz, d₆-DMSO) δ 10.01 (s, 1H), 8.75 (s, 1H), 8.00-7.94 (m, 2H), 7.71 (d, J = 8.0 Hz, 2H), 7.51 (d, J = 8.1 Hz, 1H), 7.47-7.35 (m, 3H), 3.53 (dd, J = 13.5, 9.1 Hz, 2H), 3.25-3.12 (m, 1H), 2.22 (s, 3H), 1.96 (dd, J = 9.1, 6.3 Hz, 2H), 1.87-1.64 (m, 8H) |

Example 74

N-(4-chlorophenyl)-7-(6-fluoroquinolin-4-yl)-1-azaspiro[3.5]nonane-1-sulfonamide

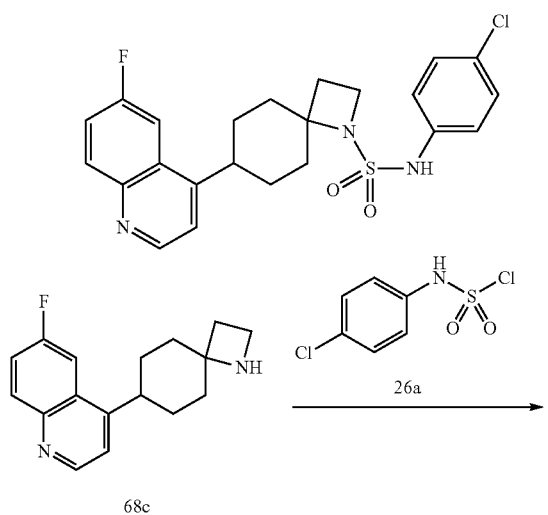

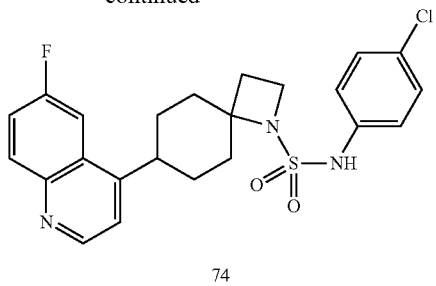

74

To a solution of compound 68c (1.0 eq) in THF (10 mL) at 0° C. was added triethyl amine (2.0 eq), followed by compound 26a (1.2 eq) and the mixture was stirred at r.t. for 3 h. The mixture was quenched by aq. NH$_4$Cl and extracted with EtOAc three times. The combined organic layers were washed with brine, dried over dried over Na$_2$SO$_4$, filtered and concentrated under reduced pressure. The residue was purified by Prep-HPLC to give compound 74 as a white solid. MS (ESI): m/z 460.4 (M+H)$^+$.

Compound 75, 76, 77, 78, 79 was prepared using the similar procedures as described for compound 74.

| Compound | Structure | LCMS (M + H)+ | NMR |
|---|---|---|---|
| 74 | 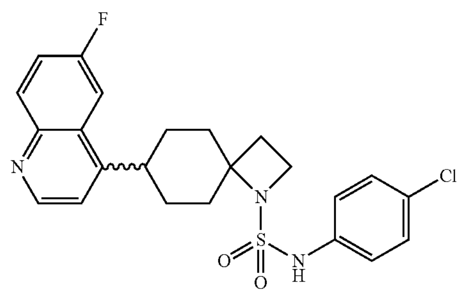 | 461.12 | $^1$H NMR (500 MHz, d$_6$-DMSO) δ 10.14 (s, 1H), 8.88 (s, 1H), 8.06-7.93 (m, 2H), 7.79 (d, J = 8.1 Hz, 2H), 7.58 (d, J = 8.6 Hz, 1H), 7.55-7.43 (m, 3H), 3.54 (dd, J = 13.1, 9.2 Hz, 2H), 3.29-3.12 (m, 1H), 1.94 (dd, J = 9.2, 6.4 Hz, 2H), 1.87-1.60 (m, 8H) |
| 76 | 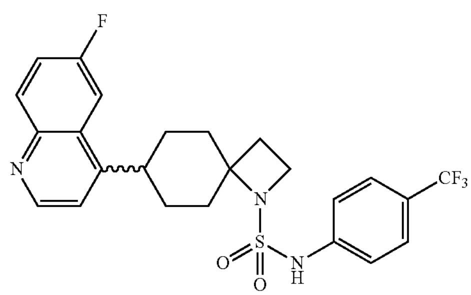 [SMILES: O=S(=O)(Nc1ccc(C(F)(F)F)cc1)N1CCC12CCC(c1ccnc3ccc(F)cc13)CC2] | 494.15 | $^1$H NMR (500 MHz, d$_6$-DMSO) δ 10.12 (s, 1H), 8.74 (s, 1H), 8.03-7.92 (m, 2H), 7.79 (d, J = 8.2 Hz, 2H), 7.58 (d, J = 8.3 Hz, 1H), 7.53-7.3 (m, 3H), 3.54 (dd, J = 13.4, 9.2 Hz, 2H), 3.33-3.14 (m, 1H), 2.01(dd, J = 9.1, 6.2 Hz, 2H), 1.89-1.65 (m, 8H) |
| 78 | 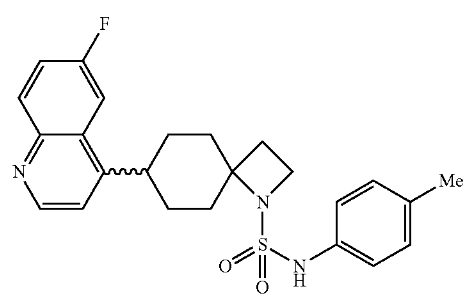 [SMILES: Cc1ccc(NS(=O)(=O)N2CCC23CCC(c2ccnc4ccc(F)cc24)CC3)cc1] | 440.18 | $^1$H NMR (500 MHz, d$_6$-DMSO) δ 10.13 (s, 1H), 8.79 (s, 1H), 8.02-7.96 (m, 2H), 7.75 (d, J = 8.3 Hz, 2H), 7.54 (d, J = 8.3 Hz, 1H), 7.49-7.37 (m, 3H), 3.55 (dd, J = 13.3, 9.0 Hz, 2H), 3.27-3.14 (m, 1H), 2.21 (s, 3H), 1.98(dd, J = 9.2, 6.0 Hz, 2H), 1.88-1.63 (m, 8H) |

Example 80

6-(6-fluoro-7-methylquinolin-4-yl)-N-(4-fluorophenyl)spiro[2.5]octane-1-carboxamide

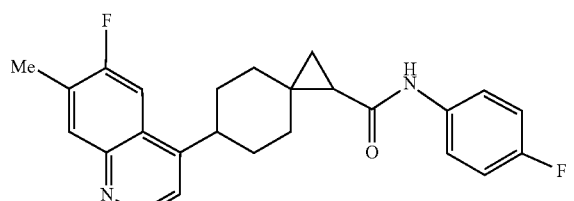

1d

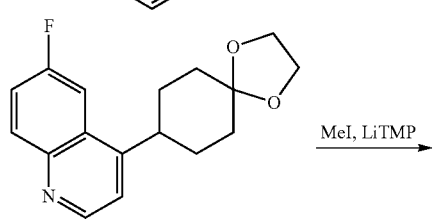

80a

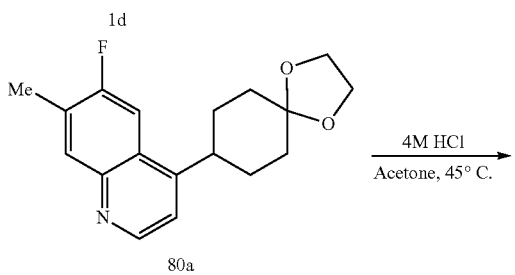

80b

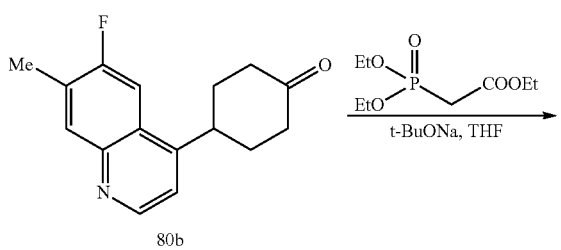

80c

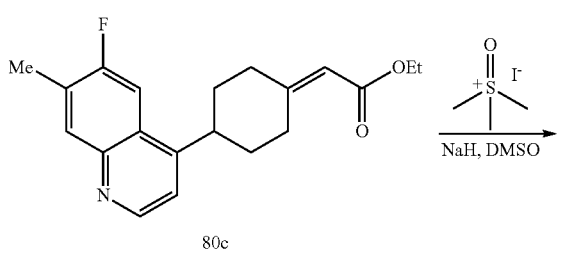

80d

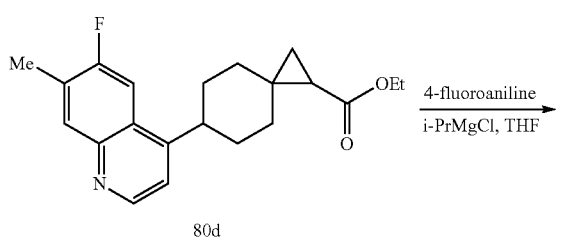

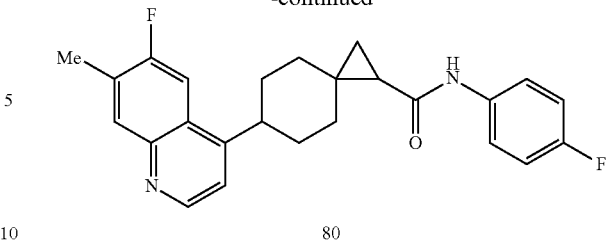

80

Step 1: To a mixture of 2,2,6,6-tetramethylpiperidine (2.12 g, 15.0 mmol) in dry THF (30 mL) at −78° C., n-BuLi (2.5 M in hexane, 6.0 mL, 15.0 mmol) was added dropwise, followed by a solution of compound 1d (2.87 g, 10.0 mmol) in THF (20 mL). After the mixture was stirred at −78° C. for 2 h, a solution of $CH_3I$ (1.3 mL, 20.0 mmol) was added dropwise. The resulting mixture was stirred at −78° C. for 0.5 h and then warmed to r.t. for 2 h. The reaction was quenched by aq. $NH_4Cl$ solution. The mixture was extracted with ethyl acetate three times and the combined organic layers were dried over $Na_2SO_4$, filtered and concentrated under reduced pressure. The residue was purified by column chromatography on silica gel to give compound 80a (2.27 g, yield: 75%) as a white solid. MS (ESI): m/z 302.4 $(M+H)^+$. $^1$H NMR (500 MHz, $CDCl_3$) δ 8.76 (d, J=4.5 Hz, 1H), 7.95 (d, J=7.5 Hz, 1H), 7.62 (d, J=11.5 Hz, 1H), 7.28 (d, J=4.5 Hz, 1H), 4.02 (s, 4H), 3.24-3.17 (m, 1H), 2.49 (s, 3H), 2.04-1.80 (m, 8H).

Step 2: To a solution of compound 80a (2.5 g, 8.31 mmol) in acetone (40 mL) was added HCl (4N in water, 10 mL, 40 mmol) and the mixture was stirred at 45° C. for 16 h. The organic volatiles were removed and the remaining aqueous solution was adjusted to pH=9 by 6N NaOH solution. The mixture was extracted with EtOAc three times. The combined organic layers were washed with brine, dried over $Na_2SO_4$, filtered and concentrated under reduced pressure. The residue was purified by column chromatography on silica gel to give compound 80b (1.9 g, yield: 89%) as a pale-yellow solid. MS (ESI): m/z 258.4 $(M+H)^+$. $^1$H NMR (500 MHz, $CDCl_3$) δ 8.80 (d, J=4.5 Hz, 1H), 7.99 (d, J=7.5 Hz, 1H), 7.67 (d, J=11.0 Hz, 1H), 7.24 (d, J=4.5 Hz, 1H), 3.67 (t, J=12.0 Hz, 1H), 2.72-2.59 (m, 4H), 2.52 (s, 3H), 2.36 (d, J=13.0 Hz, 2H), 2.10-1.98 (m, 2H).

Step 3: To a solution of triethyl phosphonoacetate (1.74 g, 7.76 mmol) in dry THF (20 mL) at 0° C., sodium tert-butoxide (745 mg, 7.76 mmol) was added. After 10 min, a solution of compound 80b (1.9 g, 7.39 mmol) in THF (10 mL) was added to the above mixture and the resulting reaction mixture was stirred for 2 h. The reaction was quenched by $H_2O$, extracted with EtOAc (50 mL×3). The combined organic layers were washed with brine (50 mL), dried over $Na_2SO_4$, filtered and concentrated under reduced pressure. The residue was purified by column chromatography on silica gel to give compound 80c (2.1 g, yield: 87%) as a white solid. MS (ESI): m/z 328.4 $(M+H)^+$. $^1$H NMR (500 MHz, $CDCl_3$) δ 8.76 (d, J=4.5 Hz, 1H), 7.94 (d, J=7.5 Hz, 1H), 7.64 (d, J=11.5 Hz, 1H), 7.18 (d, J=4.5 Hz, 1H), 5.74 (s, 1H), 4.18 (q, J=7.0 Hz, 2H), 4.14-4.06 (m, 1H), 3.48-3.39 (m, 1H), 2.53-2.47 (m, 5H), 2.22-2.12 (m, 3H), 1.78-1.66 (m, 2H), 1.30 (t, J=7.0 Hz, 3H).

Step 4: To a suspension of NaH (60% w/w in mineral oil, 697 mg, 17.43 mmol) in DMSO (20 mL) was added trimethylsulfoxonium iodide (3.83 g, 17.43 mmol). After the mixture was stirred at r.t. for 1.5 h, a solution of compound 80c (1.9 g, 5.81 mmol) in DMSO (10 mL) was added to the above mixture and the resulting reaction mixture was stirred at 40° C. for 16 h. The mixture was quenched by H₂O and extracted with EtOAc. The organic layer was concentrated and the residue was purified by column chromatography on silica gel to give compound 80d (1.1 g, yield: 56%) as a white solid. MS (ESI): m/z 342.4 (M+H)⁺. ¹H NMR (500 MHz, CDCl₃) δ 8.77 (d, J=4.5 Hz, 1H), 7.97 (d, J=8.0 Hz, 1H), 7.64 (d, J=11.5 Hz, 1H), 7.25 (d, J=4.5 Hz, 1H), 4.18 (q, J=7.0 Hz, 2H), 3.24 (t, J=12.0 Hz, 1H), 2.50 (s, 3H), 2.15 (t, J=12.0 Hz, 1H), 2.03-1.90 (m, 4H), 1.85-1.76 (m, 1H), 1.59-1.54 (m, 1H), 1.44-1.35 (m, 1H), 1.30 (t, J=7.0 Hz, 3H), 1.27-1.24 (m, 1H), 1.12 (d, J=13.5 Hz, 1H), 1.02-0.97 (m, 1H).

Step 5: To a mixture of 4-fluoroaniline (76 mg, 0.60 mmol) in dry THF (5 mL) at 0° C., isopropylmagnesium chloride solution (2.0 M in THF, 0.3 mL, 0.60 mmol) was added dropwise. After the mixture was stirred at r.t. for 5 min, a solution of compound 80d (50 mg, 0.15 mmol) in dry THF (2 mL) was added dropwise. The resulting mixture was stirred at r.t. for 16 h. The reaction was quenched by aq. NH₄Cl solution. The mixture was extracted with ethyl acetate three times and the combined organic layers were dried over Na₂SO₄, filtered and concentrated under reduced pressure. The residue was purified by Prep-HPLC to give compound 80 (27.27 mg, yield: 45%) as a white solid. MS (ESI): m/z 407.4 (M+H)⁺. ¹H NMR (500 MHz, d₆-DMSO) δ 10.30 (s, 1H), 8.75 (d, J=4.5 Hz, 1H), 7.99-7.92 (m, 2H), 7.65-7.60 (m, 2H), 7.29 (d, J=5.0 Hz, 1H), 7.13 (t, J=9.0 Hz, 2H), 3.44-3.37 (m, 1H), 2.45 (s, 3H), 2.22-2.15 (m, 1H), 1.97-1.86 (m, 4H), 1.79-1.74 (m, 1H), 1.70 (dd, J=7.5, 5.0 Hz, 1H), 1.30 (dd, J=12.0, 4.0 Hz, 1H), 1.15-1.12 (m, 1H), 1.11-1.07 (m, 1H), 0.91 (dd, J=7.5, 4.0 Hz, 1H).

Compound 81, 82, 83, 84, 85, 86 was prepared using the similar procedures as described for compound 80.

| Compound | Structure | LCMS (M + H)+ | NMR |
|---|---|---|---|
| 81 | 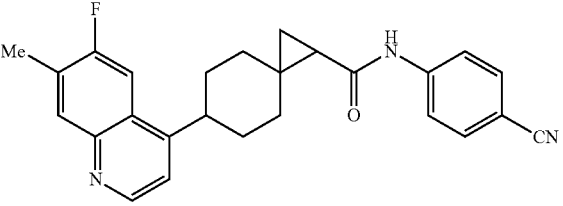 | 414.4 | ¹H NMR (500 MHz, d₆-DMSO) δ 10.72 (s, 1H), 8.82 (s, 1H), 8.06 (d, J = 12.0 Hz, 1H), 7.97 (d, J = 8.0 Hz, 1H), 7.82 (d, J = 8.5 Hz, 2H), 7.76 (d, J = 8.5 Hz, 2H), 7.37 (s, 1H), 3.52-3.49 (m, 1H), 2.47 (s, 3H), 2.24-2.17 (m, 1H), 1.98-1.82 (m, 4H), 1.79-1.74 (m, 2H), 1.30-1.25 (m, 1H), 1.19-1.16 (m, 1H), 1.15-1.10 (m, 1H), 0.99 (dd, J = 7.5, 4.0 Hz, 1H). |
| 82 | 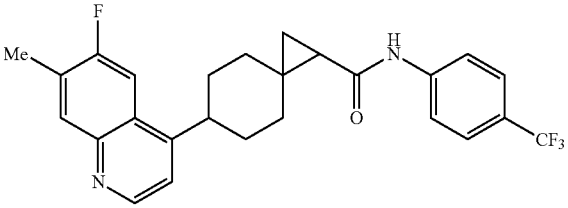 | 457.4 | ¹H NMR (500 MHz, d₆-DMSO) δ 10.42 (s, 1H), 8.76 (s, 1H), 8.01-7.90 (m, 2H), 7.82-7.58 (m, 3H), 7.55 (d, J = 8.5 Hz, 2H), 7.29 (s, 1H), 3.45-3.36 (m, 1H), 2.45 (s, 3H), 2.24-2.15 (m, 1H), 1.99-1.83 (m, 4H), 1.77-1.68 (m, 2H), 1.19-1.09 (m, 2H), 0.98-0.94 (m, 1H). |
| 83 | 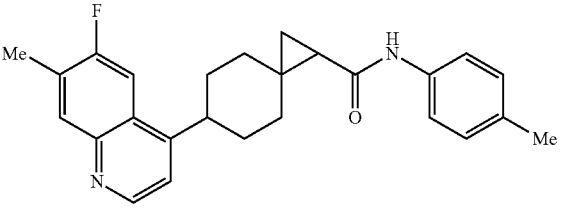 [SMILES: Cc1cc2nccc(C3CCC4(CC3)CC4C(=O)Nc3ccc(C#N)cc3)c2cc1F] | 403.5 | ¹H NMR (500 MHz, d₆-DMSO) δ 10.14 (s, 1H), 8.75 (d, J = 4.5 Hz, 1H), 7.98-7.92 (m, 2H), 7.49 (d, J = 8.0 Hz, 2H), 7.28 (d, J = 4.5 Hz, 1H), 7.09 (d, J = 8.0 Hz, 2H), 3.41-3.39 (m, 1H), 2.44 (s, 3H), 2.23 (s, 3H), 2.04-1.85 (m, 5H), 1.78-1.83 (m, 1H), 1.72-1.67 (m, 1H), 1.14-1.11 (m, 1H), 1.10-1.06 (m, 1H), 0.91-0.83 (m, 2H). |
| 84 | 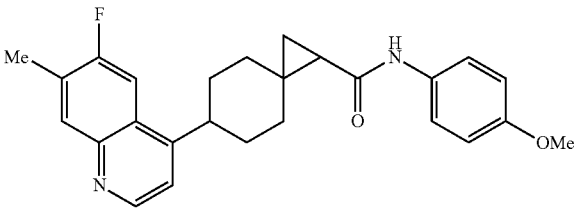 [SMILES: COc1ccc(NC(=O)C2CC23CCC(c2ccnc4cc(C)c(F)cc24)CC3)cc1] | 419.4 | ¹H NMR (500 MHz, d₆-DMSO) δ 10.36 (s, 1H), 8.77 (s, 1H), 7.99-7.90 (m, 2H), 7.81-7.55 (m, 3H), 7.29 (s, 1H), 6.96 (d, J = 8.0 Hz, 2H), 3.82 (s, 3H), 3.46-3.36 (m, 1H), 2.45 (s, 3H), 2.24-2.15 (m, 1H), 1.96-1.83 (m, 4H), 1.79-1.67 (m, 2H), 1.18-1.09 (m, 2H), 0.96-0.94 (m, 1H). |

| Compound | Structure | LCMS (M + H)+ | NMR |
|---|---|---|---|
| 85 | 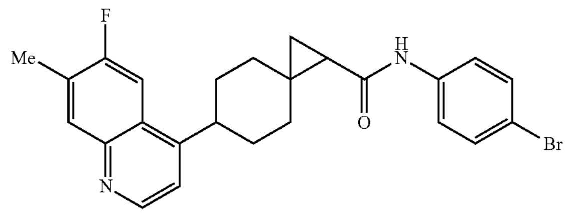 | 467.4 | ¹H NMR (500 MHz, $d_6$-DMSO) δ 10.36 (s, 1H), 8.77 (s, 1H), 7.99-7.92 (m, 2H), 7.82-7.57 (m, 3H), 7.35 (d, J = 8.0 Hz, 2H), 7.29 (s, 1H), 3.45-3.37 (m, 1H), 2.42 (s, 3H), 2.24-2.12 (m, 1H), 1.96-1.83 (m, 4H), 1.79-1.70 (m, 2H), 1.18-1.07 (m, 2H), 0.96-0.93 (m, 1H). |
| 86 | 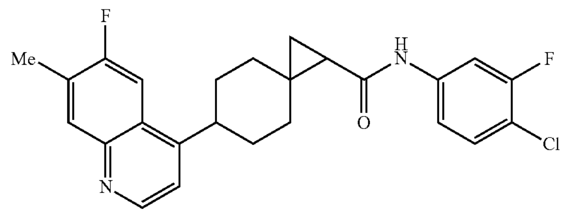 | 441.4 | ¹H NMR (500 MHz, $d_6$-DMSO) δ 10.38 (s, 1H), 8.76 (s, 1H), 7.98-7.91 (m, 2H), 7.80-7.76 (m, 1H), 7.52-7.49 (m, 2H), 7.71 (s, 1H), 7.27 (s, 1H), 3.43-3.36 (m, 1H), 2.46 (s, 3H), 2.25-2.15 (m, 1H), 1.97-1.86 (m, 4H), 1.79-1.70 (m, 2H), 1.16-1.05 (m, 2H), 0.98-0.95 (m, 1H). |
Example 87
N-(4-chlorophenyl)-8-(6-fluoroquinolin-4-yl)-2-methyl-2-azaspiro[4.5]decane-4-carboxamide
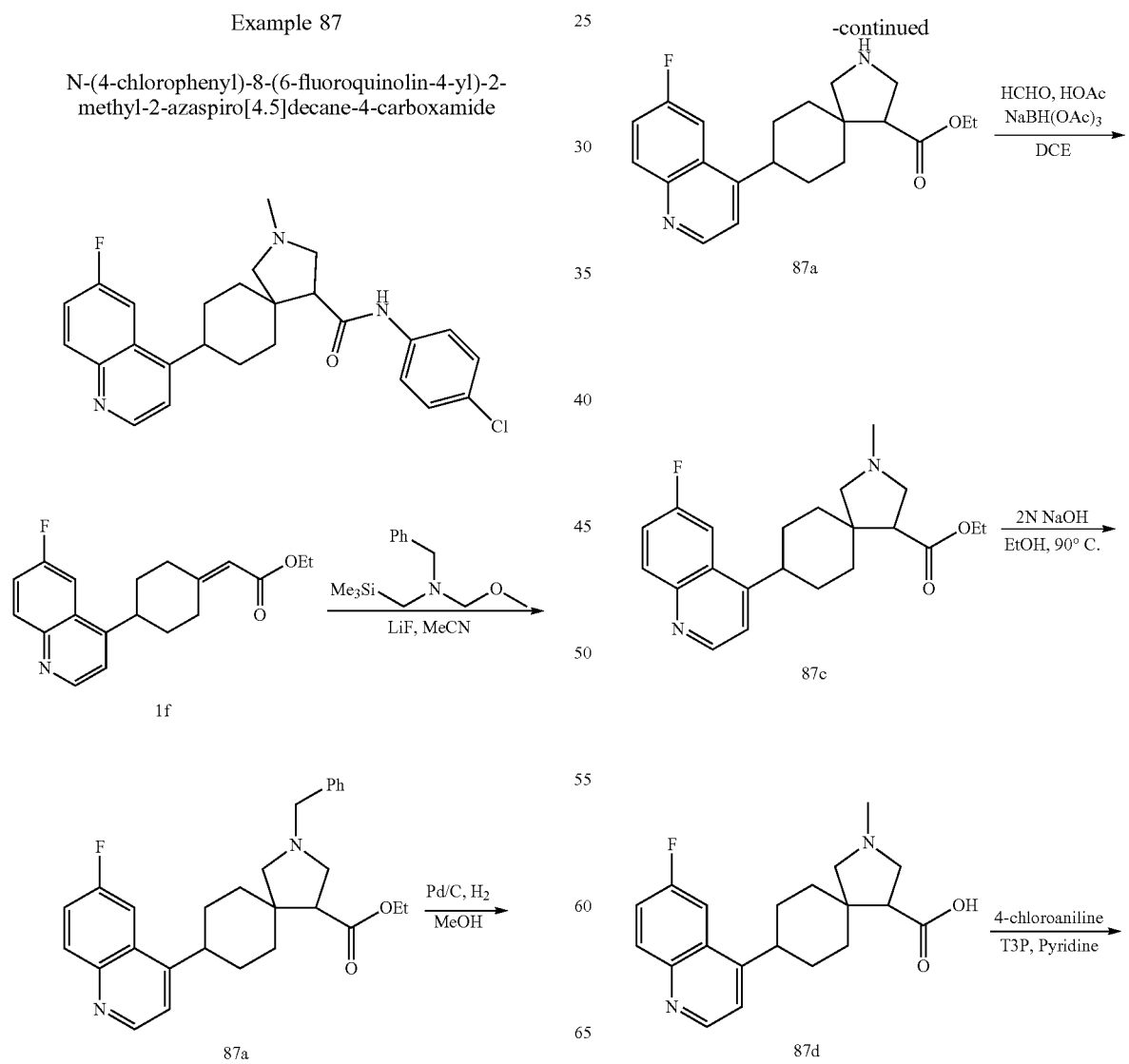

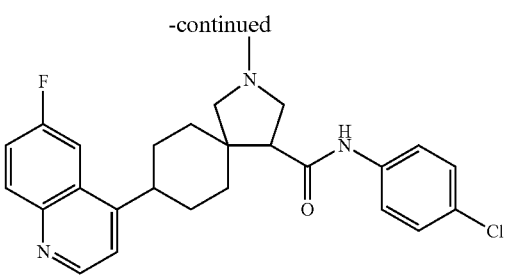

87

Step 1: To a solution of compound 1f (400 mg, 1.28 mmol) in MeCN (15 mL) were subsequently added N-(methoxymethyl)-N-(trimethylsilylmethyl) benzylamine (3.03 g, 12.8 mmol) and LiF (998 mg, 38.4 mmol) and the mixture was stirred at 60° C. for 24 h. The mixture was cooled to r.t. and diluted with H₂O (50 mL). The resulting mixture was extracted with EtOAc three times. The combined organic layers were dried over Na₂SO₄, filtered and concentrated under reduced pressure. The residue was purified by Prep-TLC to give compound 87a (376 mg, yield: 66%) as colorless oil. MS (ESI): m/z 447.4 (M+H)⁺.

Step 2: To a solution of compound 87a (400 mg, 0.90 mmol) in MeOH (20 mL) was added 10% w/w palladium on carbon (40 mg). The mixture was stirred at r.t. under hydrogen atmosphere for 16 h. The reaction was filtered over a pad of celite. The filtrate was concentrated to give compound 87b (300 mg, yield: 94%) as an oily liquid, which was used to the next step directly. MS (ESI): m/z 357.3 (M+H)⁺.

Step 3: To a solution of compound 87b (300 mg, 0.84 mmol) in DCM (10 mL) were subsequently added formaldehyde (50 mg, 0.84 mmol), sodium triacetoxyborohydride (178 mg, 0.84 mmol) and two drops AcOH. The mixture was stirred at r.t. for 16 h. The mixture was diluted with H₂O (20 mL) and extracted with DCM three times. The combined organic layers were dried over Na₂SO₄, filtered and concentrated under reduced pressure. The residue was purified by Prep-TLC to give compound 87c (136 mg, yield: 44%) as pale-yellow oil. MS (ESI): m/z 371.3 (M+H)⁺.

Step 4: To a solution of compound 87c (136 mg, 0.37 mmol) in ethanol (10 mL) was added NaOH (2N in water, 4.0 mL, 8.0 mmol) and the mixture was stirred at 50° C. for 24 h. The mixture was cooled to r.t. and adjusted to pH=1 by 4N HCl solution. The mixture was extracted with EtOAc three times. The combined organic layers were dried over Na₂SO₄, filtered and concentrated under reduced pressure. The residue was purified by Prep-TLC to give compound 87d (98 mg, yield: 78%) as a white solid. MS (ESI): m/z 343.3 (M+H)⁺.

Step 5: To a solution of compound 87d (40 mg, 0.12 mmol) in ethyl acetate (5 mL) were subsequently added pyridine (28 mg, 0.36 mmol) and 2,4,6-Tripropyl-1,3,5,2,4,6-Trioxatriphosphorinane-2,4,6-Trioxide (50% wt in EtOAc, 114 mg, 0.18 mmol) and the mixture was stirred at r.t. for 10 min. 4-aminobenzotrifluoride (23 mg, 0.18 mmol) was added to the above mixture and the resulting reaction mixture was stirred at r.t. for 16 h. The mixture was quenched by NaOH (2N in water, 2 mL) and diluted with H₂O (20 mL). The resulting mixture was extracted with EtOAc three times. The combined organic layers were dried over Na₂SO₄, filtered and concentrated under reduced pressure. The residue was purified by Prep-HPLC to give cis- and trans- mixture 87 (12.68 mg, yield: 23%) as a white solid. MS (ESI): m/z 452.4 (M+H)⁺. ¹H NMR (500 MHz, d₆-DMSO) δ 10.50 (s, 1H), 8.72 (d, J=4.5 Hz, 1H), 8.09-8.03 (m, 1H), 7.98 (dd, J=11.0, 2.5 Hz, 1H), 7.72-7.63 (m, 3H), 7.40-7.35 (m, 2H), 7.31-7.27 (m, 1H), 3.35-3.30 (m, 2H), 3.24-3.18 (m, 1H), 2.99-2.92 (m, 1H), 2.64-2.58 (m, 1H), 2.38-2.29 (m, 4H), 2.06-1.96 (m, 2H), 1.93-1.51 (m, 5H), 1.50-1.41 (m, 1H).

Compound 88, 89, 90, 91 was prepared using the similar procedures as described for compound 87.

Example 92

(1S)-N-(4-chlorophenyl)-6-(6-fluoro-7-methylquinolin-4-yl)spiro[2.5]octane-1-carboxamide

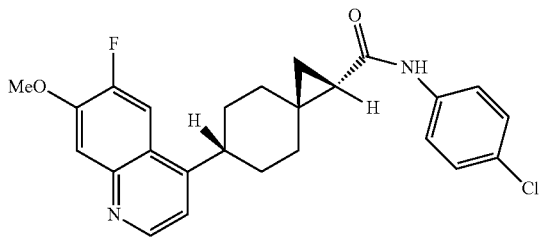 [SMILES: COc1cc2nccc([C@H]3CC[C@@]4(CC3)C[C@@H]4C(=O)Nc3ccc(Cl)cc3)c2cc1F]

Example 93

(1R)-N-(4-chlorophenyl)-6-(6-fluoro-7-methylquinolin-4-yl)spiro[2.5]octane-1-carboxamide

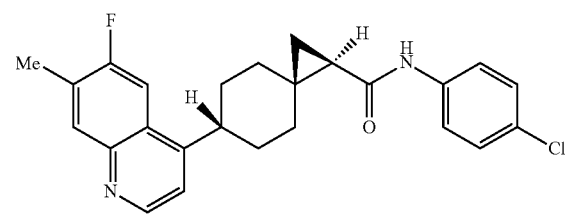 [SMILES: Cc1cc2nccc([C@H]3CC[C@@]4(CC3)C[C@H]4C(=O)Nc3ccc(Cl)cc3)c2cc1F]

Compound 92 and Compound 93 were obtained by chiral column separation of compound 9. Absolute stereochemistry arbitrarily assigned.

Compound 92: MS (ESI): m/z 423.4 (M+H)⁺. ¹H NMR (500 MHz, d₆-DMSO) δ 10.39 (s, 1H), 8.75 (d, J=4.5 Hz, 1H), 7.97 (d, J=12.0 Hz, 1H), 7.94 (d, J=8.0 Hz, 1H), 7.65 (d, J=9.0 Hz, 2H), 7.34 (d, J=9.0 Hz, 2H), 7.28 (d, J=4.5 Hz, 1H), 3.44-3.38 (m, 1H), 2.44 (s, 3H), 2.24-2.14 (m, 1H), 1.97-1.82 (m, 4H), 1.80-1.74 (m, 1H), 1.73-1.69 (m, 1H), 1.32-1.24 (m, 1H), 1.17-1.12 (m, 1H), 1.10 (d, J=13.0 Hz, 1H), 0.93 (dd, J=7.5, 4.0 Hz, 1H).

Compound 93: MS (ESI): m/z 423.4 (M+H)⁺. ¹H NMR (500 MHz, d₆-DMSO) δ 10.39 (s, 1H), 8.75 (d, J=4.5 Hz, 1H), 7.97 (d, J=12.0 Hz, 1H), 7.94 (d, J=8.0 Hz, 1H), 7.65 (d, J=9.0 Hz, 2H), 7.34 (d, J=9.0 Hz, 2H), 7.28 (d, J=4.5 Hz, 1H), 3.45-3.38 (m, 1H), 2.45 (s, 3H), 2.24-2.14 (m, 1H), 1.97-1.82 (m, 4H), 1.80-1.74 (m, 1H), 1.73-1.69 (m, 1H), 1.32-1.24 (m, 1H), 1.16-1.13 (m, 1H), 1.10 (d, J=13.0 Hz, 1H), 0.93 (dd, J=7.5, 4.0 Hz, 1H).

Example 94

6-(6-fluoro-7-methylquinolin-4-yl)-N-(4-(2-methoxyethoxy)phenyl)spiro[2.5]octane-1-carboxamide

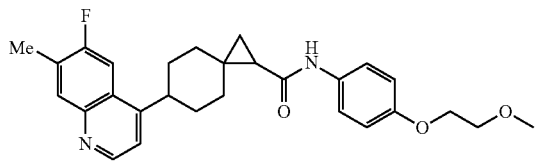

80d

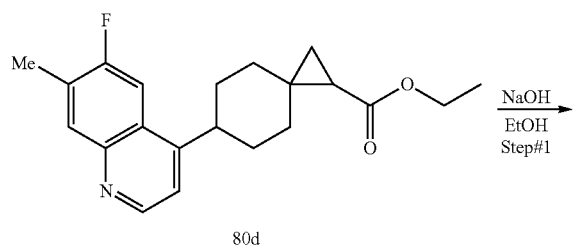

94a

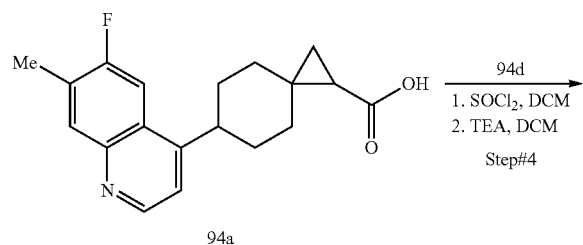

94

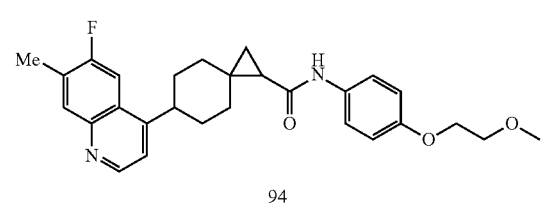

94b

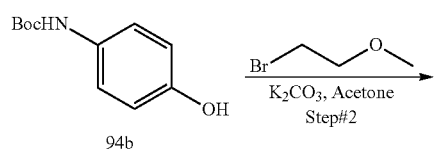

94c

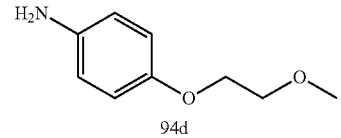

94d

Step 1: To a solution of compound 80d (200 mg, 0.59 mmol) in ethanol (10 mL) was added NaOH (2N in water, 4.0 mL, 8.0 mmol) and the mixture was stirred at 50° C. for 2 h. The mixture was cooled to r.t. and adjusted to pH=1 by 4N HCl solution. The mixture was extracted with EtOAc three times. The combined organic layers were dried over $Na_2SO_4$, filtered and concentrated under reduced pressure. The residue was purified by Prep-TLC to give compound 94a (150 mg, yield: 81%) as a white solid. MS (ESI): m/z 314.4 (M+H)$^+$.

Step 2: To a solution of compound 94b (1.0 g, 4.78 mmol) and 1-bromo-2-methoxyethane (1.33 g, 9.56 mmol) in acetone (20 mL) was added $K_2CO_3$ (1.98 g, 14.34 mmol) and the mixture was stirred at 60° C. for 2 h. The mixture was filtered and concentrated under reduced pressure. The residue was purified by column chromatography on silica gel to give compound 94c (1.2 g, yield: 94%) as a white solid. $^1$H NMR (500 MHz, CDCl$_3$) δ 7.25 (d, J=9.0 Hz, 2H), 6.86 (d, J=9.0 Hz, 2H), 6.36 (s, 1H), 4.08 (t, J=4.5 Hz, 2H), 3.73 (t, J=4.5 Hz, 2H), 3.44 (s, 3H), 1.50 (s, 9H).

Step 3: To a solution of compound 94c (1.2 g, 4.49 mmol) in DCM (3 mL) was added HCl (4N in dioxnae, 6 mL, 24 mmol) at 0° C. and the mixture was stirred at r.t. for 2 h. Precipitation was formed and the mixture was filtered. The filter cake was dried under vacuum to give compound 94d (900 mg, yield: 98%) as a white solid, which was used to the next step directly. $^1$H NMR (500 MHz, d$_6$-DMSO) δ 10.26 (br, 3H), 7.32 (d, J=9.0 Hz, 2H), 7.04 (d, J=9.0 Hz, 2H), 4.10 (t, J=4.0 Hz, 2H), 3.65 (t, J=4.0 Hz, 2H), 3.30 (s, 3H).

Step 4: To a solution of compound 94a (53 mg, 0.17 mmol) in dry DCM (2 mL) was added thionyl chloride (5 mL) and the mixture was stirred at refluxing temperature for 2 h. The reaction mixture was concentrated under reduced pressure to give a pale-yellow solid, which was dissolved in dry DCM (3 mL). Compound 94d (30 mg, 0.17 mmol) in dry DCM (2 mL) was added to the above solution at 0° C., followed by Et$_3$N (52 mg, 0.51 mmol). The resulting mixture was stirred at 0° C. for 10 min and then warmed to r.t. for 2 h. The reaction was quenched by $H_2O$. The mixture was extracted with DCM three times and the combined organic layers were dried over $Na_2SO_4$, filtered and concentrated under reduced pressure. The residue was purified by Prep-HPLC to give compound 94 (43.60 mg, yield: 56%) as a white solid. MS (ESI): m/z 463.7 (M+H)$^+$. $^1$H NMR (500 MHz, d$_6$-DMSO) δ 10.07 (s, 1H), 8.75 (d, J=4.5 Hz, 1H), 7.98-7.92 (m, 2H), 7.49 (d, J=9.0 Hz, 2H), 7.29 (d, J=4.5 Hz, 1H), 6.87 (d, J=9.0 Hz, 2H), 4.03 (t, J=4.5 Hz, 2H), 3.63 (t, J=4.5 Hz, 2H), 3.44-3.37 (m, 1H), 3.29 (s, 3H), 2.45 (s, 3H), 2.22-2.14 (m, 1H), 1.99-1.85 (m, 4H), 1.76 (d, J=12.0 Hz, 1H), 1.70-1.65 (m, 1H), 1.37-1.28 (m, 1H), 1.14-1.06 (m, 2H), 0.88 (dd, J=7.5, 4.0 Hz, 1H).

Example 95

N-(6-chloropyridin-3-yl)-6-(6-fluoro-7-methylquinolin-4-yl)spiro[2.5]octane-1-carboxamide

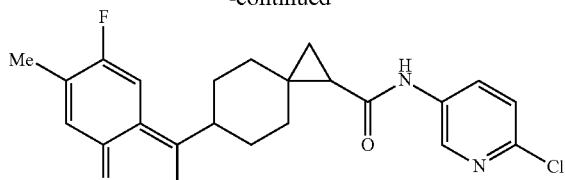

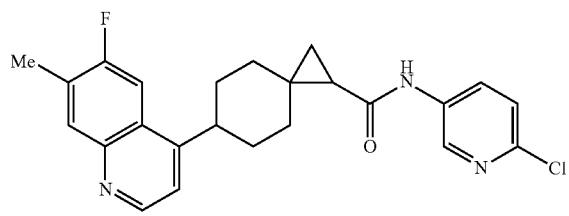

To a solution of compound 94a (53 mg, 0.17 mmol) in dry DCM (5 mL) was added thionyl chloride (2.5 mL) and the mixture was stirred at refluxing temperature for 2 h. The reaction mixture was concentrated under reduced pressure to give a pale-yellow solid, which was dissolved in dry THF (5 mL). 5-amino-2-chloropyridine (44 mg, 0.34 mmol) was added to the above solution, followed by the addition of $Et_3N$ (52 mg, 0.51 mmol) at 0° C. The resulting mixture was stirred at 0° C. for 30 min and then warmed to r.t. while stirring for another 2 h. The reaction was quenched by $H_2O$. The mixture was extracted with EtOAc three times and the combined organic layers were dried over $Na_2SO_4$, filtered and concentrated under reduced pressure. The residue was purified by Prep-HPLC to give compound 95 (24.07 mg, yield: 33%) as a white solid. MS (ESI): m/z 424.6 (M+H)$^+$. $^1$H NMR (500 MHz, d$_6$-DMSO) δ 10.61 (s, 1H), 8.75 (d, J=4.5 Hz, 1H), 8.63 (d, J=3.0 Hz, 1H), 8.11 (dd, J=8.5, 2.5 Hz, 1H), 7.99-7.91 (m, 2H), 7.45 (d, J=8.5 Hz, 1H), 7.30 (d, J=4.5 Hz, 1H), 3.45-3.37 (m, 1H), 2.44 (s, 3H), 2.24-2.16 (m, 1H), 1.97-1.82 (m, 4H), 1.80-1.71 (m, 2H), 1.34-1.25 (m, 1H), 1.19-1.09 (m, 2H), 0.97 (dd, J=7.5, 4.0 Hz, 1H).

Compound 96, 97 was prepared using the similar procedures as described for compound 95.

| Compound | Structure | LCMS (M + H)+ | NMR |
|---|---|---|---|
| 96 | 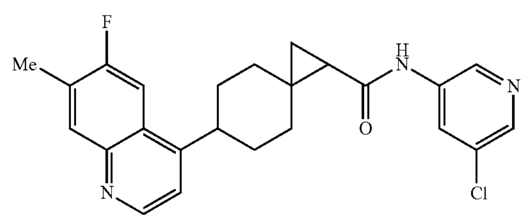 [SMILES: Cc1cc2nccc(C3CCC4(CC3)CC4C(=O)Nc3cncc(Cl)c3)c2cc1F] | 424.7 | $^1$H NMR (500 MHz, d$_6$-DMSO) δ 10.70 (s, 1H), 8.75 (d, J = 4.5 Hz, 1H), 8.66 (s, 1H), 8.32-8.27 (m, 2H), 7.99-7.92 (m, 2H), 7.31 (d, J = 4.5 Hz, 1H), 3.45-3.38 (m, 1H), 2.45 (s, 3H), 2.24-2.17 (m, 1H), 1.97-1.83 (m, 4H), 1.80-1.72 (m, 2H), 1.34-1.24 (m, 1H), 1.18 (t, J = 4.5 Hz, 1H), 1.13 (d, J = 14.0 Hz, 1H), 1.00 (dd, J = 7.5, 4.0 Hz, 1H). |
| 97 | 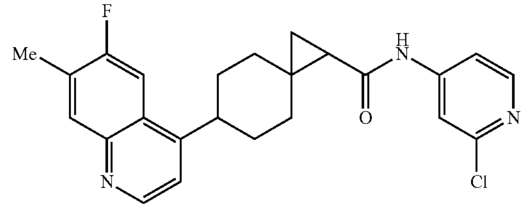 [SMILES: Cc1cc2nccc(C3CCC4(CC3)CC4C(=O)Nc3ccnc(Cl)c3)c2cc1F] | 424.6 | $^1$H NMR (500 MHz, d$_6$-DMSO) δ 10.88 (s, 1H), 8.75 (d, J = 4.5 Hz, 1H), 8.24 (d, J = 6.0 Hz, 1H), 7.98-7.92 (m, 2H), 7.81 (s, 1H), 7.49 (dd, J = 5.5, 1.5 Hz, 1H), 7.29 (d, J = 4.5 Hz, 1H), 3.45-3.38 (m, 1H), 2.44 (s, 3H), 2.24-2.17 (m, 1H), 1.98-1.87 (m, 3H), 1.86-1.73 (m, 3H), 1.30-1.17 (m, 2H), 1.13 (d, J = 12.5 Hz, 1H), 1.02 (dd, J = 7.5, 4.0 Hz, 1H). |

Example 98

(S)-6-(6-fluoro-7-methylquinolin-4-yl)-N-(4-(2-methoxyethoxy)phenyl)spiro[2.5]octane-1-carboxamide

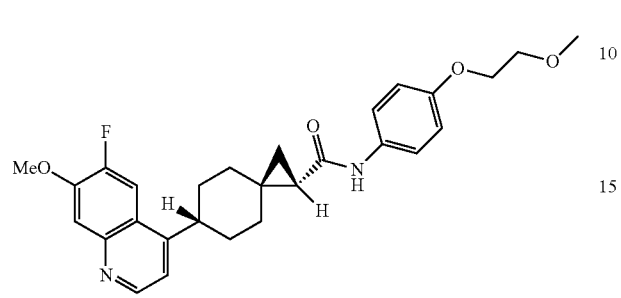

Example 99

(R)-6-(6-fluoro-7-methylquinolin-4-yl)-N-(4-(2-methoxyethoxy)phenyl)spiro[2.5]octane-1-carboxamide

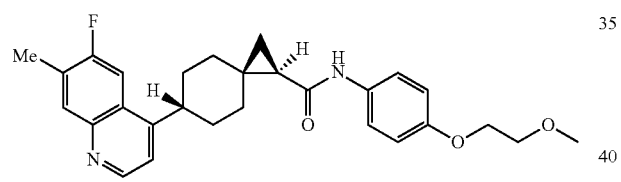

Compound 98 and Compound 99 were obtained by chiral column separation of compound 94. Absolute stereochemistry arbitrarily assigned.

Compound 98: MS (ESI): m/z 463.7 (M+H)+. 1H NMR (500 MHz, d6-DMSO) δ 10.07 (s, 1H), 8.75 (d, J=4.5 Hz, 1H), 7.98-7.92 (m, 2H), 7.49 (d, J=9.0 Hz, 2H), 7.29 (d, J=4.5 Hz, 1H), 6.87 (d, J=9.0 Hz, 2H), 4.03 (t, J=4.5 Hz, 2H), 3.63 (t, J=4.5 Hz, 2H), 3.44-3.37 (m, 1H), 3.29 (s, 3H), 2.45 (s, 3H), 2.22-2.14 (m, 1H), 1.99-1.85 (m, 4H), 1.76 (d, J=12.0 Hz, 1H), 1.70-1.65 (m, 1H), 1.37-1.28 (m, 1H), 1.14-1.06 (m, 2H), 0.88 (dd, J=7.5, 4.0 Hz, 1H).

Compound 99: MS (ESI): m/z 463.7 (M+H)+. 1H NMR (500 MHz, d6-DMSO) δ 10.07 (s, 1H), 8.75 (d, J=4.5 Hz, 1H), 7.98-7.92 (m, 2H), 7.49 (d, J=9.0 Hz, 2H), 7.29 (d, J=4.5 Hz, 1H), 6.87 (d, J=9.0 Hz, 2H), 4.03 (t, J=4.5 Hz, 2H), 3.63 (t, J=4.5 Hz, 2H), 3.44-3.37 (m, 1H), 3.29 (s, 3H), 2.45 (s, 3H), 2.22-2.14 (m, 1H), 1.99-1.85 (m, 4H), 1.76 (d, J=12.0 Hz, 1H), 1.70-1.65 (m, 1H), 1.37-1.28 (m, 1H), 1.14-1.06 (m, 2H), 0.88 (dd, J=7.5, 4.0 Hz, 1H).

Example 100

N-(4-chlorophenyl)-6-(6,7-difluoroquinolin-4-yl)spiro[2.5]octane-1-carboxamide

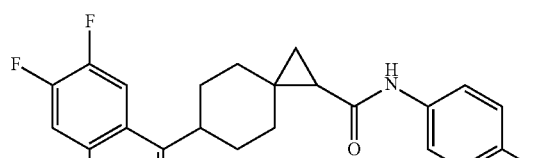

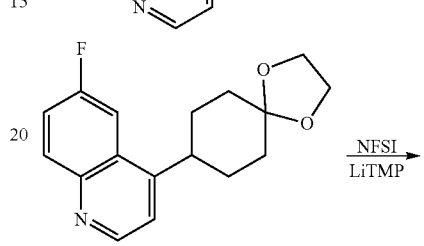

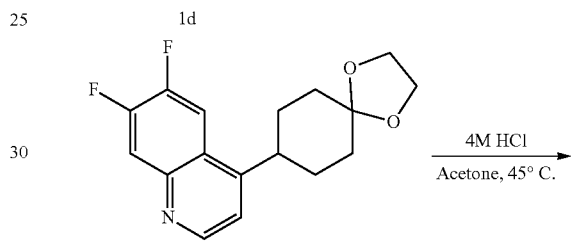

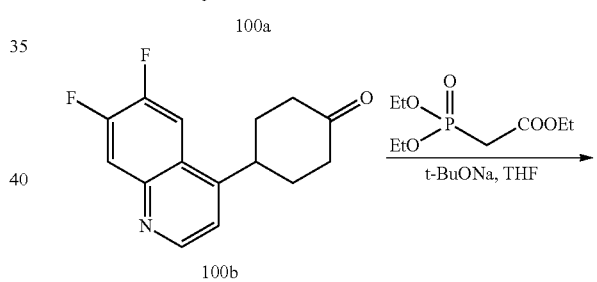

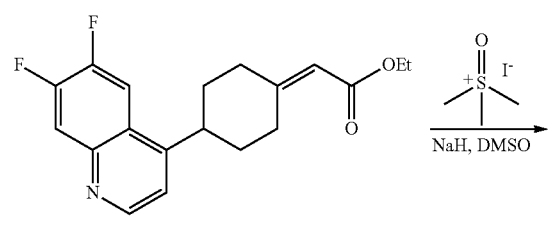

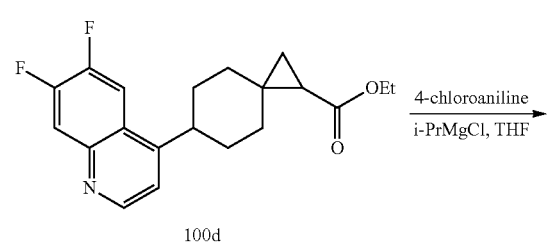

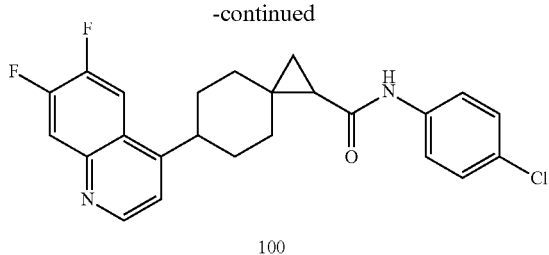

100

Step 1: To a mixture of 2,2,6,6-tetramethylpiperidine (368 mg, 2.61 mmol) in dry THF (20 mL) at −78° C., n-BuLi (2.5 M in hexane, 1.1 mL, 2.61 mmol) was added dropwise, followed by a solution of compound 1d (500 mg, 1.74 mmol) in THF (10 mL). After the mixture was stirred at −78° C. for 2 h, a solution of N-fluorobenzenesulfonimide (1.1 g, 3.48 mmol) in dry THF (10 mL) was added dropwise. The resulting mixture was stirred at −78° C. for 0.5 h and then warmed to r.t. while stirring for another 2 h. The reaction was quenched by aq. NH$_4$Cl solution. The mixture was extracted with ethyl acetate three times and the combined organic layers were dried over Na$_2$SO$_4$, filtered and concentrated under reduced pressure. The residue was purified by column chromatography on silica gel to give compound 101a (410 mg, yield: 77%) as a white solid. MS (ESI): m/z 306.5 (M+H)$^+$.

Step 2: To a solution of compound 100a (410 mg, 1.34 mmol) in acetone (10 mL) was added HCl (4N in water, 3 mL, 12 mmol) and the mixture was stirred at 45° C. for 4 h. The organic volatiles were removed and the remaining aqueous solution was adjusted to pH=9 by 6N NaOH solution. The mixture was extracted with EtOAc three times. The combined organic layers were washed with brine, dried over Na$_2$SO$_4$, filtered and concentrated under reduced pressure. The residue was purified by column chromatography on silica gel to give compound 100b (190 mg, yield: 54%) as a white solid. MS (ESI): m/z 262.5 (M+H)$^+$.

Step 3: To a solution of triethyl phosphonoacetate (172 mg, 0.77 mmol) in dry THF (10 mL) at 0° C., sodium tert-butoxide (74 mg, 0.77 mmol) was added. After 10 min, a solution of compound 100b (190 mg, 0.73 mmol) in THF (5 mL) was added to the above mixture and the resulting reaction mixture was stirred for 2 h. The reaction was quenched by H$_2$O, extracted with EtOAc (20 mL×3). The combined organic layers were washed with brine (20 mL), dried over Na$_2$SO$_4$, filtered and concentrated under reduced pressure. The residue was purified by column chromatography on silica gel to give compound 100c (180 mg, yield: 74%) as a white solid. MS (ESI): m/z 332.5 (M+H)$^+$.

Step 4: To a suspension of NaH (60% w/w in mineral oil, 65 mg, 1.62 mmol) in DMSO (10 mL) was added trimethylsulfoxonium iodide (356 mg, 1.62 mmol). After the mixture was stirred at r.t. for 1.5 h, a solution of compound 100c (180 mg, 0.54 mmol) in DMSO (5 mL) was added to the above mixture and the resulting reaction mixture was stirred at 40° C. for 16 h. The mixture was quenched by H$_2$O and extracted with EtOAc. The organic layer was concentrated and the residue was purified by column chromatography on silica gel to give compound 100d (80 mg, yield: 43%) as colorless oil. MS (ESI): m/z 346.5 (M+H)$^+$.

Step 5: To a mixture of 4-chloroaniline (117 mg, 0.92 mmol) in dry THF (5 mL) at 0° C., isopropylmagnesium chloride solution (2.0 M in THF, 0.5 mL, 0.92 mmol) was added dropwise. After the mixture was stirred at r.t. for 5 min, a solution of compound 100d (80 mg, 0.23 mmol) in dry THF (2 mL) was added dropwise. The resulting mixture was stirred at r.t. for 16 h. The reaction was quenched by aq. NH$_4$Cl solution. The mixture was extracted with ethyl acetate three times and the combined organic layers were dried over Na$_2$SO$_4$, filtered and concentrated under reduced pressure. The residue was purified by Prep-HPLC to give compound 100 (36.20 mg, yield: 37%) as a white solid. MS (ESI): m/z 427.4 (M+H)$^+$. $^1$H NMR (500 MHz, d$_6$-DMSO) δ 10.38 (s, 1H), 8.83 (d, J=4.5 Hz, 1H), 8.33 (dd, J=12.5, 9.0 Hz, 1H), 8.00 (dd, J=11.5, 8.5 Hz, 1H), 7.65 (d, J=8.5 Hz, 2H), 7.39-7.30 (m, 3H), 3.49-3.41 (m, 1H), 2.23-2.15 (m, 1H), 1.98-1.83 (m, 4H), 1.76 (d, J=13.0 Hz, 1H), 1.73-1.69 (m, 1H), 1.33-1.24 (m, 1H), 1.16-1.13 (m, 1H), 1.10 (d, J=13.0 Hz, 1H), 0.93 (dd, J=7.5, 4.0 Hz, 1H).

Example 101

N-(4-chlorophenyl)-1-cyano-6-(6-fluoroquinolin-4-yl)spiro[2.5]octane-1-carboxamide

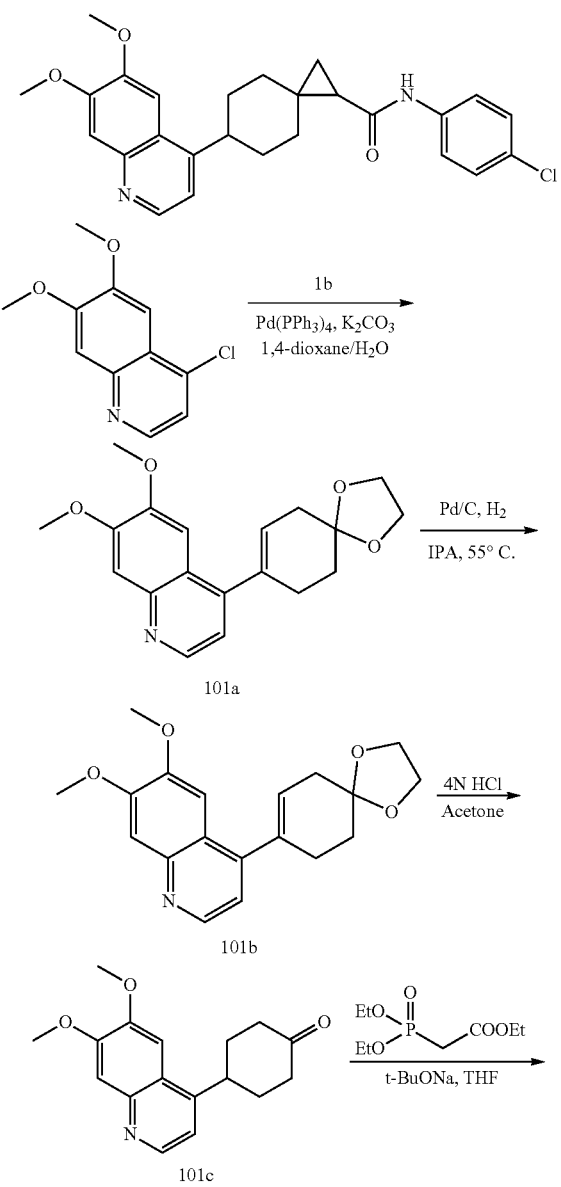

117

-continued

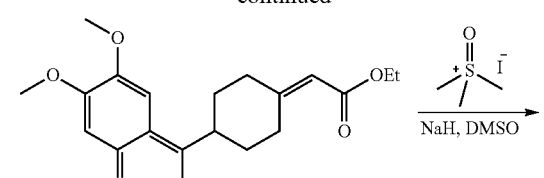

101d

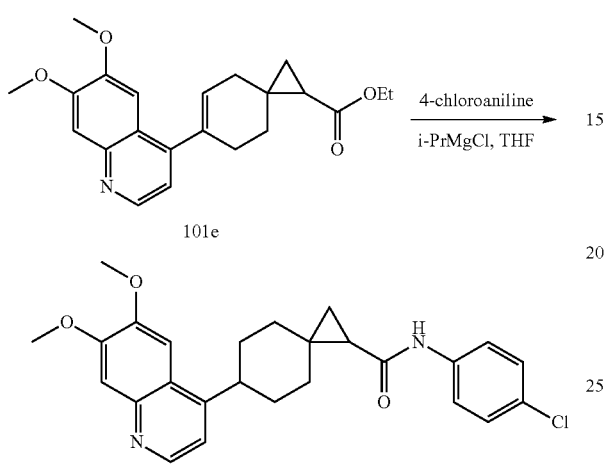

101e

Compound 101 was prepared using the similar procedures as described for compound 1 using 4-chloro-6,7-dimethoxyquioline to replace 4-chloro-6-fluoroquinoline. MS (ESI): m/z 451.4 (M+H)+. 1H NMR (500 MHz, d6-DMSO) δ 10.41 (s, 1H), 8.58 (s, 1H), 7.65 (d, J=8.0 Hz, 2H), 7.40 (s, 1H), 7.37-7.33 (m, 3H), 7.14 (s, 1H), 3.94 (s, 3H), 3.91 (s, 3H), 3.47-3.42 (m, 1H), 2.24-2.15 (m, 1H), 1.96-1.86 (m, 4H), 1.82-1.76 (m, 1H), 1.75-1.70 (m, 1H), 1.34-1.24 (m, 1H), 1.16-1.09 (m, 2H), 0.95-0.90 (m, 1H).

Example 102

N-(4-chlorophenyl)-6-(7-cyano-6-fluoroquinolin-4-yl)spiro[2.5]octane-1-carboxamide

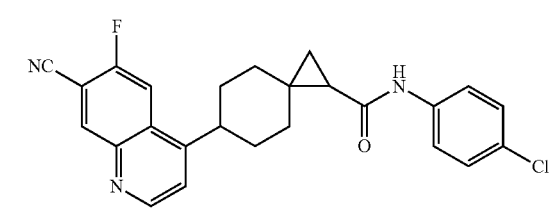 [SMILES: N#Cc1cc2nccc(C3CCC4(CC3)CC4C(=O)Nc3ccc(Cl)cc3)c2cc1F]

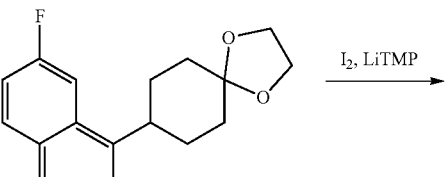

1d

118

-continued

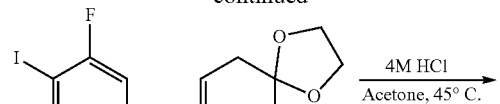

102a

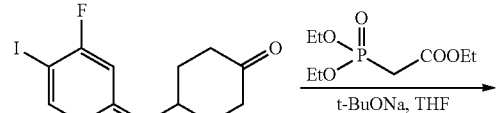

102b

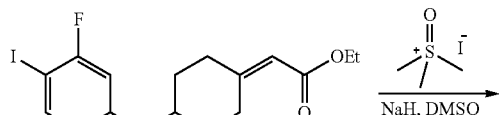

102c

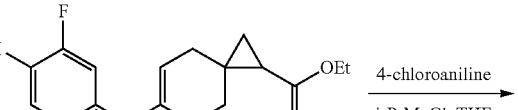

102d

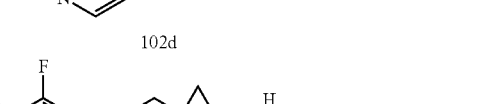

102e

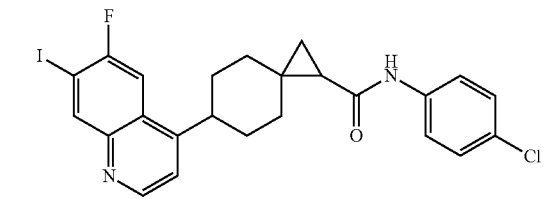

102

Step 1: To a mixture of 2,2,6,6-tetramethylpiperidine (983 mg, 6.97 mmol) in dry THF (50 mL) at −78° C. under N2, n-BuLi (2.5 M in hexane, 2.8 mL, 6.97 mmol) was added dropwise, followed by a solution of compound 1d (2.0 g, 6.97 mmol) in THF (20 mL). After the mixture was stirred at −78° C. for 2 h, a solution of I2 (3.54 g, 13.94 mmol) in THF (10 mL) was added dropwise. The resulting mixture was stirred at −78° C. for 0.5 h and then warmed to r.t. while stirring for another 2 h. The reaction was quenched by aq. NH4Cl solution. The mixture was extracted with ethyl acetate three times and the combined organic layers were dried over Na2SO4, filtered and concentrated under reduced pressure. The residue was purified by column chromatography on silica gel to give compound 102a (2.0 g, yield: 69%) as a white solid. MS (ESI): m/z 414.4 (M+H)+.

Step 2: To a solution of compound 102a (1.0 g, 2.42 mmol) in acetone (30 mL) was added HCl (4N in water, 9 mL, 36 mmol) and the mixture was stirred at 45° C. for 16 h. The organic volatiles were removed and the remaining aqueous solution was adjusted to pH=9 by 6N NaOH solution. The mixture was extracted with EtOAc three times. The combined organic layers were washed with brine, dried over $Na_2SO_4$, filtered and concentrated under reduced pressure. The residue was purified by column chromatography on silica gel to give compound 102b (700 mg, yield: 78%) as a white solid. MS (ESI): m/z 370.3 (M+H)$^+$.

Step 3: To a solution of triethyl phosphonoacetate (430 mg, 1.92 mmol) in dry THF (16 mL) at 0° C., sodium tert-butoxide (184 mg, 1.92 mmol) was added. After 10 min, a solution of compound 102b (700 mg, 1.90 mmol) in THF (4 mL) was added to the above mixture and the resulting reaction mixture was stirred for 2 h. The reaction was quenched by $H_2O$, extracted with EtOAc three times. The combined organic layers were washed with brine, dried over $Na_2SO_4$, filtered and concentrated under reduced pressure. The residue was purified by column chromatography on silica gel to give compound 102c (730 mg, yield: 88%) as a white solid. MS (ESI): m/z 440.4 (M+H)$^+$.

Step 4: To a suspension of NaH (60% w/w in mineral oil, 199 mg, 4.98 mmol) in DMSO (15 mL) was added trimethylsulfoxonium iodide (1.10 g, 4.98 mmol). After the mixture was stirred at r.t. for 1.5 h, a solution of compound 102c (730 mg, 1.66 mmol) in DMSO (5 mL) was added to the above mixture and the resulting reaction mixture was stirred at 40° C. for 16 h. The mixture was quenched by $H_2O$ and extracted with EtOAc. The organic layer was concentrated and the residue was purified by column chromatography on silica gel to give compound 102d (400 mg, yield: 53%) as a white solid. MS (ESI): m/z 454.3 (M+H)$^+$.

Step 5: To a mixture of 4-chloroaniline (447 mg, 3.52 mmol) in dry THF (5 mL) at 0° C., isopropylmagnesium chloride solution (2.0 M in THF, 1.8 mL, 3.52 mmol) was added dropwise. After the mixture was stirred at r.t. for 5 min, a solution of compound 102d (400 mg, 0.88 mmol) in dry THF (2 mL) was added dropwise. The resulting mixture was stirred at r.t. for 16 h. The reaction was quenched by aq. $NH_4Cl$ solution. The mixture was extracted with ethyl acetate three times and the combined organic layers were dried over $Na_2SO_4$, filtered and concentrated under reduced pressure. The residue was purified by column chromatography on silica gel to give compound 102e (400 mg, yield: 85%) as a white solid. MS (ESI): m/z 535.4 (M+H)$^+$.

Step 6: To a mixture of compound 102e (50 mg, 0.09 mmol) in DMF (5 mL) was added CuCN (20 mg, 0.22 mmol) and the mixture was stirred at 160° C. for 1 h. The reaction mixture was cooled to r.t. and quenched by aq. $NH_4Cl$ solution. The mixture was extracted with ethyl acetate three times and the combined organic layers were dried over $Na_2SO_4$, filtered and concentrated under reduced pressure. The residue was purified by Prep-HPLC to give compound 102 (17.23 mg, yield: 44%) as a white solid. MS (ESI): m/z 434.5 (M+H)$^+$. $^1$H NMR (500 MHz, d$_6$-DMSO) δ 10.38 (s, 1H), 8.96 (d, J=4.5 Hz, 1H), 8.72 (d, J=7.0 Hz, 1H), 8.37 (d, J=11.5 Hz, 1H), 7.65 (d, J=9.0 Hz, 2H), 7.51 (d, J=4.5 Hz, 1H), 7.34 (d, J=9.0 Hz, 2H), 3.53-3.43 (m, 1H), 2.23-2.15 (m, 1H), 1.96-1.83 (m, 4H), 1.77 (d, J=12.0 Hz, 1H), 1.74-1.69 (m, 1H), 1.34-1.24 (m, 1H), 1.16-1.07 (m, 2H), 0.93 (dd, J=7.5, 4.0 Hz, 1H).

Example 103

N-(4-chlorophenyl)-6-(2,3-dihydro-[1,4]dioxino[2,3-g]quinolin-9-yl)spiro[2.5]octane-1-carborboxamide

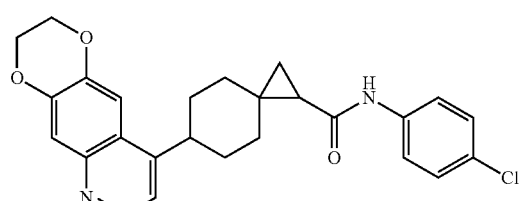

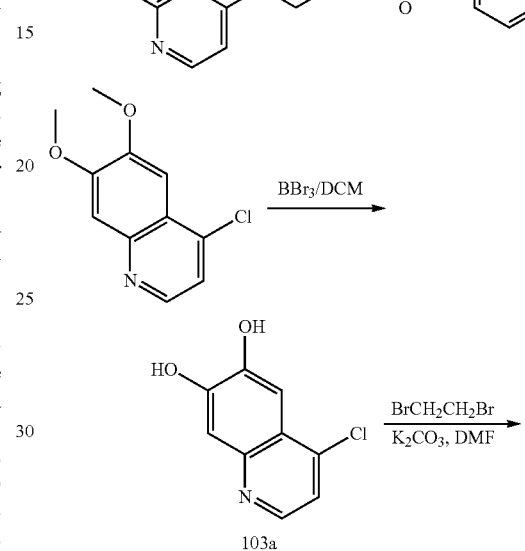

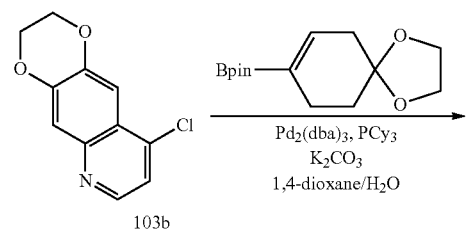

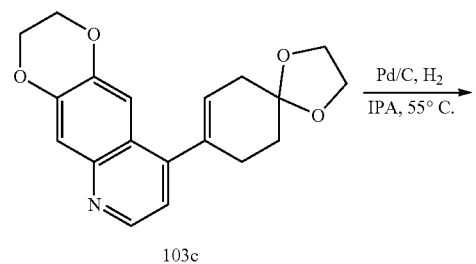

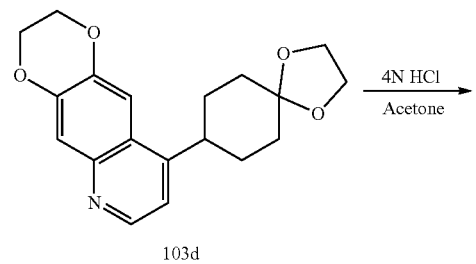

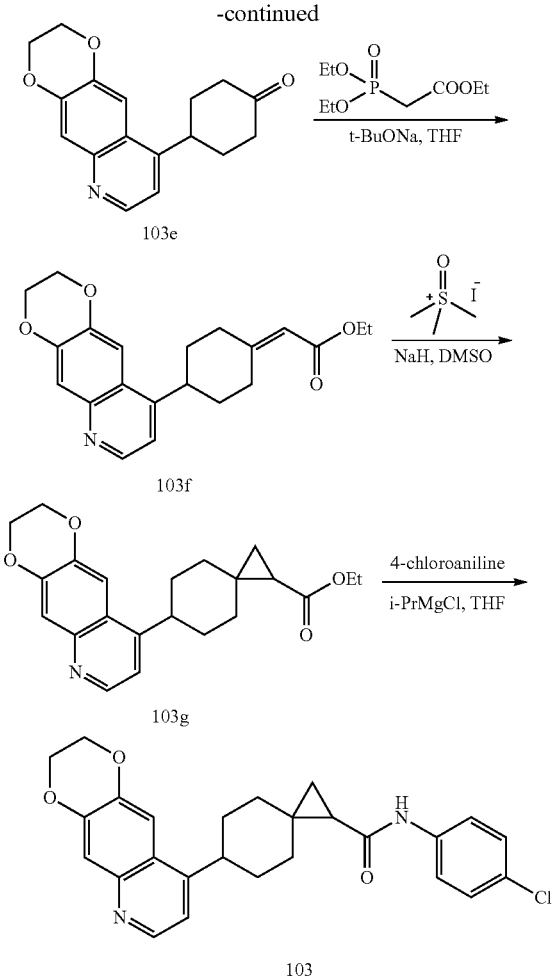

(40 mL) and water (10 mL) were added compound 103b (460 mg, 2.08 mmol), potassium carbonate (861 mg, 6.24 mmol), Pd$_2$(dba)$_3$ (95 mg, 0.104 mmol) and PCy$_3$ (70 mg, 0.25 mmol). The reaction mixture was stirred and refluxed under N$_2$ for 16 h. The mixture was concentrated under reduced pressure. The residue was diluted with H$_2$O and extracted with EtOAc. The organic layer was concentrated. The residue was purified by column chromatography on silica gel to afford compound 103c (550 mg, yield 81%) as a white solid. MS (ESI): m/z 326.6 (M+H)$^+$. $^1$H NMR (500 MHz, CDCl$_3$) δ 8.65 (d, J=4.5 Hz, 1H), 7.56 (s, 1H), 7.42 (s, 1H), 7.06 (d, J=4.5 Hz, 1H), 5.72 (t, J=3.5 Hz, 1H), 4.41-4.34 (m, 4H), 4.09-4.03 (m, 4H), 2.64-2.57 (m, 2H), 2.54-2.49 (m, 2H), 1.97 (t, J=6.5 Hz, 2H).

Step 4: To a solution of compound 103c (500 mg, 1.54 mmol) in isopropyl alcohol (25 mL) was added 10% w/w palladium on carbon (70 mg). The mixture was stirred at 55° C. under hydrogen atmosphere for 16 h. The reaction was filtered over a pad of celite. The filtrate was concentrated to give compound 103d (500 mg, yield: 99%) as a white solid, which was used to the next step directly. MS (ESI): m/z 328.4 (M+H)$^+$.

Step 5: To a solution of compound 103d (500 mg, 1.53 mmol) in acetone (36 mL) was added HCl (4N in water, 9 mL, 36 mmol) and the mixture was stirred at 45° C. for 16 h. The organic volatiles were removed and the remaining aqueous solution was adjusted to pH=9 by 6N NaOH solution. The mixture was extracted with EtOAc three times. The combined organic layers were washed with brine, dried over Na$_2$SO$_4$, filtered and concentrated under reduced pressure. The residue was purified by column chromatography on silica gel to give compound 103e (250 mg, yield: 58%) as a brown solid. MS (ESI): m/z 284.5 (M+H)$^+$. $^1$H NMR (500 MHz, CDCl$_3$) δ 8.68 (d, J=4.5 Hz, 1H), 7.60 (s, 1H), 7.49 (s, 1H), 7.10 (d, J=4.5 Hz, 1H), 4.41 (s, 4H), 3.68-3.61 (m, 1H), 2.68-2.57 (m, 4H), 2.39-2.31 (m, 2H), 2.07-1.96 (m, 2H).

Step 6: To a solution of triethyl phosphonoacetate (214 mg, 0.89 mmol) in dry THF (10 mL) at 0° C., sodium tert-butoxide (85 mg, 0.89 mmol) was added. After 10 min, a solution of compound 103e (250 mg, 0.88 mmol) in THF (4 mL) was added to the above mixture and the resulting reaction mixture was stirred for 2 h. The reaction was quenched by H$_2$O, extracted with EtOAc (20 mL×3). The combined organic layers were washed with brine (20 mL), dried over Na$_2$SO$_4$, filtered and concentrated under reduced pressure. The residue was purified by column chromatography on silica gel to give compound 103f (168 mg, yield: 54%) as a white solid. MS (ESI): m/z 354.5 (M+H)$^+$. $^1$H NMR (500 MHz, CDCl$_3$) δ 8.65 (d, J=4.5 Hz, 1H), 7.59 (s, 1H), 7.49 (s, 1H), 7.07 (d, J=4.5 Hz, 1H), 5.73 (s, 1H), 4.40 (s, 4H), 4.18 (q, J=7.0 Hz, 2H), 4.10-4.05 (m, 1H), 3.46-3.39 (m, 1H), 2.51-2.45 (m, 2H), 2.22-2.10 (m, 3H), 1.77-1.65 (m, 2H), 1.30 (t, J=7.0 Hz, 3H).

Step 7: To a suspension of NaH (60% w/w in mineral oil, 40 mg, 0.99 mmol) in DMSO (10 mL) was added trimethylsulfoxonium iodide (249 mg, 1.13 mmol). After the mixture was stirred at r.t. for 1.5 h, a solution of compound 103f (100 mg, 0.28 mmol) in DMSO (5 mL) was added to the above mixture and the resulting reaction mixture was stirred at 40° C. for 16 h. The mixture was quenched by H$_2$O and extracted with EtOAc. The organic layer was concentrated and the residue was purified by column chromatography on silica gel to give compound 103g (70 mg, yield: 68%) as a white solid. MS (ESI): m/z 368.5 (M+H)$^+$. $^1$H NMR (500 MHz, CDCl$_3$) δ 8.66 (d, J=4.5 Hz, 1H), 7.63 (s, 1H), 7.48 (s, 1H), 7.14 (d, J=4.5 Hz, 1H), 4.40 (s, 4H), 4.18 (q, J=7.0 Hz, 2H), Step 1: To a mixture of 4-chloro-6,7-dimethoxyquinoline (1.0 g, 4.48 mmol) in DCM (30 mL) was added BBr$_3$ (1.0 M in DCM, 12.0 mL, 12.0 mmol) at 0° C. The mixture was stirred at 0° C. for 2 h and then warmed to r.t. for 16 h until LCMS showed complete conversion of starting material. The reaction was quenched by H$_2$O (50 mL). The mixture was extracted with DCM (40 mL×2) and the combined organic layers were dried over Na$_2$SO$_4$, filtered and concentrated under reduced pressure to give compound 103a (800 mg, yield: 92%) as a yellow solid. MS (ESI): m/z 196.5 (M+H)$^+$. $^1$H NMR (500 MHz, d$_6$-DMSO) δ 10.33 (s, 2H), 8.47 (d, J=5.0 Hz, 1H), 7.42 (d, J=5.0 Hz, 1H), 7.36 (s, 1H), 7.30 (s, 1H).

Step 2: To a mixture of Compound 103a (800 mg, 4.10 mmol) in DMF (30 mL) were added potassium carbonate (2.12 g, 15.38 mmol) and 1,2-dibromoethane (3.84 g, 20.45 mmol) and the mixture was stirred at 60° C. for 2 h. The reaction was quenched by H$_2$O. The mixture was extracted with ethyl acetate three times and the combined organic layers were dried over Na$_2$SO$_4$, filtered and concentrated under reduced pressure. The residue was purified by column chromatography on silica gel to give compound 103b (520 mg, yield: 57%) as a white solid. MS (ESI): m/z 222.5 (M+H)$^+$. $^1$H NMR (500 MHz, CDCl$_3$) δ 8.59 (d, J=4.5 Hz, 1H), 7.62 (s, 1H), 7.58 (s, 1H), 7.33 (d, J=4.5 Hz, 1H), 4.40 (s, 4H).

Step 3: To a solution of 1,4-dioxaspiro[4,5]dec-7-en-8-boronic acid pinacol ester (664 mg, 2.50 mmol) in dioxane 3.27-3.19 (m, 1H), 2.13 (td, J=13.5, 3.5 Hz, 1H), 2.03-1.88 (m, 4H), 1.84-1.74 (m, 1H), 1.56 (dd, J=7.5, 5.5 Hz, 1H), 1.41-1.34 (m, 1H), 1.29 (t, J=7.0 Hz, 3H), 1.25-1.22 (m, 1H), 1.14-1.07 (m, 1H), 0.98 (dd, J=7.5, 4.5 Hz, 1H).

Step 8: To a mixture of 4-chloroaniline (81 mg, 0.64 mmol) in dry THF (5 mL) at 0° C., isopropylmagnesium chloride solution (2.0 M in THF, 0.3 mL, 0.64 mmol) was added dropwise. After the mixture was stirred at r.t. for 5 min, a solution of compound 103g (60 mg, 0.16 mmol) in dry THF (2 mL) was added dropwise. The resulting mixture was stirred at r.t. for 16 h. The reaction was quenched by aq. NH$_4$Cl solution. The mixture was extracted with ethyl acetate three times and the combined organic layers were dried over Na$_2$SO$_4$, filtered and concentrated under reduced pressure. The residue was purified by Prep-HPLC to give compound 103 (7.59 mg, yield: 11%) as a white solid. $^1$H NMR (500 MHz, d$_6$-DMSO) δ 10.37 (s, 1H), 8.58 (d, J=4.5 Hz, 1H), 7.64 (d, J=9.0 Hz, 2H), 7.57 (s, 1H), 7.36 (s, 1H), 7.34 (d, J=9.0 Hz, 2H), 7.10 (d, J=4.5 Hz, 1H), 4.38 (s, 4H), 3.36-3.33 (m, 1H), 2.20-2.12 (m, 1H), 1.97-1.84 (m, 4H), 1.77-1.68 (m, 2H), 1.33-1.24 (m, 1H), 1.16-1.06 (m, 2H), 0.92 (dd, J=7.5, 4.0 Hz, 1H).

Example 104

N-(4-chlorophenyl)-6-(6-fluoroquinolin-4-yl)-6-hydroxyspiro[2.5]octane-1-carboxamide

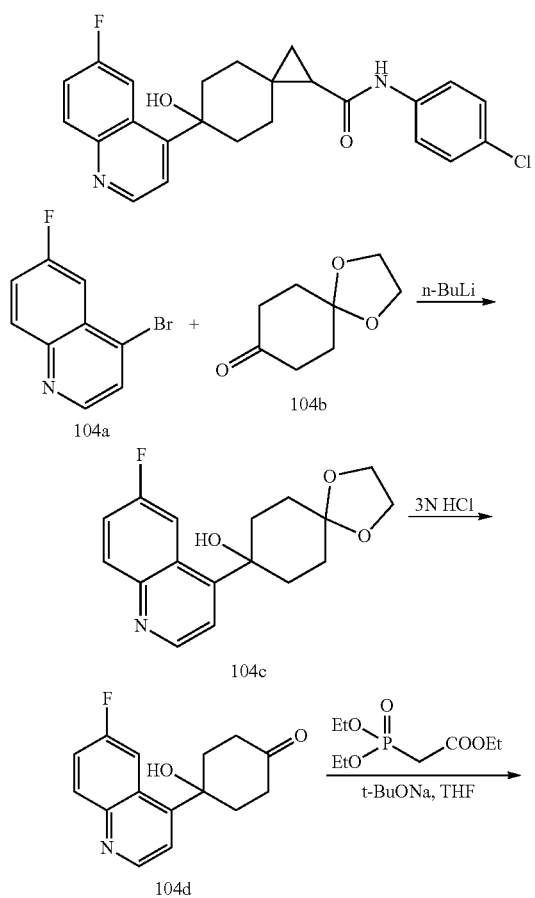

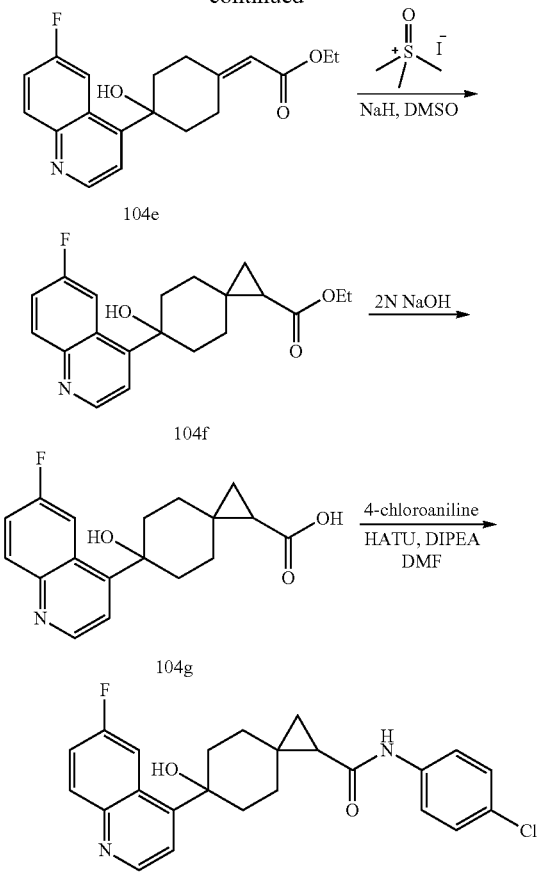

Step 1: To a mixture of 4-bromo-6-fluoroquinoline (500 mg, 2.21 mmol) in dry THF (5 mL) at −78° C., n-BuLi (1.6 M in hexane, 2.8 mL, 4.42 mmol) was added; the mixture was stirred at −78° C. for 5 min. Compound 104b (345 mg, 2.21 mmol) in dry THF (4 mL) was added to the above solution and the resulting mixture was stirred at −78° C. for 1 h. The reaction was quenched by aq. NH$_4$Cl solution. The mixture was extracted with ethyl acetate three times and the combined organic layers were washed with brine, dried over Na$_2$SO$_4$, filtered and concentrated under reduced pressure. The residue was purified by column chromatography on silica gel to give compound 104c (83 mg, yield: 12%) as a yellow solid. MS (ESI): m/z 304.6 (M+H)$^+$.

Step 2: To a solution of compound 104c (370 mg, 1.22 mmol) in THF (4 mL) was added HCl (3N in water, 3 mL, 9 mmol) and the mixture was stirred at 50° C. for 12 h. The mixture was cooled to r.t. and adjusted to pH=8 by saturated Na$_2$CO$_3$ solution. The mixture was extracted with EtOAc three times. The combined organic layers were washed with brine, dried over Na$_2$SO$_4$, filtered and concentrated under reduced pressure. The residue was purified by column chromatography on silica gel to give compound 104d (230 mg, yield 73%) as yellow oil. MS (ESI): m/z 260.6 (M+H)$^+$.

Step 3: To a solution of triethyl phosphonoacetate (280 mg, 1.25 mmol) in dry THF (16 mL) at 0° C., sodium tert-butoxide (120 mg, 1.25 mmol) was added. After 10 min, a solution of compound 104d (295 mg, 1.14 mmol) in THF (2 mL) was added to the above mixture and the resulting reaction mixture was stirred for 2 h. The reaction was quenched by H$_2$O, extracted with EtOAc three times. The combined organic layers were washed with brine, dried over Na₂SO₄, filtered and concentrated under reduced pressure. The residue was purified by column chromatography on silica gel to give compound 104e (183 mg, yield: 49%) as a white solid. MS (ESI): m/z 330.5 (M+H)⁺.

Step 4: To a suspension of NaH (60% w/w in mineral oil, 67 mg, 1.68 mmol) in DMSO (5 mL) was added trimethylsulfoxonium iodide (370 mg, 1.68 mmol). After the mixture was stirred at r.t. for 1.5 h, a solution of compound 104e (183 mg, 0.56 mmol) in DMSO (2 mL) was added to the above mixture and the resulting reaction mixture was stirred at r.t. for 16 h. The mixture was quenched by H₂O and extracted with EtOAc. The organic layer was concentrated and the residue was purified by Prep-TLC to give compound 104f (23 mg, yield: 12%) as colorless oil. MS (ESI): m/z 344.5 (M+H)⁺.

Step 5: To a solution of compound 104f (23 mg, 0.07 mmol) in ethanol (5 mL) was added NaOH (2N in water, 1.0 mL, 2.0 mmol) and the mixture was stirred at 50° C. for 2 h. The mixture was cooled to r.t. and adjusted to pH=5~6 by 2N HCl solution. The mixture was concentrated under reduced pressure. The residue was suspended in MeOH and filtered. The filtrate was concentrated under reduced pressure to give compound 104g (20 mg, yield 91%) as a white solid. MS (ESI): m/z 316.5 (M+H)⁺.

Step 6: To a solution of compound 104g (20 mg, 0.06 mmol) in DMF (2 mL) were added DIPEA (24 mg, 0.18 mmol) and HATU (34 mg, 0.09 mmol and the mixture was stirred at r.t. for 1 h. 4-chloroaniline (23 mg, 0.18 mmol) was added to the above mixture and the resulting reaction mixture was stirred at r.t. for 2 h. The mixture was quenched by H₂O and extracted with EtOAc three times. The combined organic layers were dried over Na₂SO₄, filtered and concentrated under reduced pressure. The residue was purified by Prep-HPLC to give compound 104 (5.85 mg, yield 20%) as a white solid. MS (ESI): m/z 425.6 (M+H)⁺. ¹H NMR (500 MHz, d₆-DMSO) δ 10.34 (s, 1H), 8.80 (d, J=4.5 Hz, 1H), 8.57 (d, J=12.0 Hz, 1H), 8.07 (dd, J=9.0, 6.0 Hz, 1H), 7.65-7.58 (m, 3H), 7.52 (d, J=4.5 Hz, 1H), 7.32 (d, J=9.0 Hz, 2H), 5.49 (s, 1H), 2.45-2.41 (m, 1H), 2.30-2.17 (m, 2H), 2.07 (d, J=13.5 Hz, 1H), 1.93 (d, J=13.5 Hz, 1H), 1.76-1.66 (m, 3H), 1.16-1.11 (m, 1H), 0.95-0.88 (m, 2H).

Example 105

N-(4-chlorophenyl)-6-(6-fluoro-7-methoxyquinolin-4-yl)spiro[2.5]octane-1-carboxamide

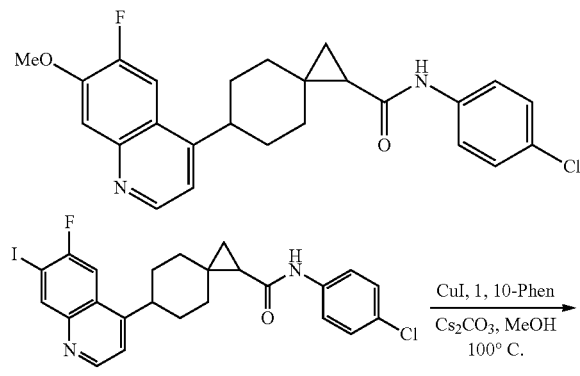

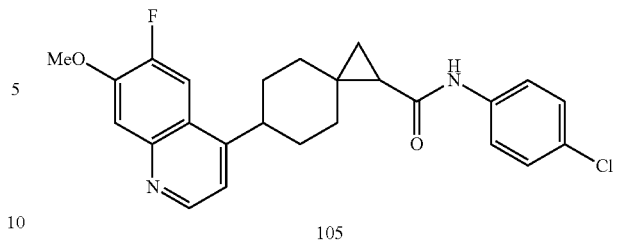

To a solution of compound 102e (50 mg, 0.09 mmol) in MeOH (2 mL) were subsequently added CuI (2 mg, 0.01 mmol), 1,10-phenanthroline (4 mg, 0.02 mmol) and Cs₂CO₃ (59 mg, 0.18 mmol). The reaction mixture was stirred at 100° C. under N₂ for 16 h. The mixture was quenched by H₂O and extracted with EtOAc three times. The combined organic layers were dried over Na₂SO₄, filtered and concentrated under reduced pressure. The residue was purified by Prep-HPLC to give compound 105 (15.90 mg, yield 40%) as a white solid. MS (ESI): m/z 439.5 (M+H)⁺. ¹H NMR (500 MHz, d₆-DMSO) δ 10.38 (s, 1H), 8.72 (d, J=4.5 Hz, 1H), 8.04 (d, J=13.0 Hz, 1H), 7.65 (d, J=8.5 Hz, 2H), 7.56 (d, J=9.0 Hz, 1H), 7.34 (d, J=8.5 Hz, 2H), 7.21 (d, J=4.5 Hz, 1H), 3.99 (s, 3H), 3.43-3.38 (m, 1H), 2.22-2.14 (m, 1H), 1.98-1.82 (m, 4H), 1.78-1.69 (m, 2H), 1.34-1.24 (m, 1H), 1.16-1.06 (m, 2H), 0.93 (dd, J=7.5, 4.0 Hz, 1H).

Example 106

N-(4-chlorophenyl)-6-(6-fluoroquinolin-4-yl)-1-methylspiro[2.5]octane-1-carboxamide

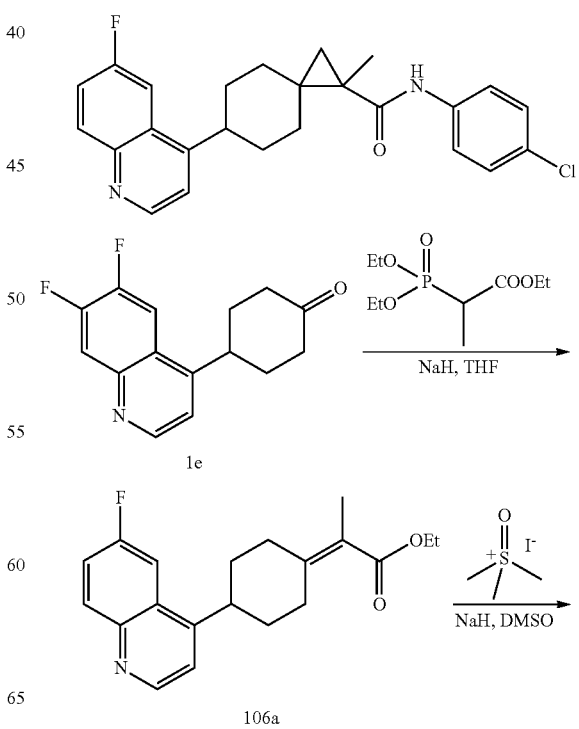

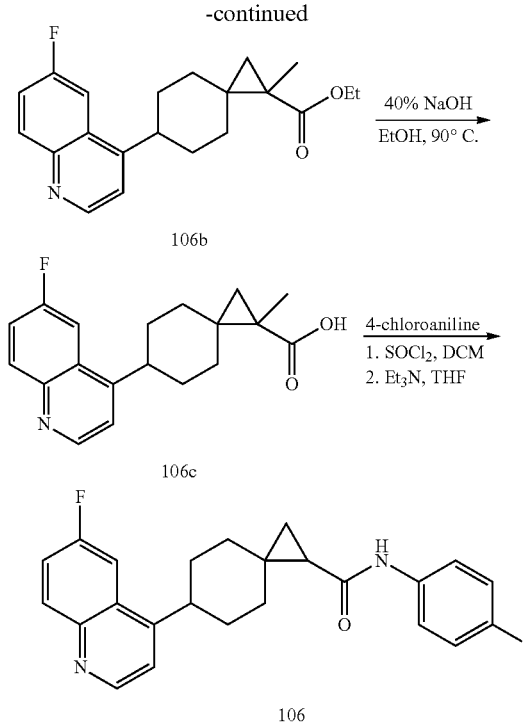

Step 1: To a suspension of NaH (60% w/w in mineral oil, 986 mg, 24.6 mmol) in dry THF (25 mL) was added ethyl-2-(diethylphosphono)propanoate (5.9 g, 24.6 mmol) at 0° C. After the mixture was stirred at 0° C. for 30 min, a solution of compound 1e (2.0 g, 8.2 mmol) in dry THF (10 mL) was added to the above mixture and the resulting reaction mixture was stirred at r.t. for 2 h. The mixture was quenched by aq. NH$_4$Cl and extracted with EtOAc (50 mL×3). The combined organic layers were washed with brine (50 mL), dried over dried over Na$_2$SO$_4$, filtered and concentrated under reduced pressure. The residue was purified by column chromatography on silica gel to give compound 106a (2.5 g, yield: 93%) as a white solid. MS (ESI): m/z 328.3 (M+H)$^+$. $^1$H NMR (500 MHz, CDCl$_3$) δ 8.81 (d, J=4.5 Hz, 1H), 8.26-8.18 (m, 1H), 7.74 (dd, J=10.5, 2.5 Hz, 1H), 7.56-7.48 (m, 1H), 7.31 (d, J=4.5 Hz, 1H), 4.23 (q, J=7.0 Hz, 2H), 3.50-3.40 (m, 1H), 3.32-3.25 (m, 1H), 2.94-2.87 (m, 1H), 2.24-2.10 (m, 4H), 1.94 (s, 3H), 1.78-1.65 (m, 2H), 1.33 (t, J=7.0 Hz, 3H).

Step 2: To a suspension of NaH (60% w/w in mineral oil, 734 mg, 18.36 mmol) in DMSO (20 mL) was added trimethylsulfoxonium iodide (4.04 g, 18.36 mmol). After the mixture was stirred at r.t. for 1.5 h, a solution of compound 106a (1.5 g, 4.59 mmol) in DMSO (10 mL) was added to the above mixture and the resulting reaction mixture was stirred at 70° C. for 16 h. The mixture was quenched by H$_2$O and extracted with EtOAc. The organic layer was concentrated and the residue was purified by column chromatography on silica gel to give compound 106b (726 mg, yield: 46%) as a pale-yellow solid. MS (ESI): m/z 342.4 (M+H)$^+$. $^1$H NMR (500 MHz, CDCl$_3$) δ 8.82 (d, J=4.5 Hz, 1H), 8.15 (dd, J=9.0, 6.0 Hz, 1H), 7.70 (dd, J=10.5, 2.5 Hz, 1H), 7.51-7.46 (m, 1H), 7.31 (d, J=4.5 Hz, 1H), 4.18 (q, J=7.0 Hz, 2H), 3.30-3.23 (m, 1H), 2.06-1.97 (m, 2H), 1.96-1.87 (m, 2H), 1.80-1.74 (m, 2H), 1.70-1.62 (m, 2H), 1.54-1.47 (m, 1H), 1.46 (s, 3H), 1.44 (d, J=5.0 Hz, 1H), 1.28 (t, J=7.0 Hz, 3H), 0.56 (d, J=5.0 Hz, 1H).

Step 3: To a solution of compound 106b (250 mg, 0.73 mmol) in ethanol (10 mL) was added NaOH (40% in water, 365 mg, 3.65 mmol) and the mixture was stirred at 90° C. for 5 h. The mixture was cooled to r.t. and adjusted to pH=1 by 6N HCl solution. The mixture was extracted with EtOAc three times. The combined organic layers were dried over Na$_2$SO$_4$, filtered and concentrated under reduced pressure. The residue was purified by Prep-TLC to give compound 106c (103 mg, yield: 45%) as a white solid. MS (ESI): m/z 314.4 (M+H)$^+$. $^1$H NMR (500 MHz, d$_6$-DMSO) δ 12.19 (s, 1H), 8.83 (d, J=4.5 Hz, 1H), 8.09 (dd, J=9.0, 6.0 Hz, 1H), 8.03 (dd, J=11.0, 3.0 Hz, 1H), 7.70-7.65 (m, 1H), 7.37 (d, J=4.5 Hz, 1H), 3.49-3.42 (m, 1H), 2.08-2.00 (m, 1H), 2.00-1.88 (m, 2H), 1.80 (d, J=13.0 Hz, 1H), 1.75-1.68 (m, 1H), 1.64-1.55 (m, 2H), 1.46-1.40 (m, 1H), 1.39 (s, 3H), 1.20 (d, J=4.0 Hz, 1H), 0.55 (d, J=4.0 Hz, 1H).

Step 4: To a solution of compound 106c (50 mg, 0.16 mmol) in dry DCM (5 mL) was added thionyl chloride (2.5 mL) and the mixture was stirred and refluxed for 2 h. The reaction mixture was concentrated under reduced pressure to give a pale-yellow solid, which was dissolved in dry THF (5 mL). 4-Chloroaniline (41 mg, 0.32 mmol) was added to the above solution, followed by Et$_3$N (48 mg, 0.48 mmol) at 0° C. The resulting mixture was stirred at 0° C. for 30 min and then warmed to r.t. for 2 h. The reaction was quenched by H$_2$O. The mixture was extracted with EtOAc three times and the combined organic layers were dried over Na$_2$SO$_4$, filtered and concentrated under reduced pressure. The residue was purified by Prep-HPLC to give compound 106 (40.24 mg, yield: 60%) as a white solid. MS (ESI): m/z 423.4 (M+H)$^+$. $^1$H NMR (500 MHz, d$_6$-DMSO) δ 9.69 (s, 1H), 8.87 (s, 1H), 8.11-8.06 (m, 1H), 8.03 (d, J=11.0 Hz, 1H), 7.70-7.64 (m, 3H), 7.55 (s, 1H), 7.35 (d, J=7.5 Hz, 2H), 3.45-3.38 (m, 1H), 2.06-1.82 (m, 4H), 1.72-1.67 (m, 1H), 1.64-1.60 (m, 1H), 1.54 (s, 3H), 1.38-1.33 (m, 1H), 1.32-1.28 (m, 1H), 0.96-0.88 (m, 1H), 0.48-0.43 (m, 1H).

Example 107

N-(4-chlorophenyl)-1-cyano-6-(6-fluoroquinolin-4-yl)spiro[2.5]octane-1-carboxamide

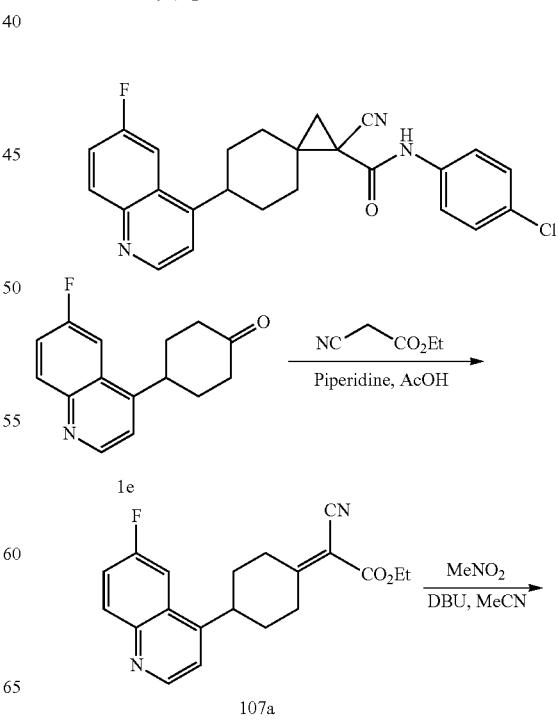

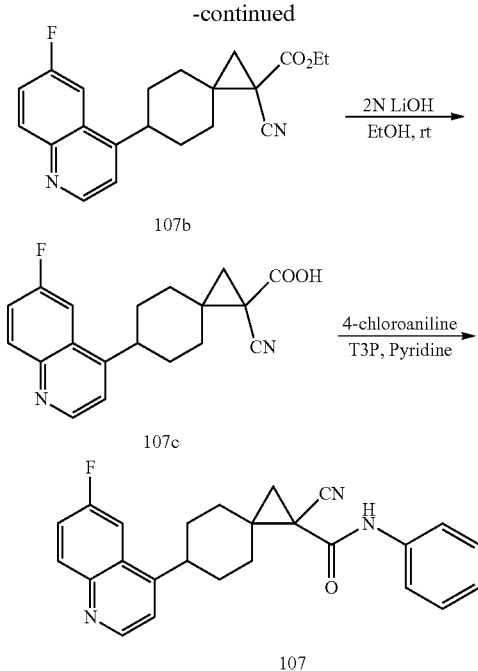

Step 1: To a solution of compound 1e (1.5 g, 6.17 mmol) in toluene (30 mL) were subsequently added with ethyl cyanoacetate (1.05 g, 9.25 mmol), piperidine (105 mg, 1.23 mmol) and AcOH (74 mg, 1.23 mmol). The reaction mixture was stirred at 120° C. for 1 h. The mixture was concentrated under reduced pressure. The residue was diluted with H$_2$O (100 mL) and extracted with DCM three times. The combined organic layers were dried over Na$_2$SO$_4$, filtered and concentrated under reduced pressure. The residue was purified by column chromatography on silica gel to give compound 107a (1.8 g, yield 86%) as a yellow solid. MS (ESI): m/z 339.4 (M+H)$^+$. $^1$H NMR (500 MHz, CDCl$_3$) δ 8.83 (d, J=4.5 Hz, 1H), 8.16 (dd, J=9.0, 6.0 Hz, 1H), 7.70 (dd, J=10.5, 3.0 Hz, 1H), 7.52 (ddd, J=10.5, 9.0, 3.0 Hz, 1H), 7.26 (d, J=4.5 Hz, 1H), 4.32 (q, J=7.0 Hz, 2H), 4.27-4.21 (m, 1H), 3.56 (tt, J=12.0, 3.0 Hz, 1H), 3.36-3.30 (m, 1H), 2.64 (td, J=14.0, 4.5 Hz, 1H), 2.42-2.27 (m, 3H), 1.93-1.84 (m, 1H), 1.84-1.75 (m, 1H), 1.38 (t, J=7.0 Hz, 3H).

Step 2: To a solution of compound 107a (1.8 g, 5.33 mmol) in MeCN (30 mL) were subsequently added nitromethane (486 mg, 7.98 mmol) and DBU (972 mg, 6.38 mmol). The reaction mixture was stirred at 25° C. for 16 h. The mixture was concentrated under reduced pressure. The residue was diluted with H$_2$O (100 mL) and extracted with DCM three times. The combined organic layers were dried over Na$_2$SO$_4$, filtered and concentrated under reduced pressure. The residue was purified by column chromatography on silica gel to give compound 107b (1.5 g, yield 80%) as a yellow solid. MS (ESI): m/z 353.4 (M+H)$^+$. $^1$H NMR (500 MHz, d$_6$-DMSO) δ 9.06 (d, J=4.5 Hz, 1H), 8.38-8.29 (m, 2H), 7.98-7.90 (m, 1H), 7.71 (d, J=4.5 Hz, 1H), 4.27 (q, J=7.0 Hz, 2H), 3.78-3.70 (m, 1H), 2.46-2.36 (m, 1H), 2.22-2.13 (m, 1H), 2.11-2.04 (m, 1H), 1.96-1.89 (m, 1H), 1.88-1.77 (m, 3H), 1.76-1.66 (m, 1H), 1.65-1.58 (m, 1H), 1.34-1.29 (m, 1H), 1.27 (t, J=7.0 Hz, 3H).

Step 3: To a solution of compound 107b (100 mg, 0.28 mmol) in ethanol (20 mL) was added LiOH (2 M in water, 10 mL) and the mixture was stirred at 25° C. for 4 h. The organic volatiles were removed and the remaining aqueous solution was adjusted to pH=4~5 by 4N HCl solution. The mixture was concentrated under reduced pressure. The residue was purified by Prep-TLC to give compound 107c (50 mg, yield: 54%) as a white solid. MS (ESI): m/z 325.5 (M+H)$^+$.

Step 4: To a solution of compound 107c (50 mg, 0.15 mmol) in THF (5 mL) were subsequently added pyridine (36 mg, 0.45 mmol) and 2,4,6-Tripropyl-1,3,5,2,4,6-Trioxatriphosphorinane-2,4,6-Trioxide (50% wt in EtOAc, 146 mg, 0.23 mmol) and the mixture was stirred at r.t. for 10 min. 4-chloroaniline (65 mg, 0.39 mmol) was added to the above mixture and the resulting reaction mixture was stirred at r.t. for 16 h. The mixture was diluted with H$_2$O (20 mL) and extracted with EtOAc three times. The combined organic layers were dried over Na$_2$SO$_4$, filtered and concentrated under reduced pressure. The residue was purified by Prep-HPLC to give compound 107 (4.34 mg, yield 7%) as a white solid. MS (ESI): m/z 434.3 (M+H)$^+$. $^1$H NMR (500 MHz, d$_6$-DMSO) δ 10.85 (s, 1H), 8.91 (d, J=4.5 Hz, 1H), 8.12-8.07 (m, 2H), 7.71-7.63 (m, 4H), 7.41 (d, J=9.0 Hz, 2H), 3.56-3.49 (m, 1H), 2.39-2.32 (m, 1H), 2.18-2.06 (m, 2H), 1.97-1.91 (m, 2H), 1.79-1.73 (m, 1H), 1.63-1.58 (m, 2H), 1.57-1.51 (m, 1H), 1.44-1.38 (m, 1H).

Example 108

(1S)-N-(4-chlorophenyl)-6-(6-fluoro-7-methoxyquinolin-4-yl)spiro[2.5]octane-1-carboxamide

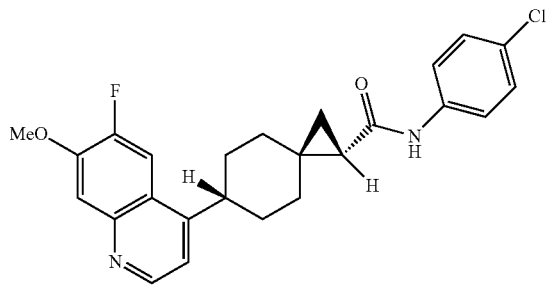 [SMILES: COc1cc2nccc([C@H]3CC[C@@]4(CC3)C[C@@H]4C(=O)Nc3ccc(Cl)cc3)c2cc1F]

Example 109

(1R)-N-(4-chlorophenyl)-6-(6-fluoro-7-methoxyquinolin-4-yl)spiro[2.5]octane-1-carboxamide

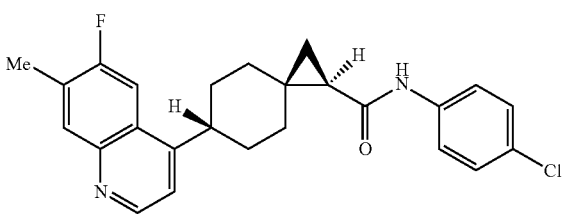 [SMILES: Cc1cc2nccc([C@H]3CC[C@@]4(CC3)C[C@H]4C(=O)Nc3ccc(Cl)cc3)c2cc1F]

Compound 108 and Compound 109 were obtained by chiral column separation of compound 105. Absolute stereochemistry arbitrarily assigned.

Compound 108: MS (ESI): m/z 439.5 (M+H)$^+$. $^1$H NMR (500 MHz, d$_6$-DMSO) δ 10.38 (s, 1H), 8.72 (d, J=4.5 Hz, 1H), 8.04 (d, J=13.0 Hz, 1H), 7.65 (d, J=8.5 Hz, 2H), 7.56 (d, J=9.0 Hz, 1H), 7.34 (d, J=8.5 Hz, 2H), 7.21 (d, J=4.5 Hz, 1H), 3.99 (s, 3H), 3.43-3.38 (m, 1H), 2.22-2.14 (m, 1H), 1.98-1.82 (m, 4H), 1.78-1.69 (m, 2H), 1.34-1.24 (m, 1H), 1.16-1.06 (m, 2H), 0.93 (dd, J=7.5, 4.0 Hz, 1H).

Compound 109: MS (ESI): m/z 439.5 (M+H)$^+$. $^1$H NMR (500 MHz, d$_6$-DMSO) δ 10.38 (s, 1H), 8.72 (d, J=4.5 Hz, 1H), 8.04 (d, J=13.0 Hz, 1H), 7.65 (d, J=8.5 Hz, 2H), 7.56 (d, J=9.0 Hz, 1H), 7.34 (d, J=8.5 Hz, 2H), 7.21 (d, J=4.5 Hz, 1H), 3.99 (s, 3H), 3.43-3.38 (m, 1H), 2.22-2.14 (m, 1H), 1.98-1.82 (m, 4H), 1.78-1.69 (m, 2H), 1.34-1.24 (m, 1H), 1.16-1.06 (m, 2H), 0.93 (dd, J=7.5, 4.0 Hz, 1H).

Example 110

6-([1,3]dioxolo[4,5-g]quinolin-8-yl)-N-(4-chlorophenyl)spiro[2.5]octane-1-carboxamide

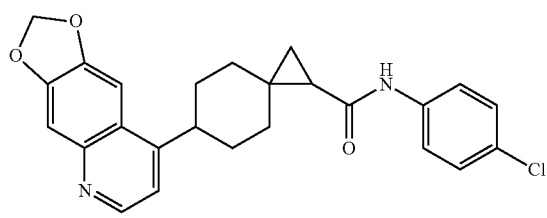 [SMILES: O=C(Nc1ccc(Cl)cc1)C1CC12CCC(c1ccnc3cc4c(cc13)OCO4)CC2]

Compound 110 was prepared from intermediate 103a (example 103), following the steps below:

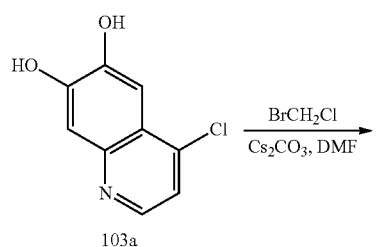

103a

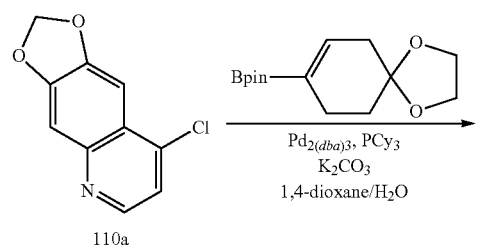

110a

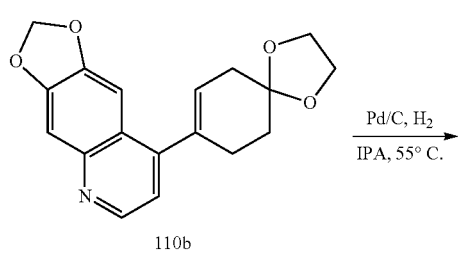

110b

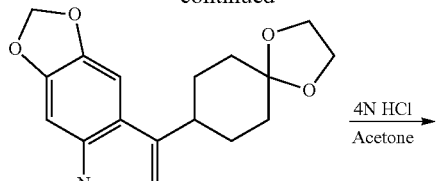

110c

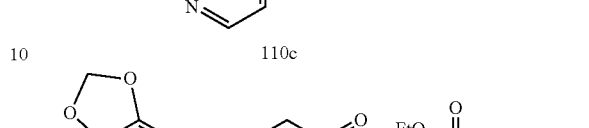

110d

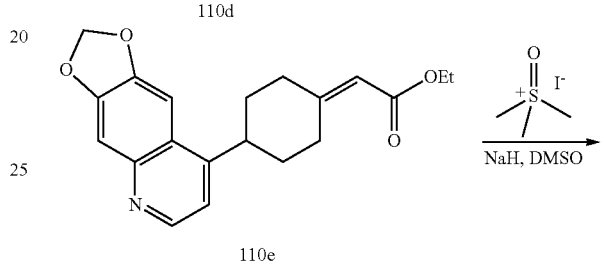

110e

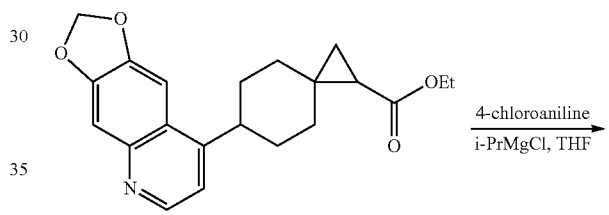

110f

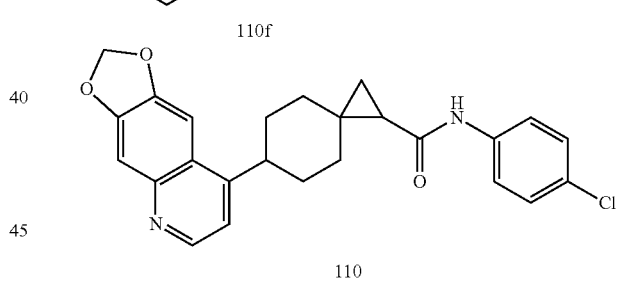

110

Step 1: To a solution of compound 103a (1.0 g, 5.13 mmol) in DMF (20 mL) was added bromochloromethane (986 mg, 7.70 mmol), and Cs$_2$CO$_3$ (2.51 g, 7.70 mmol). The mixture was heated to 110° C. for 2 hours. After cooling to room temperature, the reaction was quenched with water, extracted with EA. The organic layer was washed with brine, dried over Na$_2$SO$_4$, filtered and concentrated. The residue was purified by FCC to give compound 110a (480 mg, 45% yield) as a white solid. MS (ESI): m/z 208.4 (M+H)$^+$.

Step 2: A mixture of 2-(1,4-dioxaspiro[4.5]dec-7-en-8-yl)-4,4,5,5-tetramethyl-1,3,2-dioxaborolane (741 mg, 2.78 mmol), compound 110a (480 mg, 2.32 mmol), K$_2$CO$_3$ (960 mg, 6.96 mmol), Pd$_2$(dba)$_3$ (106 mg, 0.116 mmol) and PCy$_3$ (78 mg, 0.28 mmol) in 1,4-dioxane/H$_2$O (40 mL/10 mL) was heated to reflux under N$_2$ atmosphere overnight. The solution was then concentrated and extracted with EtOAc. The organic layer was concentrated and purified by FCC give compound 110b (540 mg, 75% yield) as a white solid. MS (ESI): m/z 312.5 (M+H)$^+$.

Step 3: To a solution of compound 110b (500 mg, 1.61 mmol) in IPA (25 mL) was added 10% Pd/C (70 mg). The mixture was stirred under an atmosphere of $H_2$ (balloon) at 55° C. overnight. Then the mixture was filtered and concentrated to give compound 110c (500 mg, 99% yield) as a white solid, which was used directly to the next step. MS (ESI): m/z 314.4 $(M+H)^+$.

Step 4: To a solution of compound 110c (500 mg, 1.60 mmol) in acetone (36 mL) was added 4M HCl (9 mL, 36 mmol). The mixture was heated at 45° C. overnight, then concentrated in vacuo. The residue was adjusted to pH 9 with 6 N NaOH, and the mixture was partitioned between EA and water. The organic layer was washed with brine, dried over $Na_2SO_4$, filtered and concentrated. The residue was purified by FCC to give compound 110d (255 mg, 59% yield) as a white solid. MS (ESI): m/z 270.5 $(M+H)^+$.

Step 5: To a solution of ethyl 2-diethoxyphosphorylacetate (235 mg, 1.05 mmol) in dry THF (10 mL) was added t-BuONa (101 mg, 1.05 mmol) at 0° C. After 10 minutes, a solution of compound 110d (255 mg, 0.95 mmol) in dry THF (4 mL) was added to the reaction. After 2 additional hours, the reaction was quenched with water, extracted with EA. The combined organics were washed with brine, dried over $Na_2SO_4$, filtered, and concentrated. The residue was purified by FCC to give compound 110e (210 mg, 65% yield) as a white solid. MS (ESI): m/z 340.5 $(M+H)^+$.

Step 6: To a suspension of NaH (35 mg, 0.87 mmol) in DMSO (10 mL) was added trimethylsulfoxonium iodide (191 mg, 0.87 mmol), and the mixture was stirred at rt for 1.5 h. Then a solution of compound 110e (100 mg, 0.29 mmol) in DMSO (5 mL) was added. The reaction was stirred at 40° C. overnight, then quenched with water, extracted with EtOAc, and purified by FCC to give compound 110f (78 mg, 76% yield) as a white solid. MS (ESI): m/z 354.5 $(M+H)^+$.

Step 7: To a solution of 4-chloroaniline (86 mg, 0.68 mmol) in THF (5 mL) was added i-PrMgCl (2.0 mol/L, 0.4 mL, 0.68 mmol) at 0° C. Then mixture was stirred at rt for 5 minutes, and a solution of compound 110f (60 mg, 0.17 mmol) in THF (2 mL) was added. The reaction was stirred at rt overnight, and quenched with saturated $NH_4Cl$ aqueous, extracted with EtOAc. The combined organic layer was dried over $Na_2SO_4$, filtered, and concentrated. The residue was further purified by reversed pre-HPLC to give compound 110 (10.28 mg, 14% yield) as a white solid. MS (ESI): m/z 435.5 $(M+H)^+$. $^1H$ NMR (500 MHz, $d_6$-DMSO) δ 10.36 (s, 1H), 8.56 (d, J=4.5 Hz, 1H), 7.65 (d, J=9.0 Hz, 2H), 7.58 (s, 1H), 7.37 (s, 1H), 7.34 (d, J=9.0 Hz, 2H), 7.11 (d, J=4.5 Hz, 1H), 5.02 (s, 2H), 3.36-3.32 (m, 1H), 2.21-2.12 (m, 1H), 1.97-1.85 (m, 4H), 1.78-1.68 (m, 2H), 1.32-1.24 (m, 1H), 1.17-1.06 (m, 2H), 0.91 (dd, J=7.5, 4.0 Hz, 1H).

Example 111

Methyl 2-(4-(6-(6-fluoro-7-methylquinolin-4-yl)spiro[2.5]octane-1-carboxamido)phenoxy)acetate

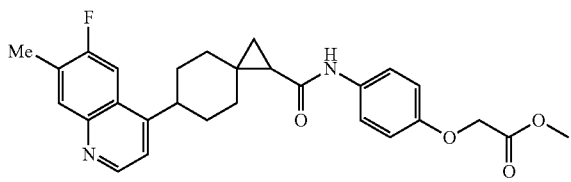 [SMILES: COC(=O)COc1ccc(NC(=O)C2CC23CCC(c2ccnc4cc(C)c(F)cc24)CC3)cc1]

Compound 111 was prepared from intermediate 94a (example 94), following the steps below:

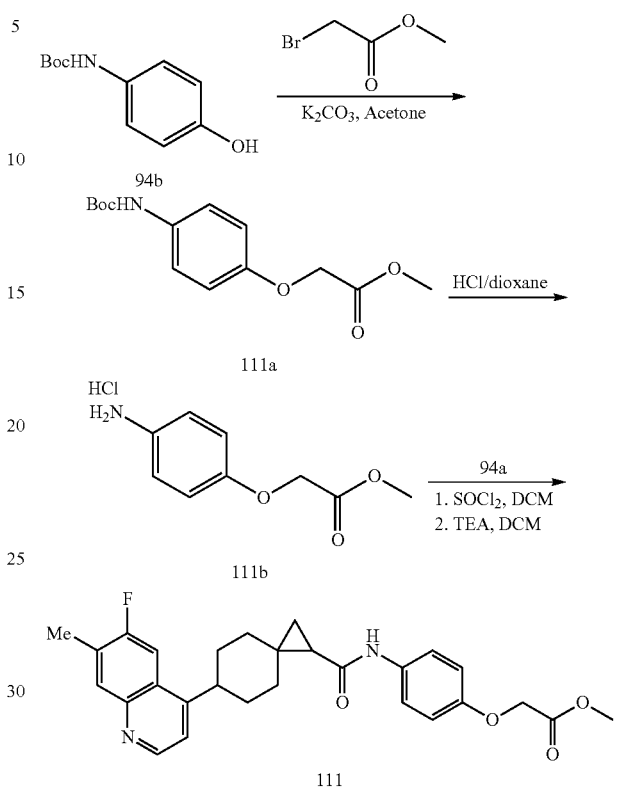

Step 1: To a solution of compound 94b (1.0 g, 4.78 mmol) and methyl bromoacetate (1.46 g, 9.56 mmol) in acetone (15 mL) was added $K_2CO_3$ (1.98 g, 14.34 mmol). The mixture was heated to 60° C. for 2 hours. The reaction was filtered and concentrated. The residue was purified by FCC to give compound 11a (822 mg, 61% yield) as a white solid. $^1H$ NMR (500 MHz, $CDCl_3$) δ 7.27 (d, J=9.0 Hz, 2H), 6.85 (d, J=9.0 Hz, 2H), 6.36 (s, 1H), 4.60 (s, 2H), 3.80 (s, 3H), 1.51 (s, 9H).

Step 2: To a solution of compound 111a (822 mg, 2.92 mmol) in DCM (15 mL) was added 4.0 mol/L HCl/dioxane (6 mL) at 0° C. The mixture was stirred at rt for 2 hours. The precipitate was filtered and dried to give compound 111b (550 mg, 86% yield) as a white solid, which was used directly to the next step.

Step 3: To a solution of compound 94a (53 mg, 0.17 mmol) in DCM (2 mL) was added $SOCl_2$ (5 mL). The mixture was heated to reflux for 2 hours. Then the solvent was evaporated, dried, and dissolved in DCM (3 mL). To this solution was added a solution of compound 111b (30 mg, 0.17 mmol) in DCM (2 mL) and TEA (52 mg, 0.51 mmol) at 0° C. The mixture was stirred for 10 min at 0° C., then warmed to rt and stirred for 2 hours. The reaction was quenched with water, extracted with EtOAc. The combined organic layer was dried over $Na_2SO_4$, filtered, and concentrated. The residue was further purified by reversed pre-HPLC to give compound 111 (32.56 mg, 40% yield) as a white solid. MS (ESI): m/z 477.5 $(M+H)^+$. $^1H$ NMR (500 MHz, $d_6$-DMSO) δ 10.13 (s, 1H), 8.75 (d, J=4.5 Hz, 1H), 7.98-7.92 (m, 2H), 7.50 (d, J=9.0 Hz, 2H), 7.29 (d, J=4.5 Hz, 1H), 6.87 (d, J=9.0 Hz, 2H), 4.74 (s, 2H), 3.69 (s, 3H), 3.48-3.39 (m, 1H), 2.45 (s, 3H), 2.19 (td, J=13.0, 3.5 Hz, 1H), 2.00-1.84 (m, 4H), 1.77 (d, J=12.0 Hz, 1H), 1.69 (dd, J=7.5, 5.0 Hz, 1H), 1.39-1.28 (m, 1H), 1.14-1.06 (m, 2H), 0.88 (dd, J=7.5, 4.0 Hz, 1H).

Example 112

6-(6-fluoro-7-methylquinolin-4-yl)-N-(4-(2-hydroxyethoxy)phenyl)spiro[2.5]octane-1-carboxamide

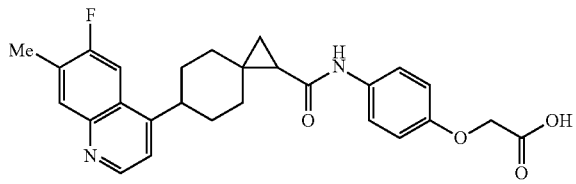 [SMILES: Cc1cc2nccc(C3CCC4(CC3)CC4C(=O)Nc3ccc(OCC(=O)O)cc3)c2cc1F]

Compound 112 was prepared from intermediate 94a (example 94), following the steps below:

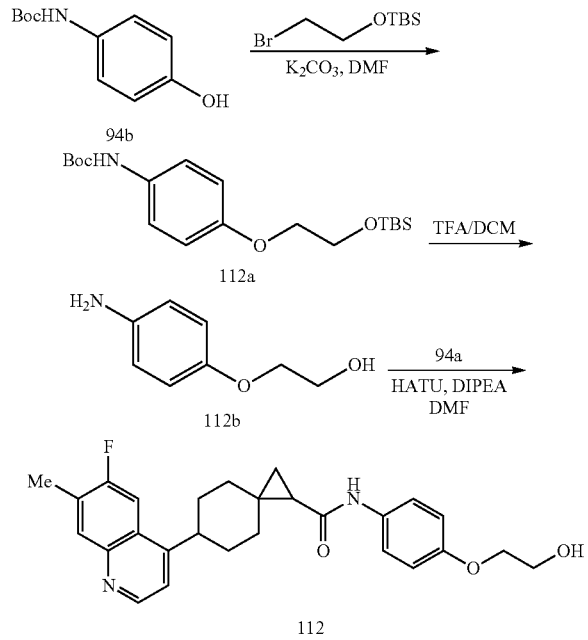

Step 1: To a solution of compound 94b (5.0 g, 23.90 mmol) in DMF (50 mL) was added 2-(tert-butyldimethylsilyloxy)-1-bromoethane (6.86 g, 28.68 mmol) and K₂CO₃ (5.0 g, 23.90 mmol). The mixture was heated to 80° C. overnight. The reaction was quenched with water, extracted with EtOAc. The combined organic layer was dried over Na₂SO₄, filtered, and concentrated. The residue was purified by FCC to give compound 112a (8.0 g, 91% yield) as a white solid. ¹H NMR (500 MHz, CDCl₃) δ 7.24 (d, J=9.0 Hz, 2H), 6.84 (d, J=9.0 Hz, 2H), 6.34 (s, 1H), 4.02-3.98 (m, 2H), 3.96-3.93 (m, 2H), 1.51 (s, 9H), 0.90 (s, 9H), 0.09 (s, 6H).

Step 2: To a solution of compound 112a (300 mg, 0.82 mmol) in DCM (2 mL) was added TFA/DCM (v/v=1:1, 10 mL) at 0° C. The mixture was stirred at rt overnight. The mixture was concentrated to give compound 112b (70 mg, 56% yield) as yellow oil, which was used directly to the next step. ¹H NMR (500 MHz, CDCl₃) δ 6.77 (d, J=8.5 Hz, 2H), 6.65 (d, J=8.5 Hz, 2H), 4.03-3.99 (m, 2H), 3.94-3.89 (m, 2H).

Step 3: To a solution of compound 94a (85 mg, 0.27 mmol) in DMF (5 mL) was added DIPEA (138 mg, 1.07 mmol) and HATU (122 mg, 0.32 mmol). The mixture was stirred at rt for 30 min, then added compound 112b (60 mg, 0.39 mmol). The mixture was stirred at 40° C. for 2 hours. The reaction was quenched with water, extracted with EtOAc. The combined organic layer was dried over Na₂SO₄, filtered, and concentrated. The residue was purified by reversed pre-HPLC to give compound 112 (69.60 mg, 58% yield) as a white solid. MS (ESI): m/z 449.5 (M+H)⁺. ¹H NMR (500 MHz, d₆-DMSO) δ 10.08 (s, 1H), 8.76 (d, J=4.5 Hz, 1H), 7.99-7.91 (m, 2H), 7.50 (d, J=9.0 Hz, 2H), 7.29 (d, J=4.5 Hz, 1H), 6.87 (d, J=9.0 Hz, 2H), 4.85 (br, 1H), 3.93 (t, J=5.0 Hz, 2H), 3.72-3.66 (m, 2H), 3.45-3.37 (m, 1H), 2.45 (s, 3H), 2.22-2.14 (m, 1H), 1.98-1.83 (m, 4H), 1.76 (d, J=11.5 Hz, 1H), 1.70-1.65 (m, 1H), 1.38-1.27 (m, 1H), 1.14-1.05 (m, 2H), 0.88 (dd, J=7.5, 4.0 Hz, 1H).

Example 113

6-(6,7-dimethoxyquinolin-4-yl)-N-(4-(2-methoxyethoxy)phenyl)spiro[2.5]octane-1-carboxamide

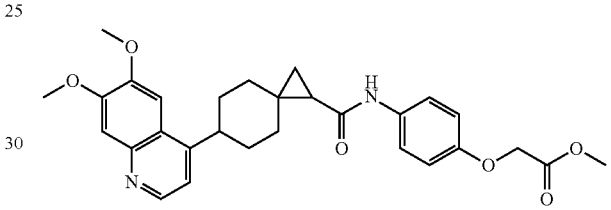

Compound 113 was prepared from intermediate 101e (example 101), following the steps below:

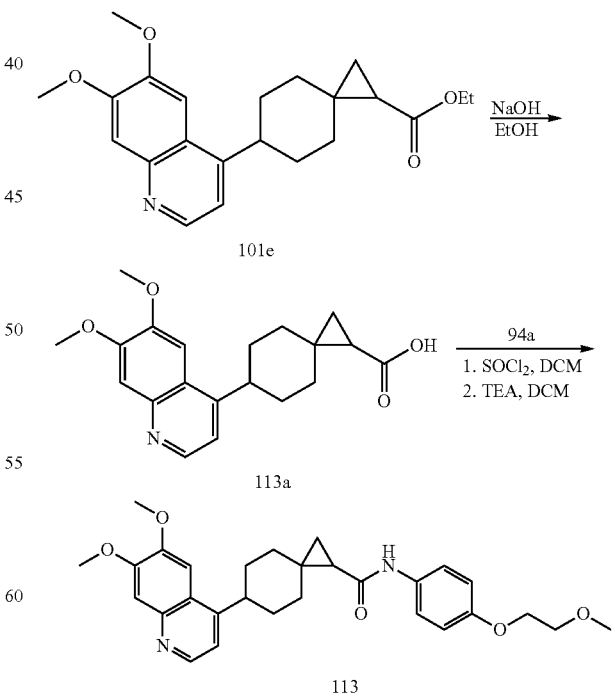

Step 1: To a solution of compound 101e (200 mg, 0.54 mmol) in EtOH (10 mL) was added 2.0 mol/L NaOH (4 mL). The mixture was heated to 50° C. for 2 hours. After cooling to room temperature, the reaction mixture was acidified by 4.0 mol/L HCl to pH=1. The aqueous was extracted with EtOAc. The combined organic layer was dried over Na₂SO₄, filtered, and concentrated. The residue was purified by pre-TLC to give compound 113a (130 mg, 71% yield) as a white solid. MS (ESI): m/z 342.5 (M+H)⁺.

Step 2: To a solution of compound 113a (58 mg, 0.17 mmol) in DCM (2 mL) was added SOCl₂ (5 mL). The mixture was heated to reflux for 2 hours. Then the solvent was evaporated, dried, and dissolved in DCM (3 mL). To this solution was added a solution of compound 94d (30 mg, 0.17 mmol) in DCM (2 mL) and TEA (52 mg, 0.51 mmol) at 0° C. The mixture was stirred for 10 min at 0° C., then warmed to rt and stirred for 2 hours. The reaction was quenched with water, extracted with EtOAc. The combined organic layer was dried over Na₂SO₄, filtered, and concentrated. The residue was further purified by reversed pre-HPLC to give compound 113 (40.86 mg, 49% yield) as a white solid. MS (ESI): m/z 491.5 (M+H)⁺. ¹H NMR (500 MHz, d₆-DMSO) δ 10.08 (s, 1H), 8.58 (d, J=4.5 Hz, 1H), 7.49 (d, J=9.0 Hz, 2H), 7.40 (s, 1H), 7.34 (d, J=4.5 Hz, 1H), 7.14 (s, 1H), 6.87 (d, J=9.0 Hz, 2H), 3.94 (s, 3H), 3.91 (s, 3H), 4.03 (t, J=4.5 Hz, 2H), 3.63 (t, J=4.5 Hz, 2H), 3.44-3.37 (m, 1H), 3.29 (s, 3H), 2.22-2.14 (m, 1H), 1.99-1.85 (m, 4H), 1.76 (d, J=12.0 Hz, 1H), 1.70-1.65 (m, 1H), 1.37-1.28 (m, 1H), 1.14-1.06 (m, 2H), 0.88 (dd, J=7.5, 4.0 Hz, 1H).

Example 114

N-(4-chlorophenyl)-6-(6-fluoro-7-(hydroxymethyl)quinolin-4-yl)spiro[2.5]octane-1-carboxamide

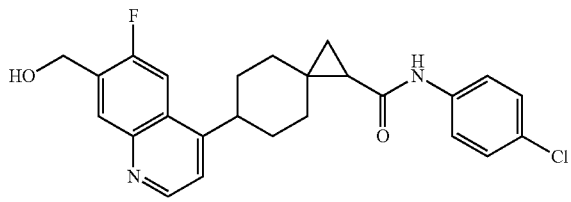 [SMILES: O=C(Nc1ccc(Cl)cc1)C1CC12CCC(c1ccnc3cc(CO)c(F)cc13)CC2]

Compound 114 was prepared from compound 102 (example 102), following the steps below:

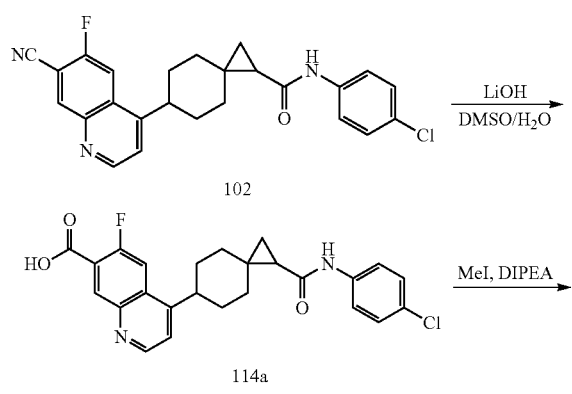

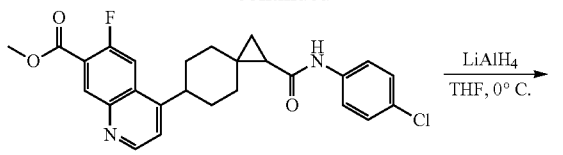

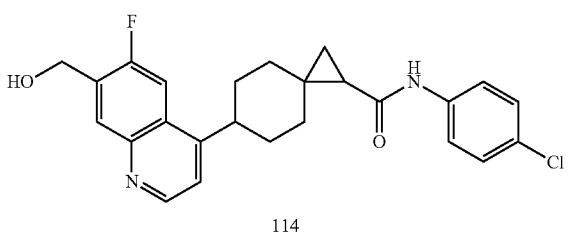

Step 1: To a solution of compound 102 (200 mg, 0.46 mmol) in DMSO/H₂O (5 mL/1 mL) was added LiOH (200 mg, 0.54 mmol). The mixture was heated to 50° C. for 3 hours, diluted with water, extracted with EtOAc. The aqueous was acidified by 2.0 mol/L HCl to pH=5-6, and extracted with EtOAc. The combined organic layer was dried over Na₂SO₄, filtered, and concentrated. The residue was purified by pre-TLC to give compound 114a (120 mg, 58% yield) as a white solid. MS (ESI): m/z 453.5 (M+H)⁺. ¹H NMR (500 MHz, d₆-DMSO) δ 10.38 (s, 1H), 8.80 (d, J=4.5 Hz, 1H), 8.26 (d, J=7.5 Hz, 1H), 7.96 (d, J=12.0 Hz, 1H), 7.65 (d, J=9.0 Hz, 2H), 7.38-7.31 (m, 3H), 3.48-3.39 (m, 1H), 2.23-2.16 (m, 1H), 1.96-1.84 (m, 4H), 1.77 (d, J=11.0 Hz, 1H), 1.74-1.69 (m, 1H), 1.35-1.27 (m, 1H), 1.17-1.07 (m, 2H), 0.92 (dd, J=7.5, 4.0 Hz, 1H).

Step 2: To a solution of compound 114a (60 mg, 0.13 mmol) in THF (5 mL) was added DIPEA (34 mg, 0.26 mmol) and MeI (28 mg, 0.20 mmol). The mixture was stirred at rt for 2 hours. The reaction was quenched with water, extracted with EtOAc. The combined organic layer was dried over Na₂SO₄, filtered, and concentrated. The residue was further purified by pre-TLC to give compound 114b (40 mg, 66% yield) as a white solid. MS (ESI): m/z 467.5 (M+H)⁺.

Step 3: To a solution of compound 114b (40 mg, 0.09 mmol) in THF (5 mL) was added LiAlH₄ (7 mg, 0.18 mmol) at 0° C. The mixture was slowly warmed to rt and stirred for 2 hours. The reaction was quenched with water, extracted with EtOAc. The combined organic layer was dried over Na₂SO₄, filtered, and concentrated. The residue was further purified by reversed pre-HPLC to give compound 114 (13.74 mg, 35% yield) as a white solid. MS (ESI): m/z 439.5 (M+H)⁺. ¹H NMR (500 MHz, d₆-DMSO) δ 10.37 (s, 1H), 8.78 (d, J=4.5 Hz, 1H), 8.07 (d, J=7.5 Hz, 1H), 7.97 (d, J=12.5 Hz, 1H), 7.65 (d, J=9.0 Hz, 2H), 7.34 (d, J=9.0 Hz, 2H), 7.31 (d, J=4.5 Hz, 1H), 5.51 (t, J=5.5 Hz, 1H), 4.74 (d, J=5.0 Hz, 2H), 3.46-3.38 (m, 1H), 2.23-2.15 (m, 1H), 1.98-1.83 (m, 4H), 1.77 (d, J=11.5 Hz, 1H), 1.74-1.69 (m, 1H), 1.34-1.25 (m, 1H), 1.17-1.13 (m, 2H), 1.10 (d, J=13.0 Hz, 1H), 0.93 (dd, J=7.5, 4.0 Hz, 1H).

Example 115

N-(4-chlorophenyl)-6-(6-fluoro-7-(methoxymethyl)quinolin-4-yl)spiro[2.5]octane-1-carboxamide

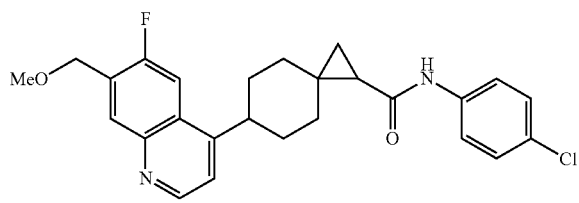 [SMILES: COCc1cc2nccc(C3CCC4(CC3)CC4C(=O)Nc3ccc(Cl)cc3)c2cc1F]

Compound 115 was prepared from compound 1d (example 1), following the steps below:

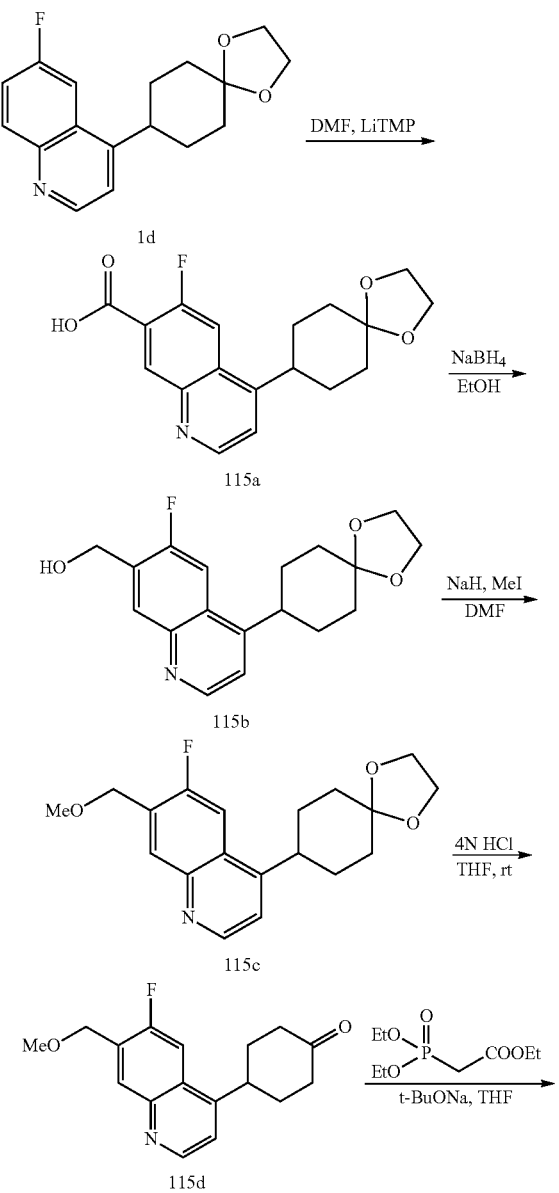

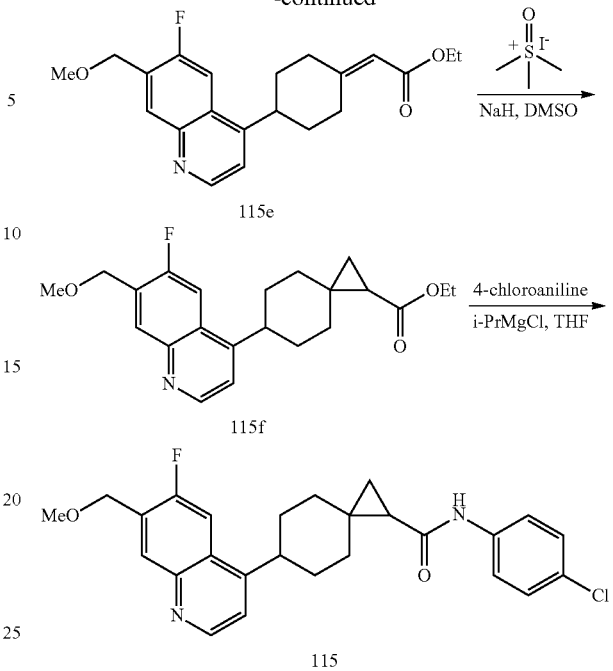

Step 1: To a solution of 2,2,6,6-tetramethylpiperidine (1.47 g, 10.44 mmol) in THF (50 mL) at −78° C. was added n-BuLi (2.5 M in hexane, 4.2 mL, 10.46 mmol). Then, a solution of compound 1d (2.00 g, 6.96 mmol) in THF (20 mL) was added dropwise and stirred for 2 hours. Then N,N-dimethylformamide (1.02 g, 13.92 mmol) in THF (10 mL) was added dropwise. The mixture was stirred at −78° C. for 30 min and then slowly warmed to room temperature and stirred for another 2 hours, then quenched by NH$_4$Cl aqueous, extracted with EtOAc. The combined organic layer was dried over Na$_2$SO$_4$, filtered, and concentrated. The residue was further purified by FCC to give compound 115a (1.8 g, 82% yield) as a white solid. MS (ESI): m/z 316.5 (M+H)$^+$.

Step 2: To a solution of compound 115a (1.0 g, 3.17 mmol) in EtOH (10 mL) was added NaBH$_4$ (241 mg, 6.35 mmol) at 0° C. The reaction was slowly warmed to room temperature and stirred for 1 hour, then quenched by water, extracted with EtOAc. The combined organic layer was dried over Na$_2$SO$_4$, filtered, and concentrated. The residue was further purified by FCC to give compound 115b (980 mg, 97% yield) as a white solid. MS (ESI): m/z 318.5 (M+H)$^+$.

Step 3: To a solution of compound 115b (980 mg, 3.09 mmol) in DMF (10 mL) was added NaH (247 mg, 6.18 mmol) at 0° C. The reaction was stirred at 0° C. for 30 min, then MeI (527 mg, 3.71 mmol) was added. The mixture was stirred at rt for 3 hours, then quenched by water, extracted with EtOAc. The combined organic layer was dried over Na$_2$SO$_4$, filtered, and concentrated. The residue was further purified by FCC to give compound 115c (760 mg, 74% yield) as a white solid. MS (ESI): m/z 332.5 (M+H)$^+$.

Step 4: To a solution of compound 115c (760 mg, 2.30 mmol) in THF (20 mL) was added 4.0 mol/L HCl (6 mL, 24 mmol). The mixture was stirred at rt for 5 hours, then concentrated in vacuo. The aqueous was adjusted to pH=9 with 6.0 mol/L NaOH, and the mixture was partitioned between EA and water. The organic layer was washed with brine, dried over Na$_2$SO$_4$, filtered and concentrated. The residue was purified by FCC to give compound 115d (423 mg, 64% yield) as a white solid. MS (ESI): m/z 288.4 (M+H)+.

Step 5: To a solution of ethyl 2-diethoxyphosphorylacetate (345 mg, 1.54 mmol) in dry THF (10 mL) was added t-BuONa (148 mg, 1.54 mmol) at 0° C. After 10 minutes, a solution of compound 115d (423 mg, 1.47 mmol) in dry THF (5 mL) was added to the reaction. After 2 additional hours, the reaction was quenched with water, extracted with EA. The combined organics were washed with brine, dried over $Na_2SO_4$, filtered, and concentrated. The residue was purified by FCC to give compound 115e (500 mg, 95% yield) as a white solid. MS (ESI): m/z 358.4 (M+H)+.

Step 6: To a suspension of NaH (67 mg, 1.68 mmol) in DMSO (15 mL) was added trimethylsulfoxonium iodide (370 mg, 1.68 mmol), and the mixture was stirred at rt for 1.5 h. Then a solution of compound 115e (200 mg, 0.56 mmol) in DMSO (5 mL) was added. The reaction was stirred at 40° C. overnight, then quenched with water, extracted with EtOAc, and purified by FCC to give compound 115f (145 mg, 70% yield) as a white solid. MS (ESI): m/z 372.4 (M+H)+.

Step 7: To a solution of 4-chloroaniline (66 mg, 0.52 mmol) in THF (5 mL) was added i-PrMgCl (2.0 mol/L in THF, 0.3 mL, 0.52 mmol) at 0° C. Then mixture was stirred at rt for 5 minutes, and a solution of compound 115f (50 mg, 0.13 mmol) in THF (2 mL) was added. The reaction was stirred at rt overnight, and quenched with saturated $NH_4Cl$ aqueous, extracted with EtOAc. The combined organic layer was dried over $Na_2SO_4$, filtered, and concentrated. The residue was further purified by reversed pre-HPLC to give compound 115 (15.06 mg, 26% yield) as a white solid. MS (ESI): m/z 453.4 (M+H)+. $^1$H NMR (500 MHz, $d_6$-DMSO) δ 10.38 (s, 1H), 8.77 (d, J=4.5 Hz, 1H), 8.07 (d, J=7.5 Hz, 1H), 7.97 (d, J=12.5 Hz, 1H), 7.65 (d, J=9.0 Hz, 2H), 7.34 (d, J=9.0 Hz, 2H), 7.31 (d, J=4.5 Hz, 1H), 4.72 (s, 2H), 3.46-3.38 (m, 1H), 3.28 (s, 3H), 2.23-2.15 (m, 1H), 1.98-1.83 (m, 4H), 1.77 (d, J=11.5 Hz, 1H), 1.74-1.69 (m, 1H), 1.34-1.25 (m, 1H), 1.17-1.13 (m, 1H), 1.10 (d, J=13.0 Hz, 1H), 0.93 (dd, J=7.5, 4.0 Hz, 1H).

Biological Evaluations:

Example 1: Study on the Activity of the Compound of the Present Invention in Hela Cells Hela cells were seeded in 96-well culture plates and incubated at 37° C., 100% relative humidity, 5% $CO_2$ incubator for 24 hours. The compound was dissolved in DMSO and diluted to an appropriate concentration, and then the compound was diluted 100-fold with DMEM medium containing interferon-γ and 10% fetal bovine serum to the final concentration of effect. Aspirate the old medium from the 96-well plate and add 200 μL of each medium containing compound and interferon-γ from the previous step. The content of tryptophan in the medium is 16 mg/L, and the concentration of interferon-γ is 50 ng/mL. The cells were placed in a 37° C., 100% relative humidity, and 5% $CO_2$ incubator for 48 hours, then 140 μL of the cell culture supernatant was mixed with 15 μL of trichloroacetic acid, and placed at 52° C. for 30 min, then centrifuged at room temperature to take the centrifugal supernatant. Mix with an equal volume of Ehrlich's reagent, measure the light absorption at 480 nm, and calculate the $IC_{50}$ values.

| Compound NO. | $IC_{50}$ |
|---|---|
| 1 | A |
| 2 | B |
| 3 | C |
| 4 | C |
| 5 | C |
| 6 | B |
| 7 | B |
| 8 | B |
| 9 | A |
| 10a | A |
| 10b | C |
| 11 | A |
| 12 | B |
| 13 | B |
| 14 | A |
| 15 | A |
| 16 | A |
| 17 | A |
| 18 | A |
| 19 | A |
| 24 | C |
| 50 | B |
| 51 | B |
| 52 | B |
| 53 | B |
| 54 | B |
| 55 | B |
| 80 | A |
| 81 | A |
| 82 | A |
| 83 | A |
| 84 | A |
| 85 | A |
| 86 | A |
| 87 | C |
| 88 | C |
| 89 | C |
| 90 | C |
| 91 | C |
| 92 | A |
| 93 | C |
| 94 | A |
| 95 | A |
| 96 | B |
| 97 | C |
| 98 | A |
| 99 | C |
| 100 | A |
| 101 | A |
| 102 | A |
| 103 | C |
| 104 | C |
| 105 | B |
| 106 | C |
| 107 | C |
| 108 | A |
| 109 | C |
| 110 | B |
| 111 | C |
| 112 | B |
| 113 | A |
| 114 | A |
| 115 | A |

Note:
A: $IC_{50}$ = 0.1 nM~10 nM; B: $IC_{50}$ = 10 nM~100 nM; C: $IC_{50}$ > 100 nM.

Example 2: Study on the Activity of the Present Invention in HEK293 Cells Highly Expressing Human IDO1 Protein HEK293-IDO cells with high expression of human IDO1 protein were prepared by electrotransformation, and the cells were seeded in 96-well culture plates, and cultured at 37° C., 100% relative humidity, and 5% $CO_2$ incubator for 24 hours. Dissolve in DMSO and dilute to the appropriate concentration, then use DMEM medium containing 10% fetal bovine serum to dilute the candidate 100-fold to the final concentration. Aspirate the old medium from the 96-well plate and add 200 µL of the medium contained in the previous step to each well. The content of tryptophan in the medium is 16 mg/L. The cells were placed in a 37° C., 100% relative humidity, and 5% $CO_2$ incubator for 24 hours. 140 µL of the cell culture supernatant was mixed with 15 µL of trichloroacetic acid and placed at 52° C. for 30 min. Mix with an equal volume of Ehrlich's reagent, measure the light absorption at 480 nm, and calculate the $IC_{50}$ values.

| Compound NO. | $IC_{50}$ (HEK293 cell) |
|---|---|
| 1 | B |
| 2 | B |
| 3 | C |
| 4 | C |
| 5 | B |
| 6 | B |
| 7 | B |
| 8 | B |
| 9 | A |
| 10a | A |
| 10b | C |
| 11 | B |
| 12 | B |
| 13 | B |
| 92 | A |
| 93 | C |
| 94 | B |
| 95 | B |
| 96 | C |
| 97 | C |
| 98 | A |
| 99 | C |
| 100 | B |
| 101 | B |
| 102 | B |
| 103 | C |
| 104 | C |
| 105 | A |
| 106 | C |
| 107 | C |
| 108 | A |
| 109 | C |
| 110 | C |
| 111 | C |

| Compound NO. | $IC_{50}$ (HEK293 cell) |
|---|---|
| 112 | C |
| 113 | B |
| 114 | B |

Note:
A: $IC_{50}$ = 0.1 nM~10 nM; B: $IC_{50}$ = 10 nM~100 nM; C: $IC_{50}$ > 100 nM.

The invention claimed is:

1. A compound represented by formula (I):

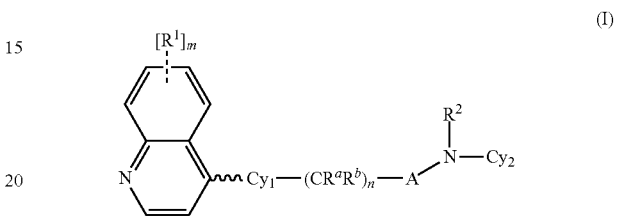

(I)

in free or pharmaceutically acceptable salt form,
wherein ~~~ represents: ——, ⅰⅰⅰⅰⅰⅰ or ▬▬▬;
wherein A represents —C(O)—;
each $R^1$ is respectively selected from halogen and $C_{1-6}$alkyl;
$Cy_1$ is

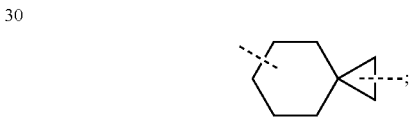

$R^a$, $R^b$, $R^2$ are each independently hydrogen;
$Cy_2$ is $C_5$-$C_{10}$ aryl with one substituent, wherein the substituent is selected from halogen, cyano, $C_{1-6}$alkyl, and $C_{1-6}$alkoxy;
m is 2, and
n is 0.

2. The compound of claim 1 with a structure of:

| NO. | Compound structure |
|---|---|
| 9 | 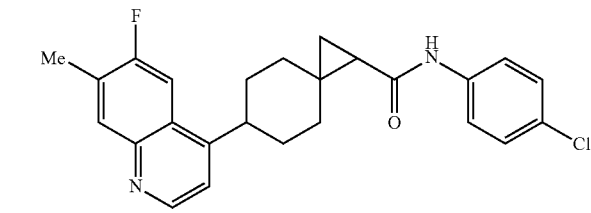 |
| 80 | 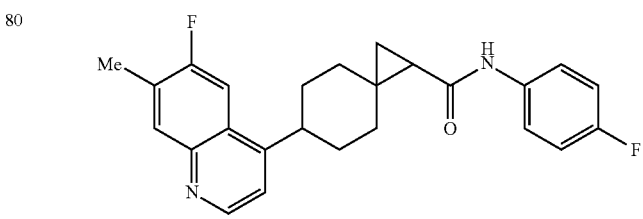 |

-continued

| NO. | Compound structure |
|---|---|
| 81 | (structure) |
| 83 | (structure) |
| 84 | (structure) |
| 85 | (structure) |
| 92 | (structure) |
| 100 | (structure) | wherein ⌇⌇⌇ represents ——— , ⁞⁞⁞⁞ or ▬▬ ..

3. A pharmaceutical composition comprising a therapeutically effective amount of the compound of claim 1 and a carrier.

* * * * *